(12) United States Patent
Alberati-Giani et al.

(10) Patent No.: US 7,462,617 B2
(45) Date of Patent: Dec. 9, 2008

(54) SUBSTITUTED ACYLPIPERAZINE DERIVATIVES

(75) Inventors: Daniela Alberati-Giani, Zofingen (CH); Synese Jolidon, Blauen (CH); Robert Narquizian, St. Louis (FR); Matthias Heinrich Nettekoven, Grenzach-Wyhlen (DE); Roger David Norcross, Rheinfelden (CH); Emmanuel Pinard, Linsdorf (FR); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 396 days.

(21) Appl. No.: 10/933,072

(22) Filed: Sep. 1, 2004

(65) Prior Publication Data

US 2005/0059668 A1    Mar. 17, 2005

(30) Foreign Application Priority Data

Sep. 9, 2003    (EP)    .................................    03019682

(51) Int. Cl.
*A61K 31/53* (2006.01)
*A61K 31/496* (2006.01)
*C07D 295/192* (2006.01)
*C07D 409/12* (2006.01)
*C07D 251/22* (2006.01)
*C07D 251/24* (2006.01)
*A61K 31/495* (2006.01)

(52) U.S. Cl. ............. 514/245; 514/252.02; 514/252.14; 514/252.1; 514/253.01; 514/253.11; 514/255.01; 544/212; 544/238; 544/295; 544/357; 544/360; 544/364; 544/391

(58) Field of Classification Search .................. None
See application file for complete search history.

(56) References Cited

U.S. PATENT DOCUMENTS 7,319,099 B2 * 1/2008 Jolidon et al. ................ 514/245

FOREIGN PATENT DOCUMENTS

| EP | 0 171 636 A1 | 2/1986 |
| EP | 0 624 584 B1 | 11/1994 |
| WO | WO 99/44596 A2 | 9/1999 |
| WO | WO 03/004480 A2 | 1/2003 |
| WO | WO 03/035602 A1 | 5/2003 |
| WO | WO 2004/037800 A1 | 5/2004 |
| WO | 2005/014563 * | 2/2005 |
| WO | 2005/023260 * | 3/2005 |

OTHER PUBLICATIONS

CA Registry No. 383903-94-4, Jan. 17, 2002 (entry date in Registry File on STN).*
CA Registry No. 546106-54-1, Jul. 11, 2003 (entry date in Registry File on STN).*
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. Neurobiol. vol. 67, pp. 173-202 (2002).
Carlsson M. L., J. Neural Trans. vol. 105, pp. 525-535 (1998).
Chemical Abstracts Service, XP002308978; Chemcats No. 2002 : 330684.
Chemical Abstracts Service, XP002308979; Chemcats No. 2003:1026314.
Chemical Abstracts Service, XP002308980; Chemcats No. 2001;2814605.
Chemical Abstracts Service, XP002308981; Chemcats No. 2002:2063001.

(Continued)

*Primary Examiner*—Emily Bernhardt
(74) *Attorney, Agent, or Firm*—George W. Johnston; Patricia S. Rocha-Tramaloni; Kimberly J. Prior

(57) ABSTRACT

The invention relates to compounds of formula

I $$\text{Ar-N}\underset{R^1}{\overset{}{\bigcirc}}\text{N-C(O)-}\underset{R^5}{\overset{R^2\ R^3}{\bigcirc}}\text{-}R^4$$

wherein the substituents are as defined in the specification and to pharmaceutically acceptable acid addition salts thereof.

The invention further relates to methods for the treatment of psychoses, pain, neurodegenerative disfunction in memory and learning, schizophrenia, dementia and other d1iseases in which cognitive processes are impaired, such as attention deficit disorders or Alzheimer's disease.

16 Claims, No Drawings

OTHER PUBLICATIONS

Chemical Abstracts Service, XP002308983; Chemcats No. 2003:1026533.
Chemical Abstracts Service, XP002308984; Chemcats No. 2002:2288893.
Chemical Abstracts Service, XP002308985; Chemcats No. 2003:709504.
Chemical Abstracts Service, XP002308986; Chemcats No. 2003:709503.
Chemical Abstracts Service, XP002308987; Chemcats No. 2003:709505.
Chemical Abstracts Service, XP002308988; Chemcats No. 2004:1498769.
Chemical Abstracts Service, XP002308989; Chemcats No. 2002:2386068.
Chemical Abstracts Service, XP002308990; Chemcats No. 2002:2894607.
Chemical Abstracts Service, XP002308991; Chemcats No. 2003:3342164.
Chemical Abstracts Service, XP002308992; Chemcats No. 2003:3345505.
Chemical Abstracts Service, XP002308993; Chemcats No. 2003:3346187.
Chemical Abstracts Service, XP002309007; Chemcats No. 2004:660630.

* cited by examiner

SUBSTITUTED ACYLPIPERAZINE DERIVATIVES

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly address negative and cognitive symptoms which are the best redictors of functional outcome (Sharma T., *Br. J. Psychiatry*, 174(suppl. 28): 44-51, 1999).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., *Cell*, 98: 427-236, 1999).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Wiley, NY; Bliss T V and Collingridge G L, *Nature*, 361: 31-39, 1993). Transgenic mice over-expressing the NMDA NR2B subunit exhibit enhanced synaptic plasticity and superior ability in learning and memory (Tang J P et al., *Natur*, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, *Trends in Pharm. Sci.*, 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA*, 95: 15730-15734, 1998; Chen L. et al., *J. Neurophysiol.*, 89(2): 691-703, 2003).

Glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans,.* 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention relates to compounds of formula I and their pharmaceutically acceptable salts, to pharmaceutical composition containing them. The present invention also relates to use of the compounds of the invention for the treatment of diseases related to activation of NMDA receptors via Glyt-1 inhibition and for the treatment of neurological and neuropsychiatric disorders.

In one embodiment, the present invention relates to compounds of formula

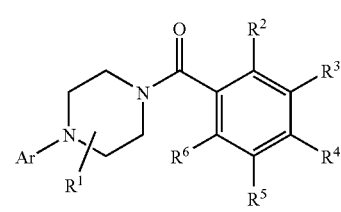

I wherein

Ar is substituted aryl or unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ is halogen,
$(C_1-C_6)$-alkyl,
$(C_2-C_6)$-alkenyl, wherein a hydrogen atom is optionally replaced by CN, C(O)—$R^9$ or
$(C_1-C_6)$-alkyl,
or is $(C_2-C_6)$-alkynyl,
$(C_1-C_6)$-alkyl substituted by halogen,
—$(CH_2)_n$—$(C_3-C_7)$-cycloalkyl,
—$(CH_2)_n$-heterocycloalkyl, —C(O)—$R^9$,
—$(CH_2)_n$-aryl or —$(CH_2)_n$-5 or -6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;

$R^3$, $R^4$ and $R^6$ are each independently hydrogen, hydroxy, halogen, $(C_1-C_6)$-alkyl or $(C_1-C_6)$-alkoxy;

$R^5$ is $NO_2$, CN, $C(O)R^9$, $SO_2R^{10}$ or $NR^{11}R^{12}$;

$R^7$ and $R^8$ are each independently hydrogen or $(C_1-C_6)$-alkyl;

$R^9$ is $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(C_3-C_6)$-cycloalkyl or $NR^7R^8$;

$R^{11}$ and $R^{12}$ are each independently hydrogen, or form together with the N-atom to which they are attached a 5-membered heteroaryl group;

n is 0, 1 or 2;

or a pharmaceutically acceptable acid addition salt thereof, with the proviso that 1-(2-chloro-5-nitrobenzoyl)-4-(4-methoxyphenyl)-piperazine, 1-(2-chloro-5-nitrobenzoyl)-4-(4-chlorophenyl)-piperazine, 1-(2-fluoro-5-nitrobenzoyl)-4-[2-fluoro-4-(1-oxobutyl)phenyl]-piperazine, 1-(2-fluoro-5-nitrobenzoyl)-4-[2-fluoro-4-(1-oxopropyl)phenyl]-piperazine, 1-(2-chloro-5-nitrobenzoyl)-4-(2,3-dimethylphenyl)-piperazine, 1-(2-chloro-5-nitrobenzoyl)-4-(3-chlorophenyl)-piperazine, 1-(2-chloro-5-nitrobenzoyl)-4-(2-ethoxyphenyl)-piperazine, 1-(4-acetyl-2-fluorophenyl)-4-(2-fluoro-5-nitrobenzoyl)-piperazine, 1-(2-chloro-5-nitrobenzoyl)-4-(4-fluorophenyl)-piperazine, 1-(2-chloro-5-nitrobenzoyl)-4-(2-methoxyphenyl)-piperazine, and 1-(4-acetyl-2-fluoro-5-methylphenyl)-4-(2-fluoro-5-nitrobenzoyl)-piperazine are excluded.

These excluded compounds are commercially available products.

Furthermore, the invention includes all racemic mixtures, all their corresponding enantiomers and/or optical isomers.

It has surprisingly been found that the compounds of general formula I are good inhibitors of the glycine transporter 1 (GlyT-1), and that they have a good selectivity to glycine transporter 2 (GlyT-2) inhibitors. Compounds of the invention are useful in the control or prevention of illnesses such as psychoses, disfunction in memory and learning, schizophrenia, dementia and other diseases in which cognitive processes are impaired, such as attention deficit disorders or Alzheimer's disease. The preferred indications, using the compounds of the present invention, are schizophrenia, cognitive impairment and Alzheimer's disease.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes a saturated straight-or branched-chain group containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "alkenyl" denotes an unsaturated straight-or branched-chain group containing from 2 to 6 carbon atoms with at least one double bond, and the term "alkynyl" denotes an unsaturated straight-or branched-chain group containing from 2 to 6 carbon atoms with at least one triple bond.

The term "alkoxy" denotes the residue —O—R, wherein R is a lower alkyl residue as defined herein. Examples of alkoxy radicals include, but are not limited to, methoxy, ethoxy, isopropoxy, and the like.

The term "cycloalkyl" denotes a saturated or partially saturated ring containing from 3 to 7 carbon atoms, for example cyclopropyl, cyclopentyl, cyclopentenyl, cyclohexyl, cyclohexenyl, cycloheptyl or cycloheptenyl.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl.

The term "6-membered heteroaryl containing one, two or three nitrogen atoms" denotes a monovalent aromatic carbocyclic radical, for example pyridyl, pyrazinyl, pyrimidinyl, pyridazinyl or triazinyl.

The term "heterocycloalkyl" denotes a non aromatic hydrocarbon radical, for example oxetanyl, tetrahydrofuranyl, dihydropyranyl, tetrahydropyranyl, azetidinyl; pyrrolidinyl, piperidinyl, piperazinyl, morpholinyl, thiomorpholinyl.

The term "5 or 6-membered heteroaryl containing one, two or three heteroatoms selected from the group consisting of oxygen, sulphur or nitrogen" denotes a monovalent aromatic carbocyclic radical, for example pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl or isoxazolyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically inert," such as therapeutically inert carrier, excipient, etc., means pharmacologically acceptable and substantially non-toxic to the subject to which the particular compound is administered.

"Therapeutically effective amount" means an amount that is effective to prevent, alleviate, or ameliorate symptoms of disease or prolong the survival of the subject being treated.

The present invention relates to compounds of formula I and their pharmaceutically acceptable salts, to pharmaceutical composition containing them. The present invention also relates to use of the compounds of the invention for the treatment of diseases related to activation of NMDA receptors via Glyt-1 inhibition and for the treatment of neurological and neuropsychiatric disorders.

The present invention relates to compounds of formula

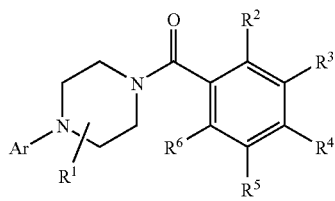

I wherein
Ar is substituted aryl or unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;
$R^1$ is hydrogen or $(C_1-C_6)$-alkyl;
$R^2$ is halogen,
  $(C_1-C_6)$-alkyl,
  $(C_2-C_6)$-alkenyl, wherein a hydrogen atom is optionally replaced by CN, C(O)—$R^9$ or
  $(C_1-C_6)$-alkyl,
  or is $(C_2-C_6)$-alkynyl,
  $(C_1-C_6)$-alkyl substituted by halogen,
  —$(CH_2)_n$—$(C_3-C_7)$-cycloalkyl,
  —$(CH_2)_n$-heterocycloalkyl, —C(O)—$R^9$,
  —$(CH_2)_n$-aryl or —$(CH_2)_n$-5 or -6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;
$R^3$, $R^4$ and $R^6$ are each independently hydrogen, hydroxy, halogen, $(C_1-C_6)$-alkyl or $(C_1-C_6)$-alkoxy;
$R^5$ is $NO_2$, CN, $C(O)R^9$, $SO_2R^{10}$ or $NR^{11}R^{12}$;
$R^7$ and $R^8$ are each independently hydrogen or $(C_1-C_6)$-alkyl;
$R^9$ is $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(C_3-C_6)$-cycloalkyl or $NR^7R^8$;
$R^{11}$ and $R^{12}$ are each independently hydrogen, or form together with the N-atom to which they are attached a 5-membered heteroaryl group;
n is 0, 1 or 2;

and to pharmaceutically acceptable acid addition salts thereof, with the proviso that
1-(2-chloro-5-nitrobenzoyl)-4-(4-methoxyphenyl)-piperazine,
1-(2-chloro-5-nitrobenzoyl)-4-(4-chlorophenyl)-piperazine,
1-(2-fluoro-5-nitrobenzoyl)-4-[2-fluoro-4-(1-oxobutyl)phenyl]-piperazine,
1-(2-fluoro-5-nitrobenzoyl)-4-[2-fluoro-4-(1-oxopropyl) phenyl]-piperazine,
1-(2-chloro-5-nitrobenzoyl)-4-(2,3-dimethylphenyl)-piperazine,
1-(2-chloro-5-nitrobenzoyl)-4-(3-chlorophenyl)-piperazine,
1-(2-chloro-5-nitrobenzoyl)-4-(2-ethoxyphenyl)-piperazine,
1-(4-acetyl-2-fluorophenyl)-4-(2-fluoro-5-nitrobenzoyl)-piperazine,
1-(2-chloro-5-nitrobenzoyl)-4-(4-fluorophenyl)-piperazine,
1-(2-chloro-5-nitrobenzoyl)-4-(2-methoxyphenyl)-piperazine, and
1-(4-acetyl-2-fluoro-5-methylphenyl)-4-(2-fluoro-5-nitrobenzoyl)-piperazine are excluded.

These excluded compounds are commercially available products.

Furthermore, the invention includes all racemic mixtures, all their corresponding enantiomers and/or optical isomers.

Preferred compounds of formula I are those of formula

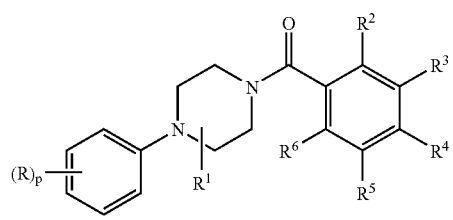

I-1 wherein
R is hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ or $SO_2R^{10}$;
p is 1, 2 or 3;
$R^1$ is hydrogen;
$R^2$ is halogen,
  $(C_1-C_6)$-alkyl,
  $(C_2-C_6)$-alkenyl, wherein a hydrogen atom may be replaced by CN, C(O)—$R^9$ or
  $(C_1-C_6)$-alkyl,
  or is $(C_2-C_6)$-alkynyl,
  $(C_1-C_6)$-alkyl substituted by halogen,
  —$(CH_2)_n$—$(C_3-C_7)$-cycloalkyl,
  —$(CH_2)_n$-heterocycloalkyl,
  —C(O)—$R^9$,
  aryl or 5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;
$R^3$, $R^4$ and $R^6$ are hydrogen;
$R^5$ is $NO_2$ or $SO_2R^{10}$;
$R^7$ and $R^8$ are each independently hydrogen or $(C_1-C_6)$-alkyl;
$R^9$ is $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(C_3-C_6)$-cycloalkyl or $NR^7R^8$;
n is 0, 1 or 2;

or a pharmaceutically acceptable acid addition salt thereof.
A preferred group of compounds of formula I-1 are those, wherein $R^2$ is aryl, unsubstituted or substituted by one or more substituents selected from the group consisting of hydroxy, halogen, $(C_1-C_6)$-alkyl, $(C_1-C_6)$-alkyl substituted by halogen, and $(C_1-C_6)$-alkoxy and the other substituents are as described above, for example the following compounds:

1-{3-fluoro-4-[4-(4-nitro-biphenyl-2-carbonyl)-piperazin-1-yl]-phenyl}-ethanone, (4-methanesulfonyl-biphenyl-2-yl)-[4-(4-trifluoromethyl-phenyl)-piperazin-1-yl]-methanone, (4'-fluoro-4-methanesulfonyl-biphenyl-2-yl)-[4-(4-trifluoromethyl-phenyl)-piperazin-1-yl]-methanone,

[4-(2-fluoro-4-trifluoromethyl-phenyl)-piperazin-1-yl]-(4-methanesulfonyl-biphenyl-2-yl)-methanone, (4'-fluoro-4-methanesulfonyl-biphenyl-2-yl)-[4-(2-fluoro-4-trifluoromethyl-phenyl)-piperazin-1-yl]-methanone, 2-[4-(4-trifluoromethyl-phenyl)-piperazine-1-carbonyl]-biphenyl-4-sulfonic acid methylamide, 3-fluoro-4-[4-(4-methanesulfonyl-biphenyl-2-carbonyl)-piperazin-1-yl]-benzonitrile and 3-fluoro-4-[4-(2'-fluoro-4-methanesulfonyl-biphenyl-2-carbonyl)-piperazin-1-yl]-benzonitrile.

A further preferred group of compounds of formula I-1 are those, wherein $R^2$ is $(C_3-C_7)$-cycloalkyl, for example the following compounds:

1-{4-[4-(2-cyclopropyl-5-nitro-benzoyl)-piperazin-1-yl]-3-fluoro-phenyl}-ethanone, 1-{4-[4-(2-cyclohex-1-enyl-5-methanesulfonyl-benzoyl)-piperazin-1-yl]-3-fluoro-phenyl}-ethanone, (2-cyclohexyl-5-methanesulfonyl-phenyl)-[4-(4-ethyl-2-fluoro-phenyl)-piperazin-1-yl]-methanone, 1-{4-[4-(2-cyclopent-1-enyl-5-methanesulfonyl-benzoyl)-piperazin-1-yl]-3-fluoro-phenyl}-ethanone, 1-{4-[4-(2-cyclohept-1-enyl-5-methanesulfonyl-benzoyl)-piperazin-1-yl]-3-fluoro-phenyl}-ethanone, (2-cyclohept-1-enyl-5-methanesulfonyl-phenyl)-[4-(4-trifluoromethyl-phenyl)-piperazin-1-yl]-methanone, (2-Cyclohex-1-enyl-5-methanesulfonyl-phenyl)-[4-(4-trifluoromethyl-phenyl)-piperazin-1-yl]-methanone, (2-cyclohexyl-5-methanesulfonyl-phenyl)-[4-(4-trifluoromethyl-phenyl)-piperazin-1-yl]-methanone and (2-cyclopentyl-5-methanesulfonyl-phenyl)-[4-(4-trifluoromethyl-phenyl)-piperazin-1-yl]-methanone.

A preferred group of compounds of formula I-1 are further those, wherein $R^2$ is heterocycloalkyl, for example the following compounds:

[2-(3,6-dihydro-2H-pyran-4-yl)-5-methanesulfonyl-phenyl]-[4-(4-trifluoromethyl-phenyl)-piperazin-1-yl]-methanone,

[5-methanesulfonyl-2-(tetrahydro-pyran-4-yl)-phenyl]-[4-(4-trifluoromethyl-phenyl)-piperazin-1-yl]-methanone, 1-(4-{4-[2-(3,6-dihydro-2H-pyran-4-yl)-5-methanesulfonyl-benzoyl]-piperazin-1-yl}-3-fluoro-phenyl)-ethanone and 4-{4-[2-(3,6-dihydro-2H-pyran-4-yl)-5-methanesulfonyl-benzoyl]-piperazin-1-yl}-3-fluoro-benzonitrile.

A further preferred group of compounds of formula I-1 are those, wherein $R^2$ is a 5 or-6-membered heteroaryl group containing one, two or three heteroatoms selected from the group consisting of oxygen, sulphur or nitrogen, unsubstituted or substituted by $(C_1-C_6)$-alkyl, for example the following compounds:

(5-methanesulfonyl-2-thiophen-2-yl-phenyl)-[4-(4-trifluoromethyl-phenyl)-piperazin-1-yl]-methanone, (5-methanesulfonyl-2-thiophen-3-yl-phenyl)-[4-(4-trifluoromethyl-phenyl)-piperazin-1-yl]-methanone,

[5-methanesulfonyl-2-(5-methyl-thiophen-2-yl)-phenyl]-[4-(4-trifluoromethyl-phenyl)-piperazin-1-yl]-methanone, (5-methanesulfonyl-2-pyridin-4-yl-phenyl)-[4-(4-trifluoromethyl-phenyl)-piperazin-1-yl]-methanone,

[4-(2-fluoro-4-trifluoromethyl-phenyl)-piperazin-1-yl]-(5-methanesulfonyl-2-thiophen-3-yl-phenyl)-methanone and 1-{4-[4-(5-methanesulfonyl-2-thiophen-3-yl-benzoyl)-piperazin-1-yl]-phenyl}-ethanone.

A preferred group of compounds of formula I-1 are further those, wherein $R^2$ is halogen; $(C_1-C_6)$-alkyl; $(C_2-C_6)$-alkenyl, wherein a hydrogen atom may be replaced by CN, C(O)—$R^9$ or $(C_1-C_6)$-alkyl; or is $(C_2-C_6)$-alkynyl; $(C_1-C_6)$-alkyl substituted by halogen or —C(O)—$R^9$, for example the compound 2-[4-(4-acetyl-2-fluoro-phenyl)-piperazine-1-carbonyl]-4-nitro-benzoic acid methyl ester.

Preferred compounds of formula I are further those of formula

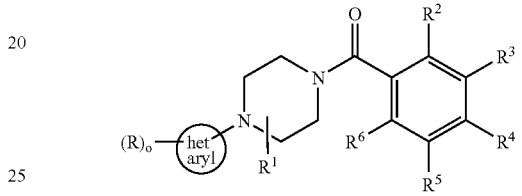

I-2 wherein

R is hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ or $SO_2R^{10}$;

o is 0, 1, 2 or 3;

$R^1$ is hydrogen;

$R^2$ is halogen,
  $(C_1-C_6)$-alkyl,
  $(C_2-C_6)$-alkenyl, wherein a hydrogen atom may be replaced by CN, C(O)—$R^9$ or
  $(C_1-C_6)$-alkyl,
  or is $(C_2-C_6)$-alkynyl,
  $(C_1-C_6)$-alkyl substituted by halogen,
  —$(CH_2)_n$—$(C_3-C_7)$-cycloalkyl,
  —$(CH_2)_n$-heterocycloalkyl,
  —C(O)—$R^9$,
  aryl or 5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;

$R^3$, $R^4$ and $R^6$ are hydrogen;

$R^5$ is $NO_2$ or $SO_2R^{10}$;

$R^7$ and $R^8$ are each independently hydrogen or $(C_1-C_6)$-alkyl;

$R^9$ is $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(C_3-C_6)$-cycloalkyl or $NR^7R^8$;

n is 0, 1 or 2;

or a pharmaceutically acceptable acid addition salt thereof.

Further preferred compounds of formula I-2 are those, wherein $R^2$ is aryl, unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy and the other substituents are as described above, for example the following compounds:

[4-(3-chloro-5-trifluoromethyl-pyridin-2-yl)-piperazin-1-yl]-(2'-fluoro-4-methanesulfonyl-biphenyl-2-yl)-methanone and
[4-(3-chloro-5-trifluoromethyl-pyridin-2-yl)-piperazin-1-yl]-(4-methanesulfonyl-biphenyl-2-yl)-methanone.

A further preferred group of compounds of formula I-2 are those, wherein $R^2$ is a 5 or-6-membered heteroaryl group containing one, two or three heteroatoms selected from the group consisting of oxygen, sulphur and nitrogen, for example the following compound:
[4-(3-chloro-5-trifluoromethyl-pyridin-2-yl)-piperazin-1-yl]-(5-methanesulfonyl-2-thiophen-3-yl-phenyl)-methanone.

One embodiment of the invention are compounds of formula

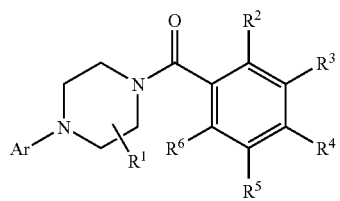

IA wherein
Ar is substituted aryl or unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;
$R^1$ is hydrogen or $(C_1-C_6)$-alkyl;
$R^2$ is halogen, $(C_1-C_6)$-alkyl, $(C_2-C_6)$-alkenyl, $(C_2-C_6)$-alkynyl, $(C_1-C_6)$-alkyl substituted by halogen, $(C_3-C_7)$-cycloalkyl, heterocycloalkyl, $(C_1-C_6)$-alkyl-$(C_3-C_7)$-cycloalkyl, $(C_1-C_6)$-alkyl-heterocycloalkyl, —$C(O)$—$R^9$, aryl or 5 or-6-membered heteroaryl containing one, two or three heteroatoms, selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;
$R^3$, $R^4$ and $R^6$ are each independently hydrogen, hydroxy, halogen, CN, $(C_1-C_6)$-alkyl, $(C_1-C_6)$-alkoxy or $NR^7R^8$;
$R^5$ is $NO_2$, CN, $C(O)R^9$, $SO_2R^{10}$ or $NR^{11}R^{12}$;
$R^7$ and $R^8$ are each independently hydrogen or $(C_1-C_6)$-alkyl;
$R^9$ is hydroxy, $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(C_3-C_6)$-cycloalkyl or $NR^7R^8$;
$R^{11}$ and $R^{12}$ are each independently hydrogen, $C(O)$—$(C_1-C_6)$-alkyl, $SO_2$—$(C_1-C_6)$-alkyl, or form together with the N-atom to which they are attached a 5-membered heteroaryl group, optionally substituted by halogen, $(C_1-C_6)$-alkyl, $(C_1-C_6)$-alkyl substituted by halogen or $(C_3-C_6)$-cycloalkyl;

or a pharmaceutically acceptable acid addition salt thereof, with the proviso that
1-(2-chloro-5-nitrobenzoyl)-4-(4-methoxyphenyl)-piperazine,
1-(2-chloro-5-nitrobenzoyl)-4-(4-chlorophenyl)-piperazine,
1-(2-fluoro-5-nitrobenzoyl)-4-[2-fluoro-4-(1-oxobutyl)phenyl]-piperazine,
1-(2-fluoro-5-nitrobenzoyl)-4-[2-fluoro-4-(1-oxopropyl)phenyl]-piperazine,
1-(2-chloro-5-nitrobenzoyl)-4-(2,3-dimethylphenyl)-piperazine,
1-(2-chloro-5-nitrobenzoyl)-4-(3-chlorophenyl)-piperazine,
1-(2-chloro-5-nitrobenzoyl)-4-(2-ethoxyphenyl)-piperazine,
1-(4-acetyl-2-fluorophenyl)-4-(2-fluoro-5-nitrobenzoyl)-piperazine,
1-(2-chloro-5-nitrobenzoyl)-4-(4-fluorophenyl)-piperazine,
1-(2-chloro-5-nitrobenzoyl)-4-(2-methoxyphenyl)-piperazine, and
1-(4-acetyl-2-fluoro-5-methylphenyl)-4-(2-fluoro-5-nitrobenzoyl)-piperazine are excluded.

In another embodiment of the present invention are compounds of formula Ia

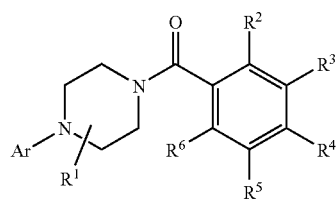

Ia wherein
Ar is aryl, substituted by one or more substituents selected from the group consisting of halogen, $(C_1-C_6)$-alkyl, $(C_1-C_6)$-alkyl substituted by halogen and $C(O)R^9$;
$R^1$ is hydrogen;
$R^2$ is halogen, $(C_1-C_6)$-alkyl, $(C_2-C_6)$-alkenyl, $(C_1-C_6)$-alkyl substituted by halogen, $(C_3-C_7)$-cycloalkyl, heterocycloalkyl, —$C(O)$—$R^9$, aryl or 5 or-6-membered heteroaryl containing one, two or three heteroatoms selected from the group consisting of oxygen, sulphur and nitrogen, wherein aryl, cycloalkyl, heterocycloalkyl and heteroaryl are unsubstituted or substituted by one or more substituents selected from the group consisting of halogen, $(C_1-C_6)$-alkyl, $(C_1-C_6)$-alkyl substituted by halogen and $(C_1-C_6)$-alkoxy;
$R^3$, $R^4$ and $R^6$ are each independently hydrogen or halogen;
$R^5$ is $NO_2$, CN, $SO_2R^{10}$ or $NR^{11}R^{12}$;
$R^7$ and $R^8$ are each independently hydrogen or $(C_1-C_6)$-alkyl;
$R^9$ is $(C_1-C_6)$-alkyl or $(C_1-C_6)$-alkoxy;
$R^{10}$ is $(C_1-C_6)$-alkyl or $NR^7R^8$;
$R^{11}$ and $R^{12}$ form together with the N-atom to which they are attached a tetrazole ring, or a pharmaceutically acceptable acid addition salt thereof, with the proviso that
1-(2-chloro-5-nitrobenzoyl)-4-(4-chlorophenyl)-piperazine,
1-(2-fluoro-5-nitrobenzoyl)-4-[2-fluoro-4-(1-oxobutyl)phenyl]-piperazine,
1-(2-fluoro-5-nitrobenzoyl)-4-[2-fluoro-4-(1-oxopropyl)phenyl]-piperazine,
1-(2-chloro-5-nitrobenzoyl)-4-(2,3-dimethylphenyl)-piperazine,
1-(2-chloro-5-nitrobenzoyl)-4-(3-chlorophenyl)-piperazine,
1-(4-acetyl-2-fluorophenyl)-4-(2-fluoro-5-nitrobenzoyl)-piperazine,
1-(2-chloro-5-nitrobenzoyl)-4-(4-fluorophenyl)-piperazine and 1-(4-acetyl-2-fluoro-5-methylphenyl)-4-(2-fluoro-5-nitrobenzoyl)-piperazine are excluded.

A further embodiment are those compounds of formula Ia, wherein

Ar is phenyl, substituted by one, two or three substituents selected from the group consisting of halogen, methyl, ethyl, $CF_3$ and $C(O)CH_3$;

$R^1$ is hydrogen;

$R^2$ is halogen, methyl, isopropyl, isopropenyl, $CF_3$, cyclopropyl, cyclohexyl, cyclohexenyl, cyclopentenyl, cycloheptenyl, tetrahydropyranyl, dihydropyranyl, —$COOCH_3$, phenyl or 5 or-6-membered heteroaryl containing one or two heteroatoms selected from the group consisting of oxygen, sulphur and nitrogen, wherein phenyl, cyclopropyl and heteroaryl are unsubstituted or substituted by one or more substituents selected from the group consisting of halogen, methyl, $CF_3$ and methoxy;

$R^3$, $R^4$ and $R^6$ are each independently hydrogen or chloro;

$R^5$ is $NO_2$, CN, $SO_2CH_3$, $SO_2NHCH_3$ or tetrazole;

or a pharmaceutically acceptable acid addition salt thereof, with the proviso that 1-(2-chloro-5-nitrobenzoyl)-4-(4-chlorophenyl)-piperazine,
1-(2-fluoro-5-nitrobenzoyl)-4-[2-fluoro-4-(1-oxobutyl)phenyl]-piperazine,
1-(2-fluoro-5-nitrobenzoyl)-4-[2-fluoro-4-(1-oxopropyl)phenyl]-piperazine,
1-(2-chloro-5-nitrobenzoyl)-4-(2,3-dimethylphenyl)-piperazine,
1-(2-chloro-5-nitrobenzoyl)-4-(3-chlorophenyl)-piperazine,
1-(4-acetyl-2-fluorophenyl)-4-(2-fluoro-5-nitrobenzoyl)-piperazine,
1-(2-chloro-5-nitrobenzoyl)-4-(4-fluorophenyl)-piperazine and
1-(4-acetyl-2-fluoro-5-methylphenyl)-4-(2-fluoro-5-nitrobenzoyl)-piperazine are excluded.

An embodiment of the invention are further those compounds, wherein $R^2$ is halogen, for example the following compounds:

1-{4-[4-(2-bromo-5-nitro-benzoyl)-piperazin-1-yl]-3-fluoro-phenyl}-ethanone and
3-[4-(4-acetyl-2-fluoro-phenyl)-piperazine-1-carbonyl]-4-chloro-N-methyl-benzenesulfonamide.

An embodiment of the invention are further those compounds, wherein $R^2$ is phenyl, optionally substituted by fluoro, for example the following compounds:

1-{3-fluoro-4-[4-(4-nitro-biphenyl-2-carbonyl)-piperazin-1-yl]-phenyl}-ethanone,
(4-methanesulfonyl-biphenyl-2-yl)-[4-(4-trifluoromethyl-phenyl)-piperazin-1-yl]-methanone,
(4'-fluoro-4-methanesulfonyl-biphenyl-2-yl)-[4-(4-trifluoromethyl-phenyl)-piperazin-1-yl]-methanone,
(2'-fluoro-4-methanesulfonyl-biphenyl-2-yl)-[4-(4-trifluoromethyl-phenyl)-piperazin-1-yl]-methanone,
(3'-fluoro-4-methanesulfonyl-biphenyl-2-yl)-[4-(4-trifluoromethyl-phenyl)-piperazin-1-yl]-methanone,
(2',4'-difluoro-4-methanesulfonyl-biphenyl-2-yl)-[4-(4-trifluoromethyl-phenyl)-piperazin-1-yl]-methanone,
(3'-fluoro-4-methanesulfonyl-biphenyl-2-yl)-[4-(4-trifluoromethyl-phenyl)-piperazin-1-yl]-methanone,
[4-(2-fluoro-4-trifluoromethyl-phenyl)-piperazin-1-yl]-(4-methanesulfonyl-biphenyl-2-yl)-methanone,
(4'-fluoro-4-methanesulfonyl-biphenyl-2-yl)-[4-(2-fluoro-4-trifluoromethyl-phenyl)-piperazin-1-yl]-methanone and
2-[4-(4-Trifluoromethyl-phenyl)-piperazine-1-carbonyl]-biphenyl-4-sulfonic acid methylamide.

An embodiment of the invention are further those compounds, wherein $R^2$ is cycloalkyl, for example the following compounds:

1-{4-[4-(2-cyclopropyl-5-nitro-benzoyl)-piperazin-1-yl]-3-fluoro-phenyl}-ethanone,
1-{4-[4-(2-cyclohex-1-enyl-5-methanesulfonyl-benzoyl)-piperazin-1-yl]-3-fluoro-phenyl}-ethanone,
(2-cyclohexyl-5-methanesulfonyl-phenyl)-[4-(4-ethyl-2-fluoro-phenyl)-piperazin-1-yl]-methanone,
1-{4-[4-(2-cyclopent-1-enyl-5-methanesulfonyl-benzoyl)-piperazin-1-yl]-3-fluoro-phenyl}-ethanone,
1-{4-[4-(2-cyclohept-1-enyl-5-methanesulfonyl-benzoyl)-piperazin-1-yl]-3-fluoro-phenyl}-ethanone,
(2-cyclopent-1-enyl-5-methanesulfonyl-phenyl)-[4-(4-trifluoromethyl-phenyl)-piperazin-1-yl]-methanone,
(2-cyclohept-1-enyl-5-methanesulfonyl-phenyl)-[4-(4-trifluoromethyl-phenyl)-piperazin-1-yl]-methanone,
(2-cyclohex-1-enyl-5-methanesulfonyl-phenyl)-[4-(4-trifluoromethyl-phenyl)-piperazin-1-yl]-methanone and
(2-cyclohexyl-5-methanesulfonyl-phenyl)-[4-(4-trifluoromethyl-phenyl)-piperazin-1-yl]-methanone.

An embodiment of the invention are further those compounds, wherein $R^2$ is —$C(O)OCH_3$, for example the following compound:

2-[4-(4-acetyl-2-fluoro-phenyl)-piperazine-1-carbonyl]-4-nitro-benzoic acid methyl ester.

An embodiment of the invention are further those compounds, wherein $R^2$ is 5 or-6-membered heteroaryl containing one, two or three heteroatoms selected from the group consisting of oxygen, sulphur and nitrogen, optionally substituted by methyl, for example the following compounds:

(5-methanesulfonyl-2-thiophen-2-yl-phenyl)-[4-(4-trifluoromethyl-phenyl)-piperazin-1-yl]-methanone,
(5-methanesulfonyl-2-thiophen-3-yl-phenyl)-[4-(4-trifluoromethyl-phenyl)-piperazin-1-yl]-methanone,
[5-methanesulfonyl-2-(4-methyl-thiophen-2-yl)-phenyl]-[4-(4-trifluoromethyl-phenyl)-piperazin-1-yl]-methanone,
[5-methanesulfonyl-2-(5-methyl-thiophen-2-yl)-phenyl]-[4-(4-trifluoromethyl-phenyl)-piperazin-1-yl]-methanone,
(5-methanesulfonyl-2-thiazol-2-yl-phenyl)-[4-(4-trifluoromethyl-phenyl)-piperazin-1-yl]-methanone,
(5-methanesulfonyl-2-pyridin-4-yl-phenyl)-[4-(4-trifluoromethyl-phenyl)-piperazin-1-yl]-methanone and
[4-(2-fluoro-4-trifluoromethyl-phenyl)-piperazin-1-yl]-(5-methanesulfonyl-2-thiophen-3-yl-phenyl)-methanone.

An embodiment of the invention are further those compounds, wherein $R^2$ is heterocycloalkyl, for example the following compounds:

[2-(3,6-dihydro-2H-pyran-4-yl)-5-methanesulfonyl-phenyl]-[4-(4-trifluoromethyl-phenyl)-piperazin-1-yl]-methanone,
[5-methanesulfonyl-2-(tetrahydro-pyran-4-yl)-phenyl]-[4-(4-trifluoromethyl-phenyl)-piperazin-1-yl]-methanone and
1-(4-{4-[2-(3,6-dihydro-2H-pyran-4-yl)-5-methanesulfonyl-benzoyl]-piperazin-1-yl}-3-fluoro-phenyl)-ethanone.

The present compounds of formula I and their pharmaceutically acceptable salts can be prepared by methods known in the art, for example, by processes described below, which processes comprise a) reacting a compound of formula

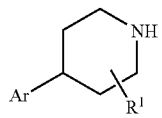

with a compound of formula

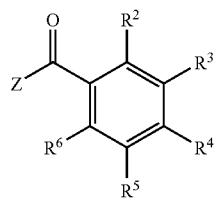

to produce a compound of formula

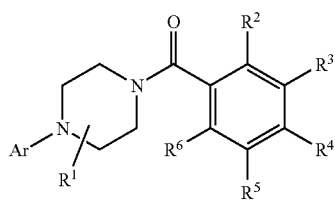

wherein Z is hydroxy or halogen, and the other substituents are as defined above, or b) reacting a compound of formula

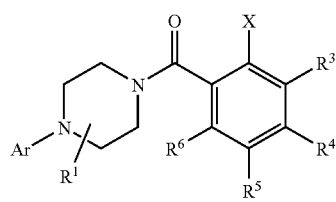

with a compound of formula
$R^2B(OH)_2$ or $R^2B(OR)_2$ in the presence of a palladium catalyst to produce a compound of formula

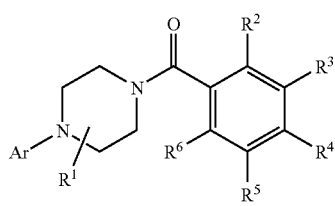

wherein X is halogen and the other substituents are as defined above, or c) reacting a compound of formula

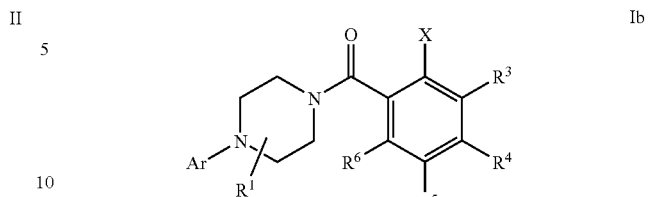

with $R^2SnBu_3$ or $R^2SnMe_3$ in the presence of a palladium catalyst to produce a compound of formula

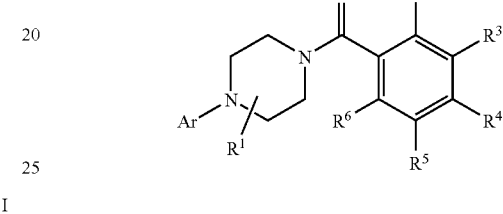

wherein X is halogen and the other substituents are as defined above, or d) reacting a compound of formula

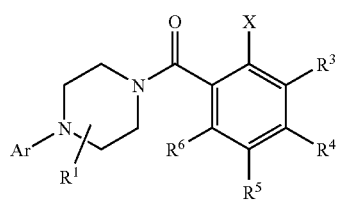

with a compound of formula

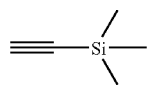

in the presence of a palladium catalyst and base to produce a compound of formula

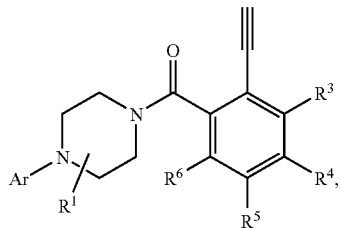

wherein X is halogen and the other substituents are as defined above, or e) hydrogenating a compound of formula

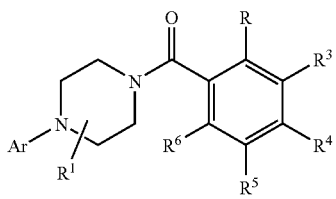

Id wherein R is $(C_2-C_6)$-alkenyl or $(C_2-C_6)$-alkynyl to produce a compound of formula

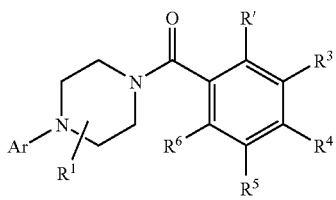

Ie wherein R' is $(C_2-C_6)$-alkyl or $(C_2-C_6)$-alkenyl f) reacting a compound of formula

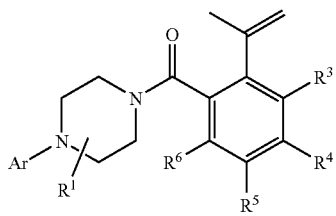

If with trimethylsulfoxonium iodide in the presence of a base to produce a compound of formula

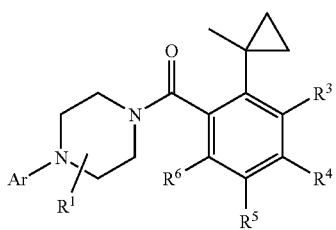

Ig g) reacting a compound of formula

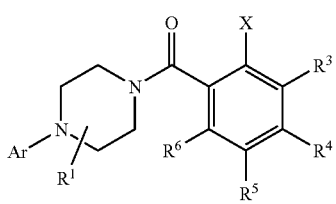

Ib with a compound of formula TMSCF$_3$ in the presence of copper to produce a compound of formula

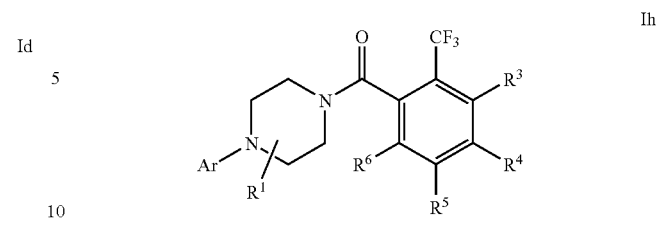

Ih wherein X is halogen and the other substituents are as described above, and if desired, converting the compounds obtained into pharmaceutically acceptable acid addition salts.

The compounds of formula I may be prepared in accordance with process variant a) to g) and with the following schemes 1 to 8.

The starting material is commercially available or may be prepared in accordance with known methods.

Scheme 1

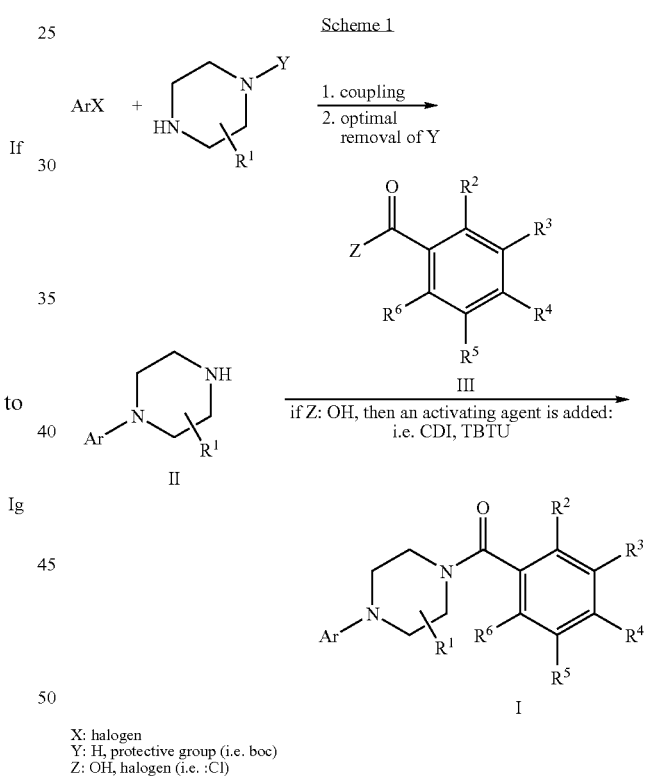

X: halogen
Y: H, protective group (i.e. boc)
Z: OH, halogen (i.e. :Cl)

Ar and $R^1$-$R^6$ are as described above.

Compounds of general formula I can be prepared by reacting a piperazine of formula II with a compound of formula III (Z=Cl) or III (Z=OH) in the presence of an activating agent like CDI ( N,N-carbonyldiimidazole) or TBTU ( 2-(1H-benzotriazole-1-yl)-1,1,3,3-tetramethyluroniumtetrafluoroborate). Piperazines of formula II can be prepared by heating of corresponding piperazines with ArX or by reacting of corresponding N-protected piperazines with ArX in the presence of palladium catalyst, followed by cleavage of the protective group. The protective group is typically tert-butoxycarbonyl (Boc).

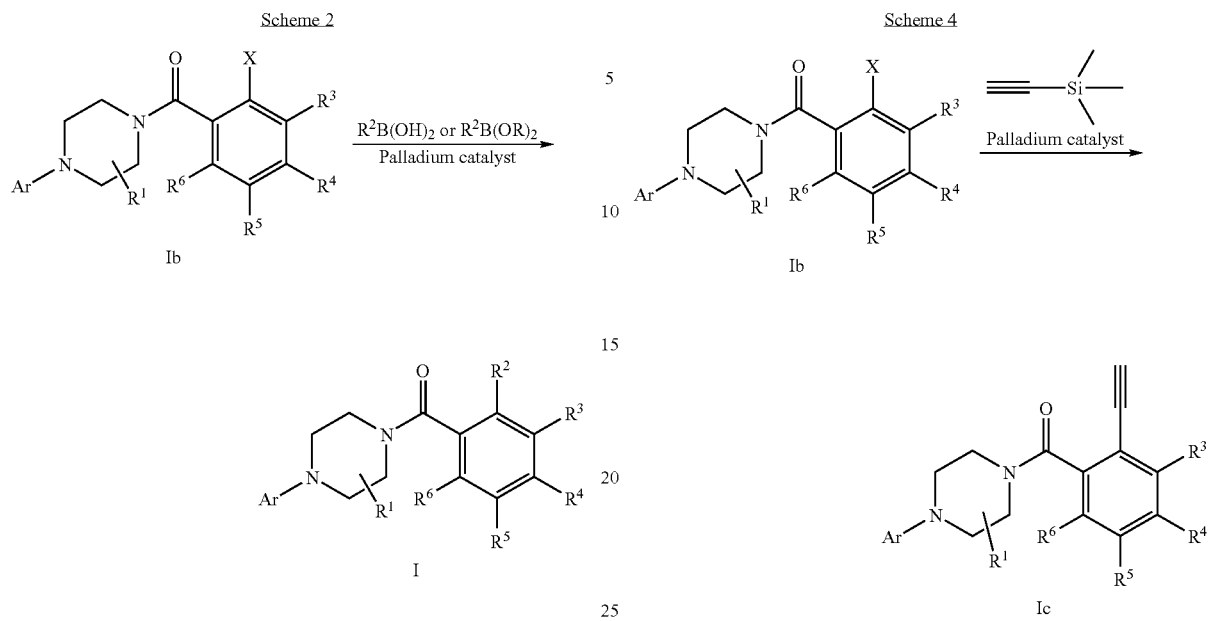

X is Cl, Br or I,
Ar and $R^1$-$R^6$ are as described above.

Compounds of general formula I can be prepared by reacting of a corresponding aryl halide of formula 1b with boronic acids or esters under Suzuki conditions in the presence of a palladium catalyst (e.g. tetrakis(triphenylphosphine) palladium, palladium acetate, tri-tert-butyl phosphine) and a base (e.g. cesium carbonate, sodium carbonate, potassium fluoride).

X is Cl, Br or I.
Ar and $R^1$ and $R^3$-$R^6$ are as described above.

Compounds of general formula Ic can be prepared by reacting an aryl halide of formula Ib with ethynyltrimethylsilane under Sonagashira conditions in the presence of palladium catalyst(e.g. tetrakis(triphenylphosphine) palladium, of copper iodide and base (e.g. triethylamine), followed by a basic treatment to provide compound Ic.

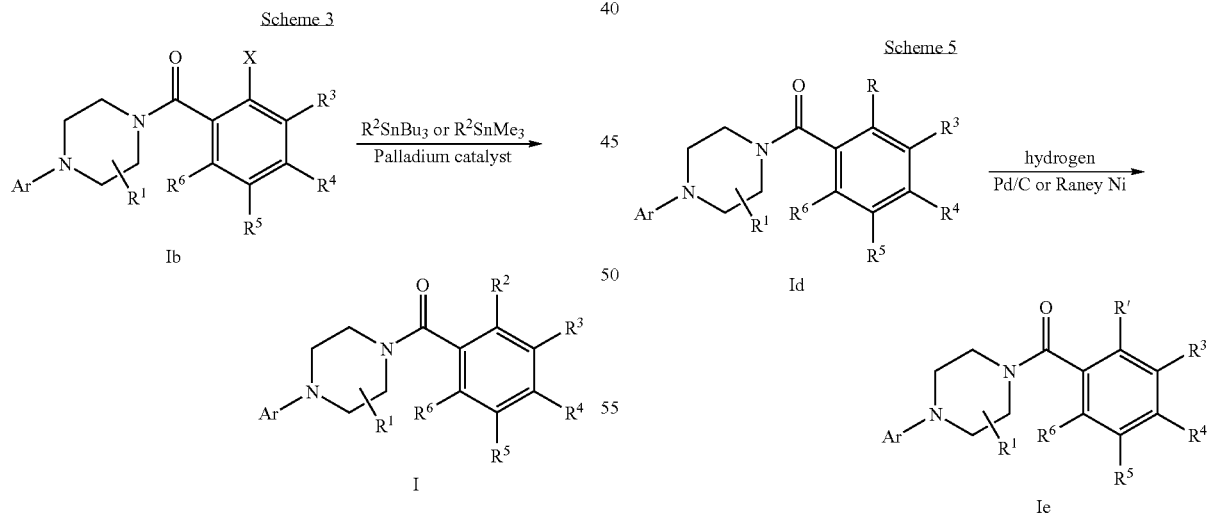

X is Cl, Br or I.
Ar and $R^1$-$R^6$ are as described above.

Compounds of general formula I can be prepared by reacting an aryl halide of formula Ib with an organostannane under Stifle conditions, in the presence of a palladium catalyst (e.g. tris(dibenzylideneacetone)dipalladium chloroform complex), of a ligand (e.g. triphenylarsine) and of copper iodide.

wherein R is $(C_2$-$C_6)$-alkenyl or $(C_2$-$C_6)$-alkynyl and wherein $R^1$ is $(C_2$-$C_6)$-alkyl or $(C_2$-$C_6)$-alkenyl and Ar, $R^1$ and $R^3$-$R^6$ are as described above.

Compounds of general formula Ie which does not contain unsaturation can be prepared by hydrogenation of derivatives of formula Id for which R contain unsaturation, in the presence of hydrogen and catalyst (e.g. Palladium on carbon or Raney Ni).

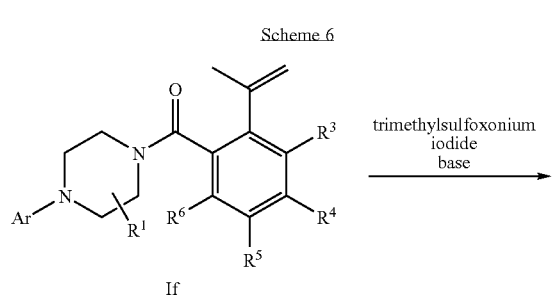

Scheme 6

If

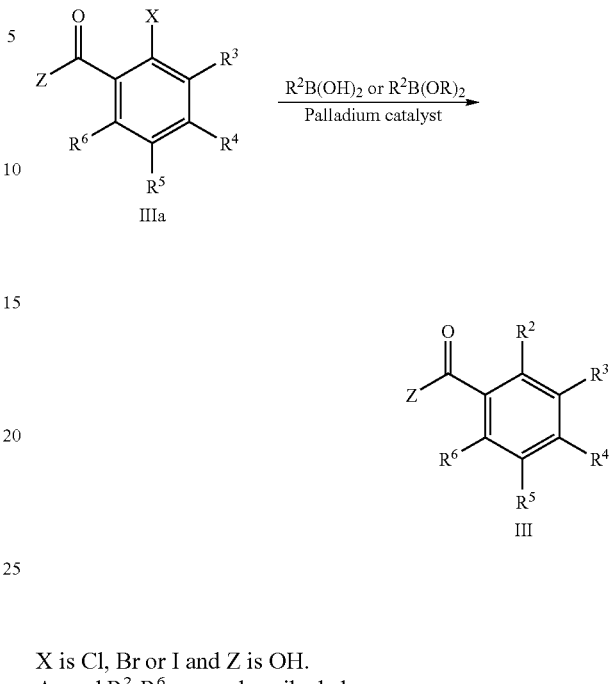

Scheme 8

IIIa

III

X is Cl, Br or I and Z is OH.
Ar and $R^2$-$R^6$ are as described above.

The intermediate compound of formula III with Z=hydroxy can be prepared by reacting an aryl halide of formula IIa with boronic acids or esters under Suzuki conditions in the presence of a palladium catalyst (e.g. tetrakis (triphenylphosphine) palladium, palladium acetate, tri-tert-butyl phosphine, $PdCl2(dppf)_2$) and a base (e.g. cesium carbonate, sodium carbonate, potassium fluoride, potassium hydroxyde).

The acid addition salts of the basic compounds of formula I may be converted to the corresponding free bases by treatment with at least a stoichiometric equivalent of a suitable base, such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated, and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of con- Ar and $R^1$ and $R^3$-$R^6$ are as described above.

The methyl-cyclopropyl compound of formula Ig can be prepared by reacting of an isopropenyl compound of formula If under Corey's conditions in the presence of trimethylsulfoxonium and a base (e.g. potassium tert-butoxyde).

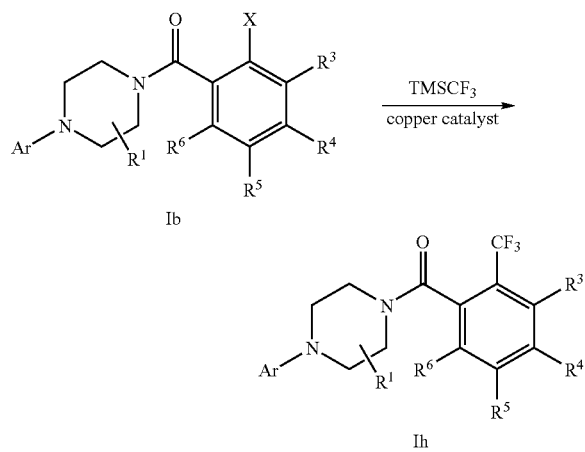

Scheme 7

Ib

Ih

X is Cl, Br or I.
Ar and $R^1$ and $R^3$-$R^6$ are as described above.

Compounds of general formula Ih can be prepared by reacting an aryl halide of formula Ib with (trifluoromethyl) trimethylsilane, in the presence of a copper catalyst (e.g. CuI), and potassium fluoride.

centrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking, and the reaction was stopped by aspiration of the mixture and washing (three times) with ice-cold UB. The cells were lysed with scintillation liquid, shaken 3 hours, and the radioactivity in the cells was counted using a scintillation counter.

The preferred compounds show an $IC_{50}$ (µM) at GlyT-1<0.04.

| Example No. | $IC_{50}$ (µM) |
| --- | --- |
| 15 | 0.023 |
| 16 | 0.026 |
| 17 | 0.031 |
| 18 | 0.029 |
| 43 | 0.032 |
| 52 | 0.033 |
| 53 | 0.006 |
| 55 | 0.039 |
| 59 | 0.033 |
| 60 | 0.019 |
| 62 | 0.019 |
| 63 | 0.01 |
| 67 | 0.04 |
| 68 | 0.007 |
| 69 | 0.031 |
| 71 | 0.013 |
| 72 | 0.021 |
| 73 | 0.013 |
| 75 | 0.014 |
| 76 | 0.012 |
| 77 | 0.011 |
| 78 | 0.025 |
| 79 | 0.008 |
| 91 | 0.022 |
| 111 | 0.038 |
| 114 | 0.035 |
| 125 | 0.02 |
| 126 | 0.039 |
| 127 | 0.036 |

The compounds of formula I and the pharmaceutically acceptable salts of the compounds of formula I can be used as medicaments, e.g. in the form of pharmaceutical compositions. The pharmaceutical compositions can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

Thus, the present invention also provides a method for the treatment of schizophrenia which comprises administering to a patient having schizophrenia a therapeutically effective amount of a compound of formula I or a pharmaceutically acceptable salt thereof and a therapeutically inert carrier. The invention also provides a method for the treatment of cognitive impairment which comprises administering to a patient having cognitive impairment a therapeutically effective amount of a compound of formula I or a pharmaceutically acceptable salt thereof and a therapeutically inert carrier. The invention further provides a method for the treatment of Alzheimer's disease which comprises administering to a patient having Alzheimer's disease a therapeutically effective amount of a compound of formula I or a pharmaceutically acceptable salt thereof and a therapeutically inert carrier.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it. All temperatures are given in degree Celsius.

Intermediates

EXAMPLE A 2-bromo-5-cyano-benzoic

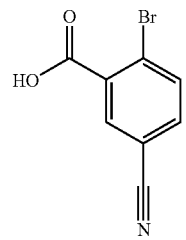

To a suspension of copper (II) bromide (1.6 g, 7.1 mmol) in acetonitrile (30 ml) was added dropwise tert-butylnitrite (1.15 ml, 8.63 mmol) at 0° C. within 2 minutes. 2-Amino-5-cyano-benzoic acid (CAS: 99767-45-0; WO9518097) (1.0 g, 6.17 mmol) was added portionwise within 10 minutes at 0° C.

The mixture was stirred at 0° C. for 2 hours and then at room temperature overnight. Half of the solvent was removed in vacuo. The residue was taken in HCl 1N (15 ml) and ethyl acetate (30 ml). The organic layer was extracted with NaOH 1N (3×10 ml). The aqueous layer was acidified with HCl 2N. The resulting solid was filtered, washed with water and dried (high vacuum, 50° C.) to provide 2-bromo-5-cyano-benzoic (0.92 g, 66%) yellow solid, M+H$^+$=227.1

EXAMPLE B

2-Chloro-5-methanesulfonyl-benzoic acid

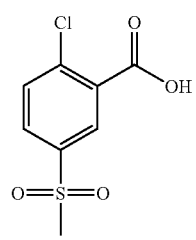

A solution of 2-Chloro-5-(methylthio)benzoic acid (CAS: 51546-12-4; 2.5 g, 11.8 mmol) was dissolved in methanol (50 ml) and cooled to 0° C. Oxone (21.9 g, 35.5 mmol) was added portionwise within 5 minutes. The mixture was stirred at 0° C. for 30 minutes and then at room temperature for 22 hours. The mixture was filtered. The filtrate was poured onto water (200 ml). The aqueous layer was extracted with dichloromethane (5×50 ml). The combined extracts were dried over Na$_2$SO$_4$, filtered and the solvent was removed in vacuo. The solid was stirred in ether (30 ml), filtered and dried (High Vacuum, 50° C.) to provide 2-chloro-5-methanesulfonyl-benzoic acid (1.96 g, 70%) as a beige solid, M–H: 232.9.

EXAMPLE C

2-Iodo-5-methanesulfonyl-benzoic acid

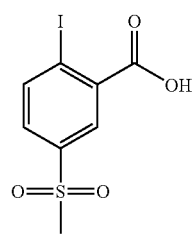

(a) 2-Amino-5-methanesulfonyl-benzoic acid

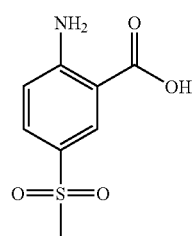

A mixture of 4.26 mmol 2-chloro-5-methanesulfonyl-benzoic acid (see example K, step1), 0.39 mmol Copper powder and 10 ml ammonium hydroxide 25% was heated at 125-130° C. with stirring for 18 hours. Mixture was cooled to room temperature and filtered. The solid was washed with methanol. The filtrate was concentrated in vacuo. The residue was acidified with HCl 1N to pH=2. The obtained solid was washed with water and dried (HV, 50° C., 1 hour) to yield the title compound. MS (m/e): 214.1 (M–H, 100%)

(b) 2-Iodo-5-methanesulfonyl-benzoic acid

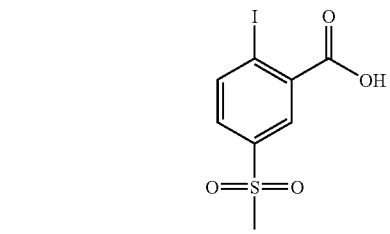

To a suspension of 3.0 mmol 2-amino-5-methanesulfonyl-benzoic acid in a mixture of 1.7 ml sulfuric acid and 1.7 ml water was added dropwise a solution of 3.92 mmol sodium nitrite in 1.7 ml water at such rate that the temperature did not exceed 3° C. The mixture was stirred at 0° C. for 1 hour. A solution of 3.0 mmol KI in 1.7 ml water was added dropwise at 0° C. The brown suspension was allowed to warm to rt and stirred for 30 minutes. Excess iodine was destroyed by addition of a few drops of a sodium hydrogenosulfite solution. The solid was filtered, washed with water and dried (HV, 50° C., 1 hour) to yield the title compound MS (m/e): 325.0 (M–H, 100%)

EXAMPLE D rac-3-Methyl-4-(4-trifluoromethyl-phenyl)-piperazine-1-carboxylic acid tert-butyl ester

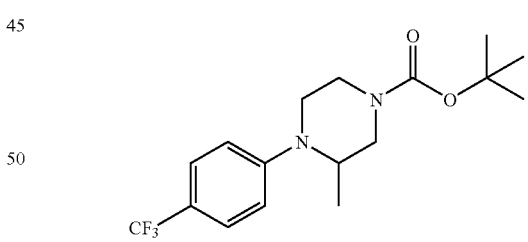

To a solution of 3-Methyl-piperazine-1-carboxylic acid tert-butyl ester (1.0 g, 5.3 mmol) and of 1-Bromo-4-trifluoromethyl-benzene (1.0 g, 4.4 mmol) in toluene (10 ml) were added sodium-tert butylate (0.6 g, 6.2 mmol), 2-(dicyclohexylphosphino)biphenyl (31. mg,89 mmol), and tris(dibenzylideneacetone)dipalladium-chloroform complex (23 mg, 22 mmol). The reaction mixture was then stirred for 16 hours at 80° C. After allowing to cool to room temperature the reaction mixture was concentrated in vacuo and purified by column chromatography (SiO$_2$, 70 g, heptane/ethyl acetate 0-30%) to give the title compound as a light brown solid (0.47 g); MS (m/e): 345.2 (M+H$^+$, 100%).

EXAMPLE E 4-(2-Fluoro-4-trifluoromethyl-phenyl)-piperazine-1-carboxylic acid tert-butyl ester

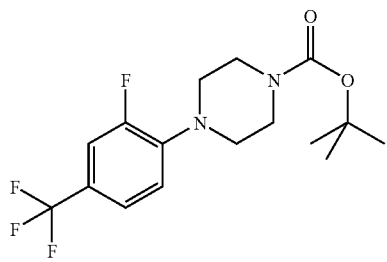

A mixture of 5 g (20 mmol) 1-Bromo-2-fluoro-4-trifluoromethyl-benzene, 4.6 g (24.7 mmol) n-Boc-piperazine, 106 mg (0.1 mmol) Tris(dibenzylideneacetone)dipalladium chloroform complex 2.77 g (28.8 mmol) sodium-t-butoxide and 144 mg (0.4 mmol) 2-(Dicyclohexylphosphino)biphenyl in 50 ml toluene was heated for 16 h at 80° C. After cooling to room temperature the mixture was treated with 15 g Isolute HM-N and all volatiles were removed under vacuum. The residue was purified on silica eluting with a gradient of heptane/EtOAc to yield after evaporation 4.54 g (63%) of the title compound as white amorphous solid; MS (m/e): 349.2 (MH$^+$, 100%).

EXAMPLE F 1-(2-Fluoro-4-trifluoromethyl-phenyl)-piperazine

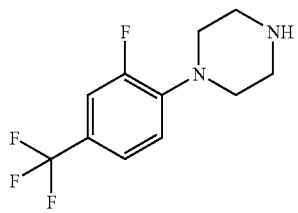

A mixture of 3.11 g (9 mmol) 4-(2-Fluoro-4-trifluoromethyl-phenyl)-piperazine-1-carboxylic acid tert-butyl ester in 20 ml dioxane was treated with 8.93 ml 4N HCl in dioxane for 2 h at 80° C. The mixture was concentrated and treated with 20 ml water, 20 ml 2M Na$_2$CO$_3$ and extracted with 50 ml EtOAc. The organic phase was washed with 30 ml saturated NaCl. All aqueous phases were combined and extracted with 50 ml EtOAc. The combined organic phases were dried with MgSO4 and evaporated to yield 2.1 g (95%) of the title compound as brownish crystals; MS (m/e): 249.2 (MH$^+$, 100%)

Procedure A: Suzuki-Miyaura Coupling

EXAMPLE G

2-Cyclohex-1-enyl-5-methanesulfonyl-benzoic acid

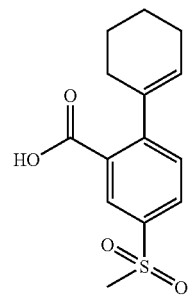

In analogy to a procedure described by Masuda et al. [M. Murata, T. Oyama, S. Watanabe, Y. Masuda, Synthesis 2000, 778] a stirred mixture of 1 eq. 2-cyclohex-1-enyl-4,4,5,5-tetramethyl-[1,3,2]dioxaborolane, 0.8 eq. 2-iodo-5-methanesulfonyl-benzoic acid, 2 eq. aqueous 3M KOH solution and 0.03 eq PdCl$_2$ (dppf)$_2$-CHCl$_3$ in dioxane (0.2 ml per mmol) were heated to 80° C. for 5 h. Then the reaction mixture is diluted with water, extracted with AcOEt, the aqueous phase acidified with 2N H$_2$SO$_4$, extracted with AcOEt and the pooled organic extracts dried over Na$_2$SO$_4$, filtered and evaporated. The crude product is purified by flash-chromatography on silica gel with heptane/AcOEt as eluent to yield the title compound; MS (ISN): 279.8 M−H$^-$.

EXAMPLE H

2-Cyclopent-1-enyl-5-methanesulfonyl-benzoic acid

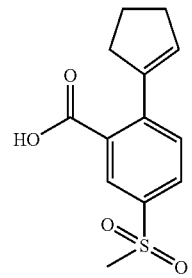

Following procedure A, 2-Cyclopent-1-enyl-5-methanesulfonyl-benzoic acid is prepared from 2-iodo-5-methanesulfonyl-benzoic acid and 2-cyclopent-1-enyl-4,4,5,5-tetramethyl-[1,3,2]dioxaborolane [M. Murata, T. Oyama, S. Watanabe, Y. Masuda, Synthesis 2000, 778]: MS (ISN): 264.8 M−H$^-$.

EXAMPLE I

2-Cyclohept-1-enyl-5-methanesulfonyl-benzoic acid

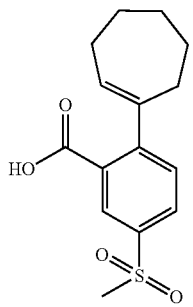

Following procedure A, 2-Cyclohept-1-enyl-5-methanesulfonyl-benzoic acid is prepared from 2-iodo-5-methanesulfonyl-benzoic acid and 2-cyclohept-1-enyl-4,4,5,5-tetramethyl-[1,3,2]dioxaborolane [M. Murata, T. Oyama, S. Watanabe, Y. Masuda, Synthesis 2000, 778]: MS (ISN): 292.9 M–H⁻.

EXAMPLE J 2-(3,6-Dihydro-2H-pyran-4-yl)-5-methanesulfonyl-benzoic acid

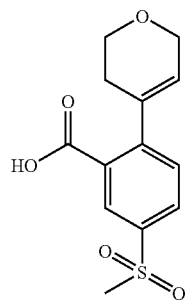

Following procedure A, 2-(3,6-Dihydro-2H-pyran-4-yl)-5-methanesulfonyl-benzoic acid is prepared from 2-iodo-5-methanesulfonyl-benzoic acid and 2-cyclohept-1-enyl-4,4,5,5-tetramethyl-[1,3,2]dioxaborolane [M. Murata, T. Oyama, S. Watanabe, Y. Masuda, Synthesis 2000, 778]: MS (ISN): 280.8 M–H⁻.

EXAMPLE K

5-Nitro-2-trifluoromethyl-benzoic acid

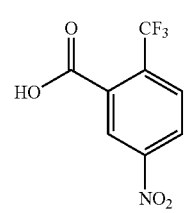

5-Nitro-2-trifluoromethyl-benzoic acid is prepared from the known 2-methyl-4-nitro-1-trifluoromethyl-benzene by oxidation with chromium trioxide in an acetic acid/water/ sulfuric acid mixture following a procedure described by Aeberli et al. [P. Aeberli, P. Eden, J. H. Gogerty, W. J. Houlihan, C. Penberthy, J. Med. Chem. 18, 177 (1975)]: colourless solid, MS (ISN): 233.9 M–H⁻.

EXAMPLE L

Procedure B : Sonoghashira Reaction:

(5-Methanesulfonyl-2-trimethylsilanylethynyl-phenyl)-[4-(4-trifluoromethyl-phenyl)-piperazin-1-yl]-methanone

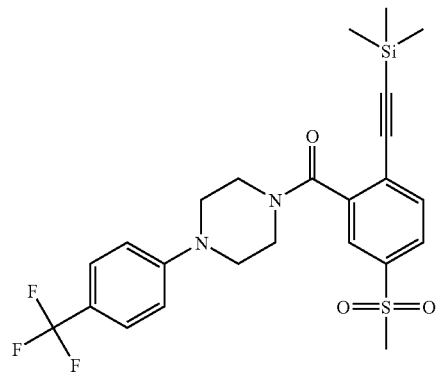

A mixture of (2-Iodo-5-methanesulfonyl-phenyl)-[4-(4-trifluoromethyl-phenyl)-piperazin-1-yl]-methanone, Example 9 (100 mg, 0.186 mmol), Pd(PPh3)4 (10 mg, 0.0093 mmol), CuI (1.8 mg, 0.0093 mmol) and Ethynyltrimethylsilane (32 ul, 0.223 mmol) in triethylamine (0.4 ml) was heated to 80° C. for 4 hours. The mixture was cooled to room temperature, diluted with ethylacetate, filtered and the solvent was removed in vacuo. The crude brown oil was purified on SiO2 (Heptane/AcOEt 0%-40%, 15 minutes) to provide the title compound (50 mg, 53%, yellow foam); M+H=590.2.

EXAMPLE M

4-Chloro-N-methyl-3-[4-(4-trifluoromethyl-phenyl)-piperazine-1-carbonyl]-benzenesulfonamide

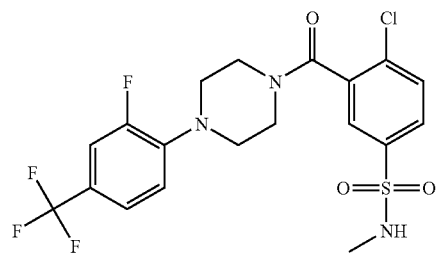

Following procedure E, the title compound was synthetised from 1-(4-trifluoromethyl-phenyl)-piperazine and 2-Chloro-5-(N-methylsulfamoyl)benzoic acid (CAS= [68901-09-7]); M–H=460.1

EXAMPLE N

[4-(2-Fluoro-4-trifluoromethyl-phenyl)-piperazin-1-yl]-(2-iodo-5-methanesulfonyl-phenyl)-methanone

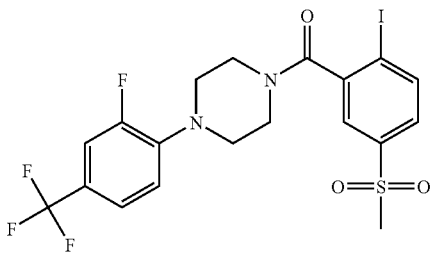

Following procedure E, the title compound was synthetised from 1-(2-Fluoro-4-trifluoromethyl-phenyl)-piperazine (Example F) and 2-Iodo-5-methanesulfonyl-benzoic acid (Example C); M+H=556.9.

EXAMPLE O

5-Methanesulfonyl-2-thiazol-2-yl-benzoic acid

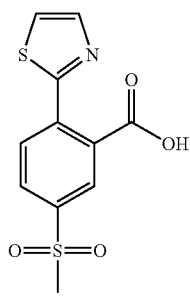

(a) 2-Iodo-5-methanesulfonyl-benzoic acid methyl ester

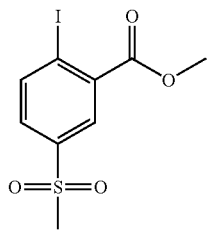

Following procedure D, 2-iodo-5-methanesulfonyl-benzoic acid methyl ester is prepared from 2-Iodo-5-methanesulfonyl-benzoic acid (example C) and Methanol. 86% Yield, white solid, MS (m/e): 357.8 (M+NH4+, 100%)

(b) 5-Methanesulfonyl-2-thiazol-2-yl-benzoic acid methyl ester

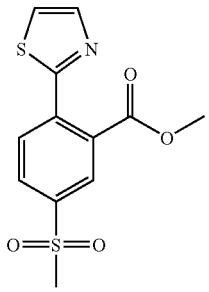

Following procedure I, 5-methanesulfonyl-2-thiazol-2-yl-benzoic acid methyl ester is prepared from 2-Iodo-5-methanesulfonyl-benzoic acid methyl ester and 2-Tributylstannanyl-thiazole (CAS: 121359-48-6). Colorless oil, 65% yield, MS (m/e): (MH+, 100%)

(c) 5-Methanesulfonyl-2-thiazol-2-yl-benzoic acid

5-Methanesulfonyl-2-thiazol-2-yl-benzoic acid is prepared by saponification of 5-Methanesulfonyl-2-thiazol-2-yl-benzoic acid methyl ester in the presence of sodium hydroxide (2N) in a mixture of dioxane and ethanol at 80 deg for 30 minutes. Brow solid, 50% yield, MS (m/e): 282.2 (M−H, 100%)

EXAMPLE P 1-(3-Fluoro-4-trifluoromethyl-phenyl)-piperazine

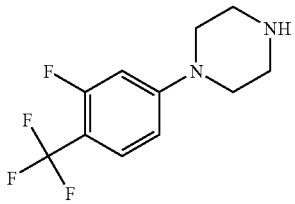

(a)-4-(3-Fluoro-4-trifluoromethyl-phenyl)-piperazine-1-carboxylic acid tert-butyl ester

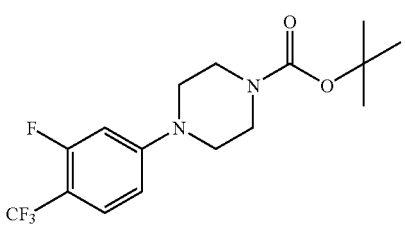

To a mixture of sodium tert-butoxide (0.68 g, 6.9 mmol), palladium(II)acetate (11 mg, 0.05 mmol), 2-(di-t-butylphosphino)biphenyl (149 mg, 0.49 mmol), tert-Butyl-1-piperazine carboxylate (1.1 g, 5.9 mmol) and 4-chloro-2-fluorobenzotrifluoride (1 g, 4.94 mmol) was added degazed toluene (10 ml). The mixture was heated to 80° C. overnight. The mixture was cool to room temperature, diluted with ether, filtered and the filtrate was concentrated in vacuo. The residue was chromatographed over silica gel: eluent: Heptane/Ethylacetate 0-10% over 15 minutes to provide the title compound (1.05 g, 61%) as a white solid, MS (m/e): 349.2 (M+H, 100%).

(b) 1-(3-Fluoro-4-trifluoromethyl-phenyl)-piperazine

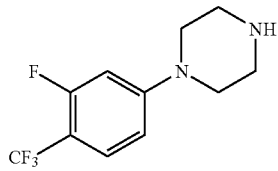

The title compound was prepared according to the procedure described for example F from 4-(3-Fluoro-4-trifluoromethyl-phenyl)-piperazine-1-carboxylic acid tert-butyl ester (98%, brown solid, MS (m/e): 249.2(M+H, 100%)

EXAMPLE Q 1-(3-Fluoro-4-trifluoromethyl-phenyl)-piperazine

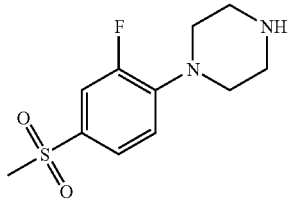

This compound is commercially available

EXAMPLE R

[4-(2-Fluoro-4-methanesulfonyl-phenyl)-piperazin-1-yl]-(2-iodo-5-methanesulfonyl-phenyl)-methanone

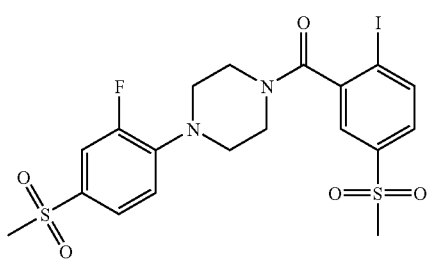

Following procedure E, the title compound was synthetised from 1-(2-Fluoro-4-methanesulfonyl-phenyl)-piperazine (Commercially available from Peakdale) and 2-Iodo-5-methanesulfonyl-benzoic acid (Example C); M+H=567.0 (100%)

EXAMPLE S

3-Fluoro-4-[4-(2-iodo-5-methanesulfonyl-benzoyl)-piperazin-1-yl]-benzonitrile

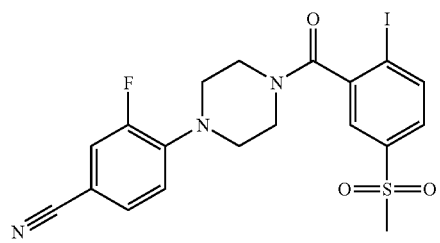

Following procedure E, the title compound was synthetised from 3-Fluoro-4-piperazin-1-yl-benzonitrile (WO9625414, [182181-38-0]) and 2-Iodo-5-methanesulfonyl-benzoic acid (Example C); M+H=514.0

EXAMPLE T (5-Methanesulfonyl-2-trimethylstannanyl-phenyl)-[4-(4-trifluoromethyl-phenyl)-piperazin-1-yl]-methanone

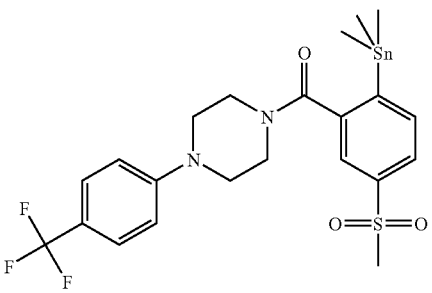

A mixture of (2-Iodo-5-methanesulfonyl-phenyl)-[4-(4-trifluoromethyl-phenyl)-piperazin-1-yl]-methanone (Example 9, 2.62 g, 4.87 mmol), Tetrakis(triphenylphosphine) palladium(0) (248 mg, 0.21 mmol), Palladium(II) acetate (77 mg, 0.34 mmol) and Hexamethyldistannane (1.72 ml, 8.27 mmol) in Tetrahydrofuran (15 ml) and Triethylamine (0.75 ml) was heated at 100° C. for 1 hour. The mixture was cooled to room temperature and concentrated in vacuo. The residue was chromatographed over SiO₂ (ethyl acetate/heptane/triethylamine 0/98/2 to 18/80/2) to provide the title compound (990 mg, 35%) as an off-white solid.

EXAMPLE U

2-Iodo-5-methyl-thiazole

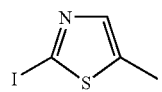

To a solution of Diisopropylamine (6.78 ml, 21.7 mmol) in Tetrahydrofuran (50 ml) was added dropwise a 2 M solution of Butylmagnesium chloride in Tetrahydrofuran (9.83 ml, 19.7 mmol) and the mixture was stirred at room temperature for 16 hours. 5-Methylthiazole (1.00 g, 10.1 mmol) was then added and stirring continued for a further hour, whereupon a solution of Iodine (6.53 g, 25.7 mmol) in Tetrahydrofuran (50 ml) was added dropwise. After stirring for a further 1 hour, the reaction mixture was quenched with aqueous sodium thiosulphate solution (20%, 100 ml) and extracted three times with Ethyl acetate. The combined organic phases were dried over $Na_2SO_4$ and concentrated in vacuo. The residue was chromatographed over $SiO_2$ (ethyl acetate/heptane 1/1) to provide the title compound (1.95 g, 86%) as brown oil.

EXAMPLE V

4-Methanesulfonyl-biphenyl-2-carboxylic acid

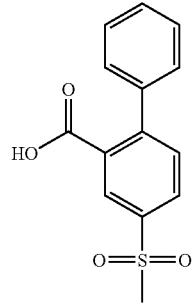

(a) 2-Iodo-5-methanesulfonyl-benzoic acid methyl ester

To 2-Iodo-5-methanesulfonyl-benzoic acid (Example C, 10.0 g, 30.7 mmol in 250 ml THF was added CDI (5.50 g, 33.7 mmol) and the mixture heated at 70° C. for 1 h. Methanol (12.4 ml, 307 mmol) was then added and the mixture was heated at 70° C. for a further 1 h. The mixture was then cooled to room temperature and concentrated in vacuo. The residue was chromatographed over $SiO_2$ (ethyl acetate/dichloromethane 4:1) to afford the title compound (8.95 g, 86%) as white crystalline solid.

(b) 4-Methanesulfonyl-biphenyl-2-carboxylic acid methyl ester

A mixture of 2-Iodo-5-methanesulfonyl-benzoic acid methyl ester (1.20 g, 3.53 mmol), Phenyltri-n-butyltin (1.27 ml, 3.88 mmol), Tris(dibenzylideneacetone) dipalladium(0) (226 mg, 0.25 mmol), Triphenylarsine (108 mg, 0.35 mmol) and Copper iodide (309 mg, 1.62 mmol) in N,N-Dimethylformamide (30 ml) was heated at 90° C. for 16 hours. The mixture was cooled to room temperature and concentrated in vacuo. The residue was chromatographed over $SiO_2$ (ethyl acetate/heptane gradient) to provide the title compound (1.02 g, 99%) as an off-white crystalline solid. MS (ISP): 291.0 $MH^+$.

(c) 4-Methanesulfonyl-biphenyl-2-carboxylic acid

To 4-Methanesulfonyl-biphenyl-2-carboxylic acid methyl ester (1.00 g, 3.44 mmol) in 5 ml THF was added 5 M aq NaOH solution (7.58 ml, 37.9 mmol) and the mixture was heated at 60° C. for 16 h. The mixture was then cooled to RT, acidified to pH 1 with conc hydrochloric acid, and extracted 3 times with ethyl acetate. The combined organic phases were dried with $Na_2SO_4$. Evaporation in vacuo afforded the title compound (903 mg, 95%) as an off-white crystalline solid. MS (ISN): 275.1 $M-H^-$.

EXAMPLE W 1-(4-Cyclopropanesulfonyl-2-fluoro-phenyl)-piperazine

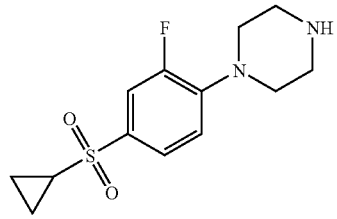

(a) 3,4-Difluoro-benzenesulfinic acid

To sodium sulfite (22.2 g, 176 mmol) in 80 ml water at RT was added dropwise over 20 min a solution of 3,4-difluoro-benzenesulfonyl chloride (5.00 g, 23.5 mmol) in 40 ml dioxane. 1 M aq NaOH (40 ml) was then added dropwise until the reaction mixture was pH 14 and the mixture was then allowed to stir at RT for a further 16 h. The mixture was then cooled to 0° C. and concentrated $H_2SO_4$ added until the reaction mixture was pH 1. The mixture was extracted three times with ethyl acetate and the combined organic phases washed with saturated aq NaCl solution and then dried with $Na_2SO_4$. Evaporation in vacuo yielded the title compound (4.21 g, 97%) as a white crystalline solid. MS (ISN): 177.1 $M-H^-$

(b) 4-(3-Chloro-propane-1-sulfonyl)-1,2-difluoro-benzene

To 3,4-difluoro-benzenesulfinic acid (500 mg, 2.81 mmol) and triethylamine (0.43 ml, 3.10 mmol) in 10 ml DMF was added 1-chloro-3-iodopropane (1.43 g, 7.00 mmol) and the mixture heated at 65° C. for 3 h. The reaction mixture was then poured onto water and extracted three times with ethyl acetate. The combined organic phases were then washed with saturated aq. NaCl solution, dried over $Na_2SO_4$, and concentrated in vacuo. The residue was chromatographed over $SiO_2$ (ethyl acetate/heptane 1:50) to afford the title compound (300 mg, 42%) as an off-white crystalline solid. MS (ISP): 257.2 $\{^{37}Cl\}MH^+$, 255.1 $\{^{35}Cl\}MH^+$

(c) 4-Cyclopropanesulfonyl-1,2-difluoro-benzene

To mmol 4-(3-chloro-propane-1-sulfonyl)-1,2-difluoro-benzene (300 mg, 1.18 mmol) in 10 ml THF at −78° C. was added dropwise a 0.9 M solution of potassium bis(trimethylsilyl)amide in THF (3.65 ml, 3.32 mmol). The reaction mixture was then allowed to warm to RT and stirring continued for a further 30 min at RT. The mixture was quenched by addition of 1 M aq HCl (2 ml) and water (10 ml), and then extracted three times with ethyl acetate. The combined organic phases were dried with $Na_2SO_4$, and concentrated in vacuo. The residue was chromatographed over $SiO_2$ (ethyl acetate/heptane 1:10) to afford the title compound (90 mg, 37%) as an off-white amorphous solid. MS (ISP): 219.2 $MH^+$

(d) 1-(4-Cyclopropanesulfonyl-2-fluoro-phenyl)-piperazine

To 4-cyclopropanesulfonyl-1,2-difluoro-benzene (40 mg, 0.18 mmol) in 5 ml N,N-dimethylacetamide was added piperazine (47 mg, 0.55 mmol) and the mixture was heated at 80° C. for 90 min. The mixture was then concentrated in vacuo to afford the tide compound (27 mg, 52%) as a brown solid. MS (ISP): 285.0 MH+

EXAMPLE X

Dimethyl-(4-piperazin-1-yl-[1,3,5]triazin-2-yl)-amine

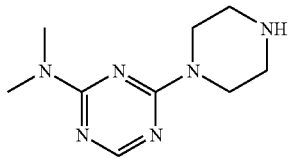

(a) 4-(4-Chloro-[1,3,5]triazin-2-yl)-piperazine-1-carboxylic acid tert-butyl ester A solution of 11 mmol of 2,4-dichlorotriazine (WO 02/083654) in 20 ml of acetonitrile was chilled and treated with 11 mmol of triethylamine and 11 mmol of N-BOC-piperazine. The reaction mixture was stirred for 2 hours at 0° C. then for 2 hours at room temperature. Addition of 100 ml brine and extraction with ethyl acetate yields the crude product which was purified through trituration in ethyl acetate. MS (m/e): 300.3 (MH+, 100%)

(b) 4-(4-Dimethylamino-[1,3,5]triazin-2-yl)-piperazine-1-carboxylic acid tert-butyl ester A solution of 2 mmol of 4-(4-Chloro-[1,3,5]triazin-2-yl)-piperazine-1-carboxylic acid tert-butyl ester in 15 ml of 2M dimethylamine in methanol was stirred at room temperature for 1 hour. Concentration and purification by chromatography (SiO2; ethyl acetate/cyclohexane 1:1) yields the title compound as a colorless solid. MS (m/e): 309.1 (MH+, 100%)

(c) Dimethyl-(4-piperazin-1-yl-[1,3,5]triazin-2-yl)-amine

A solution of 1 mmol of 4-(4-Dimethylamino-[1,3,5]triazin-2-yl)-piperazine-1-carboxylic acid tert-butyl ester in 10 ml dichloromethane was chilled and treated with 14 mmol of trifluoroacetic acid. The reaction mixture was heated to 40° C. for 30 min. After cooling, 50 ml of 2M aqueous sodium hydroxide is added. The organic layer is separated, dried and concentrated to yield the title compound as a yellowish oil. MS (m/e): 267.0 (M+CH3COO+, 100%)

EXAMPLE Y

[4-(3-Chloro-5-trifluoromethyl-pyridin-2-yl)-piperazin-1-yl]-(2-iodo-5-methanesulfonyl-phenyl)-methanone

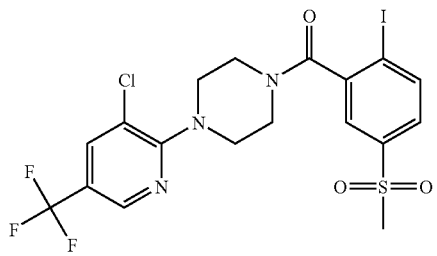

Following procedure E, the title compound was synthetised from 1-(3-Chloro-5-trifluoromethyl-pyridin-2-yl)-piperazine ([132834-59-4]) and 2-Iodo-5-methanesulfonyl-benzoic acid (Example C); M+H=574

EXAMPLE Z

[4-(2-Fluoro-phenyl)-piperazin-1-yl]-(2-iodo-5-methanesulfonyl-phenyl)-methanone

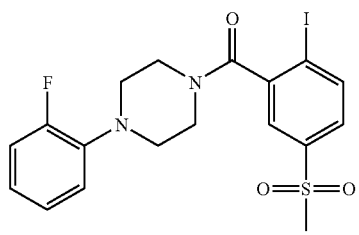

Following procedure E, the title compound was synthetised from 1-(2-Fluorophenyl)piperazine ([1011-15-0]) and 2-Iodo-5-methanesulfonyl-benzoic acid (Example C); M+H=489

EXAMPLE AA

1-{3-Fluoro-4-[4-(2-iodo-5-methanesulfonyl-benzoyl)-piperazin-1-yl]-phenyl}-ethanone

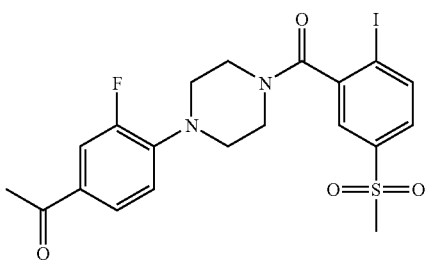

Following procedure E, the title compound was synthetised from 1-(3-Fluoro-4-piperazin-1-yl-phenyl)-ethanone [189763-57-3] and 2-Iodo-5-methanesulfonyl-benzoic acid (Example C); M+H=531

EXAMPLE AB

3-Fluoro-4-[4-(2-iodo-5-methanesulfonyl-benzoyl)-piperazin-1-yl]-benzonitrile

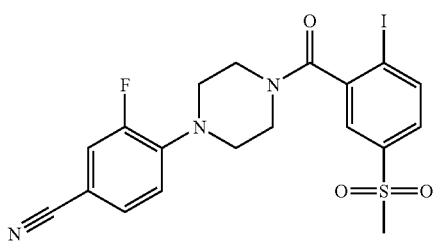

Following procedure E, the title compound was synthetised from 3-Fluoro-4-piperazin-1-yl-benzonitrile [182181-38-0] and 2-Iodo-5-methanesulfonyl-benzoic acid (Example C); M+H=514

EXAMPLE AC

1-{4-[4-(2-Iodo-5-methanesulfonyl-benzoyl)-piperazin-1-yl]-phenyl}-ethanone

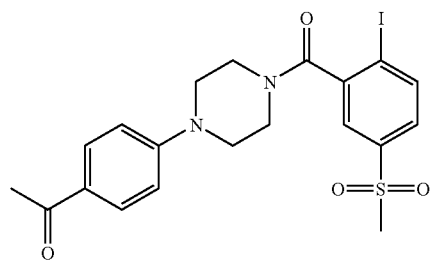

Following procedure E, the title compound was synthetised from 1-(4-Piperazin-1-yl-phenyl)-ethanone [51639-48-6] and 2-Iodo-5-methanesulfonyl-benzoic acid (Example C); M+H=513

EXAMPLE AD

[4-(2,4-Difluoro-phenyl)-piperazin-1-yl]-(2-iodo-5-methanesulfonyl-phenyl)-methanone

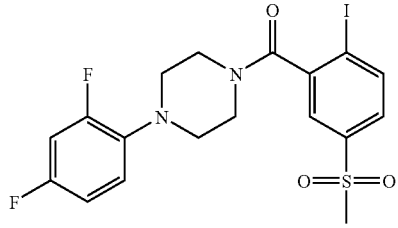

Following procedure E, the title compound was synthetised from 1-(2,4-Difluoro-phenyl)-piperazine [115761-79-0] and 2-Iodo-5-methanesulfonyl-benzoic acid (Example C); M+H =507

EXAMPLE AE

2-Piperazin-1-yl-5-trifluoromethyl-pyrimidine

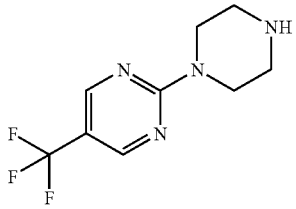

(a) 2-(4-Benzyl-piperazin-1-yl)-5-trifluoromethyl-pyrimidine

To a solution of (3-Dimethylamino-2-trifluoromethyl-allylidene)-dimethyl-ammonium chloride ([176214-18-9], 0.60 g) in acetonitrile (10 mL) was added 4-Benzyl-piperazine-1-carboxamidine hydrochloride ([7773-69-5], 0.66 g) and triethylamine (0.87 mL) and the reaction mixture was stirred for 3 hours at room temperature. After such time the reaction mixture was concentrated in vacuo and purified by column chromatography to yield the title compound as a light yellow solid (0.79 g). MS (m/e): 323.4 (M+H$^+$).

(b) 2-Piperazin-1-yl-5-trifluoromethyl-pyrimidine

To a solution of 2-(4-Benzyl-piperazin-1-yl)-5-trifluoromethyl-pyrimidine (0.63 g) in methanol was added Palladium-C (Degussa E101N; 5%) and the reaction mixture was heated at 60° C. under hydrogen atmosphere. The reaction mixture was then allowed to cool down to room temperature, the catalyst was filtered of and solvent was removed in vacuo to yield the title compound as a colorless solid (0.41 g). MS (m/e): 233.1 (M+H$^+$).

EXAMPLE AF

2-[4-(2-Iodo-5-methanesulfonyl-benzoyl)-piperazin-1-yl]-benzonitrile

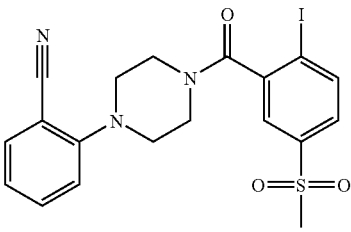

Following procedure E, the title compound was synthetised from 2-Piperazin-1-yl-benzonitrile [111373-03-6] and 2-Iodo-5-methanesulfonyl-benzoic acid (Example C); M+H=496

EXAMPLE AG

4-[4-(2-Iodo-5-methanesulfonyl-benzoyl)-piperazin-1-yl]-benzonitrile

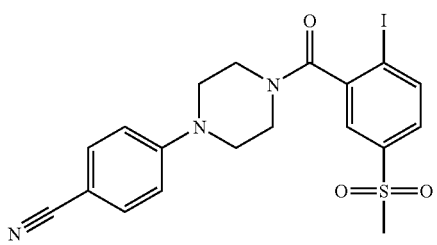

Following procedure E, the title compound was synthetised from 4-Piperazin-1-yl-benzonitrile [68104-63-2] and 2-Iodo-5-methanesulfonyl-benzoic acid (Example C); M+H=496

EXAMPLE 1

1-(4-acetyl-2-fluoro-5-methylphenyl)-4-(2-fluoro-5-nitrobenzoyl)-piperazine

Known compound, CAS number: [313377-35-4]
Procedure C

EXAMPLE 2

1-{3-Fluoro-4-[4-(2-fluoro-5-nitro-benzoyl)-piperazin-1-yl]-phenyl}-ethanone

A solution of 2-Fluoro-5-nitro-benzoyl chloride (CAS: 7304-32-7; Feng, Y.; Burgess, K.; Chem.Europ.J.; EN; 5; 11; 1999; 3261-3272) (0.054 g, 0.261 mmol) in dioxane (1 ml) was treated with triethylamine (0.073 ml, 0.522 mmol) and then with a solution of 1-(3-Fluoro-4-piperazin-1-yl-phenyl)-ethanone (CAS: 189763-57-3; WO9714690) (58 mg, 0.261 mmol) in dioxane (1 ml). The mixture was stirred at room temperature for 30 minutes. The solvent was removed in vacuo. The crude oil was taken in water. The aqueous layer was extracted 3 times with $CH_2Cl_2$. The combined extracts were dried over $Na_2SO_4$, filtered and the solvent was removed in vacuo. The crude gum was purified on a SiO2 (Heptane/AcOEt 0%-20% (10 minutes, then 20% (5 minutes) to provide 1-{3-Fluoro-4-[4-(2-fluoro-5-nitro-benzoyl)-piperazin-1-yl]-phenyl}-ethanone (69 mg, 68%) as a light yellow solid (M+H+: 390.2).
Procedure D

EXAMPLE 3

3-[4-(4-acetyl-2-fluoro-phenyl)-piperazine-1-carbonyl]-4-bromo benzonitrile

To a solution of 2-bromo-5-cyano-benzoic acid (200 mg, 0.885 mmol) in DMF (3 ml) was added dropwise 1,1'-Carbonyldiimidazole (148 mg, 0.885 mmol). When the CO2 evolution ceased, the mixture was heated to 50° C. for 15 minutes. The mixture was cooled to room temperature. 1-(3-Fluoro-4-piperazin-1-yl-phenyl)-ethanone (198 mg, 0.885 mmol) was added portionwise. The mixture was stirred at room temperature for 1 hour. The solvent was removed in vacuo. The residue was dissolved in ethyl acetate. The solution was washed twice with water, dried over $Na_2SO_4$, filtered and the solvent was removed in vacuo. The crude oil was purified on $SiO_2$ (Heptane/AcOEt 0%-30% (10 minutes)) to provide 3-[4-(4-acetyl-2-fluoro-phenyl)-piperazine-1-carbonyl]-4-bromo benzonitrile (185 mg, 49%) as white solid (M+ 430.3).

EXAMPLE 4

1-{4-[4-(2-Bromo-5-nitro-benzoyl)-piperazin-1-yl]-3-fluoro-phenyl}-ethanone

The title compound was prepared according to the procedure C described for example 2 from 1-(3-fluoro-4-piperazin-1-yl-phenyl)-ethanone and 2-bromo-5-nitro-benzoyl chloride (CAS: 80887-01-0; Grohmann, Chem.Ber.; 24; 1891; 3814) (81% yield, yellow solid, M+: 450.0)

EXAMPLE 5

1-{4-[4-(2-Chloro-5-methanesulfonyl-benzoyl)-piperazin-1-yl]-3-fluoro-phenyl}-ethanone The title compound was prepared according to the procedure D described for example 2 from 1-(3-Fluoro-4-piperazin-1-yl-phenyl)-ethanone and 2-chloro-5-methanesulfonyl-benzoic acid (Example B), 72%, white solid, M+H+: 439.1)

EXAMPLE 6

3-[4-(4-Acetyl-2-fluoro-phenyl)-piperazine-1-carbonyl]-4-chloro-benzenesulfonamide The title compound was prepared according to the procedure D described for example 2 from 1-(3-Fluoro-4-piperazin-1-yl-phenyl)-ethanone and 2-Chloro-5-sulfamoyl-benzoic acid (CAS: 97-04-1; Basu; D.-G.; J. Indian Chem. Soc.; 16; 1939; 100, 106) (42%, white solid, M−H: 438.1)

EXAMPLE 7

3-[4-(4-Acetyl-2-fluoro-phenyl)-piperazine-1-carbonyl]-4-chloro-N-methyl-benzenesulfonamide The title compound was prepared according to the procedure D described for example 2 from 1-(3-Fluoro-4-piperazin-1-yl-phenyl)-ethanone and 2-Chloro-5-methylsulfamoyl-benzoic acid (CAS: 68901-09-7; BE 620741) (69%, light yellow foam, M−H: 452.1)

EXAMPLE 8

1-{4-[4-(2-Chloro-5-nitro-benzoyl)-piperazin-1-yl]-3-fluoro-phenyl}-ethanone

The title compound was prepared according to the procedure D described for example 2 from 1-(3-Fluoro-4-piperazin-1-yl-phenyl)-ethanone and 2-chloro-5-nitro-benzoic acid (CAS: 2516-96-3); MS (ISP): 406.2 MH+.

Procedure E

EXAMPLE 9

(2-Iodo-5-methanesulfonyl-phenyl)-[4-(4-trifluoromethyl-phenyl)-piperazin-1-yl]-methanone To a solution of 2-Iodo-5-methanesulfonyl-benzoic acid (Example C, 3.0 g, 9.2 mmol) in dimethylformamide (20 ml) were successively added TBTU (3.8 g, 11.5 mmol), N-ethyldiisopropylamine (8.0 ml, 46.0 mmol) and 1-(4-trifluromethylphenyl)piperazine (ABCR F07741NB, [30459-17-7], 2.5 g, 11.0 mmol). The reaction was then stirred at room temperature for two hours, then concentrated in vacuo and purified by column chromatography (SiO2, 50 g, $CH_2Cl_2$/MeOH/NH3=100/0/0 to 95/4.5/0.5), to give the title compound as a pale brown foam; MS (m/e): 539.1 (M+H$^+$). TBTU=2-(1H-benzotriazole-1-yl)-1,1,3,3-tetramethyluronium tetrafluoroborate

EXAMPLE 10

(2-Chloro-5-methanesulfonyl-phenyl)-[4-(4-trifluoromethyl-phenyl)-piperazin-1-yl]-methanone The title compound was prepared according to the procedure E described for example 9 from 1-(4-trifluromethylphenyl)piperazine (ABCR F07741NB, [30459-17-7] and 2-chloro-5-(methylsulfonyl)-benzoic acid (CAS: 89938-62-5); MS (m/e): 464.3 (M+NH$_4^+$).

EXAMPLE 11

1-{4-[4-(2-Chloro-5-tetrazol-1-yl-benzoyl)-piperazin-1-yl]-3-fluoro-phenyl}-ethanone The title compound was prepared according to the procedure E described for example 2 from 1-(3-Fluoro-4-piperazin-1-yl-phenyl)-ethanone and 2-Chloro-5-tetrazol-1-yl-benzoic acid (CAS: 190270-10-1; commercial) (50%, white solid, M+H: 429.2)

EXAMPLE 12

1-{4-[4-(2,6-Dichloro-3-nitro-benzoyl)-piperazin-1-yl]-3-fluoro-phenyl}-ethanone The title compound was prepared according to the procedure E described for Example 9 from 2,6-dichloro-3-nitrobenzoic acid (CAS: 55775-97-8; commercial) and 1-(3-fluoro-4-piperazin-1-yl-phenyl)-ethanone: colourless solid, m.p. 209-211° C., MS (ISP): 440.1 MH$^+$.

EXAMPLE 82

2-Fluoro-4-[4-(5-methanesulfonyl-2-thiazol-2-yl-benzoyl)-piperazin-1-yl]-benzonitrile The title compound was prepared according to the procedure E described for Example 9 from 2-Fluoro-4-piperazin-1-yl-benzonitrile [204192-45-0] and 5-Methanesulfonyl-2-thiazol-2-yl-benzoic acid (Example O). MS (ISP): 471.0 MH$^+$.

EXAMPLE 83

4-[4-(5-Methanesulfonyl-2-thiazol-2-yl-benzoyl)-piperazin-1-yl]-benzonitrile

The title compound was prepared according to the procedure E described for Example 9 from 4-piperazin-1-yl-benzonitrile [68104-63-2] and 5-Methanesulfonyl-2-thiazol-2-yl-benzoic acid (Example O). MS (ISP): 453.5 MH$^+$.

EXAMPLE 84

3-Fluoro-4-[4-(5-methanesulfonyl-2-thiazol-2-yl-benzoyl)-piperazin-1-yl]-benzonitrile The title compound was prepared according to the procedure E described for Example 9 from 3-Fluoro-4-piperazin-1-yl-benzonitrile [182181-38-0] and 5-Methanesulfonyl-2-thiazol-2-yl-benzoic acid (Example O). MS (ISP): 471.4 MH$^+$.

EXAMPLE 85

1-{3-Fluoro-4-[4-(5-methanesulfonyl-2-thiazol-2-yl-benzoyl)-piperazin-1-yl]-phenyl}-ethanone The title compound was prepared according to the procedure E described for Example 9 from 1-(3-Fluoro-4-piperazin-1-yl-phenyl)-ethanone [189763-57-3] and 5-Methanesulfonyl-2-thiazol-2-yl-benzoic acid (Example O). MS (ISP): 488.5 MH$^+$.

EXAMPLE 86

[4-(3-Fluoro-4-trifluoromethyl-phenyl)-piperazin-1-yl]-(5-methanesulfonyl-2-thiazol-2-yl-phenyl)-methanone The title compound was prepared according to the procedure E described for Example 9 from 1-(3-Fluoro-4-trifluoromethyl-phenyl)-piperazine (Example P) and 5-Methanesulfonyl-2-thiazol-2-yl-benzoic acid (Example O). MS (ISP): 514.5 MH$^+$.

EXAMPLE 87

[4-(2-Fluoro-4-trifluoromethyl-phenyl)-piperazin-1-yl]-(5-methanesulfonyl-2-thiazol-2-yl-phenyl)-methanone The title compound was prepared according to the procedure E described for Example 9 from 1-(2-Fluoro-4-trifluoromethyl-phenyl)-piperazine (Example F) and 5-Methanesulfonyl-2-thiazol-2-yl-benzoic acid (Example O). MS (ISP): 514.3 MH$^+$.

EXAMPLE 88

[4-(2-Fluoro-4-methanesulfonyl-phenyl)-piperazin-1-yl]-(5-methanesulfonyl-2-thiazol-2-yl-phenyl)-methanone The title compound was prepared according to the procedure E described for Example 9 from 1-(2-Fluoro-4-methanesulfonyl-phenyl)-piperazine (Example Q) and 5-Methanesulfonyl-2-thiazol-2-yl-benzoic acid (Example O). MS (ISP): 524.3 MH$^+$.

EXAMPLE 98

(4-Methanesulfonyl-biphenyl-2-yl)-(4-phenyl-piperazin-1-yl)-methanone

The title compound was prepared according to the procedure E described for Example 9 from phenyl piperazine [189457-54-3] and 4-Methanesulfonyl-biphenyl-2-carboxylic acid (Example V). MS (ISP): 421.3 MH+.

EXAMPLE 99

[4-(4-Hydroxy-phenyl)-piperazin-1-yl]-(4-methanesulfonyl-biphenyl-2-yl)-methanone The title compound was prepared according to the procedure E described for Example 9 from '1-(4-hydroxyphenyl)-piperazine [56621-48-8] and 4-Methanesulfonyl-biphenyl-2-carboxylic acid (Example V). MS (ISP): 437.4 MH+.

EXAMPLE 100

(4-Methanesulfonyl-biphenyl-2-yl)-[4-(4-methoxy-phenyl)-piperazin-1-yl]-methanone The title compound was prepared according to the procedure E described for Example 9 from '1-(4-metoxyphenyl)-piperazine [38212-30-5] and 4-Methanesulfonyl-biphenyl-2-carboxylic acid (Example V). MS (ISP): 451.1 MH+.

EXAMPLE 101

(4-Methanesulfonyl-biphenyl-2-yl)-[4-(4-trifluoromethyl-pyrimidin-2-yl)-piperazin-1-yl]-methanone The title compound was prepared according to the procedure E described for Example 9 from 2-Piperazin-1-yl-4-trifluoromethyl-pyrimidine [179756-91-3] and 4-Methanesulfonyl-biphenyl-2-carboxylic acid (Example V). MS (ISP): 491.1 MH+.

EXAMPLE 102

[4-(4-Cyclopropanesulfonyl-2-fluoro-phenyl)-piperazin-1-yl]-(4-methanesulfonyl-biphenyl-2-yl)-methanone The title compound was prepared according to the procedure E described for Example 9 from 1-(4-Cyclopropanesulfonyl-2-fluoro-phenyl)-piperazine (Example W) and 4-Methanesulfonyl-biphenyl-2-carboxylic acid (Example V). MS (ISP): 543.3 MH+.

EXAMPLE 103

(4-Methanesulfonyl-biphenyl-2-yl)-[4-(4-trifluoromethoxy-phenyl)-piperazin-1-yl]-methanone The title compound was prepared according to the procedure E described for Example 9 from 1-(4-Trifluoromethoxyphenyl)-piperazine [187669-62-1] and 4-Methanesulfonyl-biphenyl-2-carboxylic acid (Example V). MS (ISP): 505.4 MH+.

EXAMPLE 104

[4-(4-Dimethylamino-phenyl)-piperazin-1-yl]-(4-methanesulfonyl-biphenyl-2-yl)-methanone The tide compound was prepared according to the procedure E described for Example 9 from Dimethyl-(4-piperazin-1-yl-phenyl)-amine [91703-23-0] and 4-Methanesulfonyl-biphenyl-2-carboxylic acid (Example V). MS (ISP): 464.3 MH+.

EXAMPLE 105

[4-(4-Dimethylamino-[1,3,5]triazin-2-yl)-piperazin-1-yl]-(4-methanesulfonyl-biphenyl-2-yl)-methanone The title compound was prepared according to the procedure E described for Example 9 from Dimethyl-(4-piperazin-1-yl-[1,3,5]triazin-2-yl)-amine (Example X) and 4-Methanesulfonyl-biphenyl-2-carboxylic acid (Example V). MS (ISP): 467.4 MH+.

EXAMPLE 106

(4-Methanesulfonyl-biphenyl-2-yl)-[4-(4-methoxy-[1,3,5]triazin-2-yl)-piperazin-1-yl]-methanone The tide compound was prepared according to the procedure E described for Example 9 from 2-Methoxy-4-piperazin-1-yl-[1,3,5]triazine [59215-45-1] and 4-Methanesulfonyl-biphenyl-2-carboxylic acid (Example V). MS (ISP): 454.5 MH+.

EXAMPLE 108

[4-(2-Fluoro-4-trifluoromethyl-phenyl)-piperazin-1-yl]-(2-iodo-5-methanesulfonyl-phenyl)-methanone The title compound was prepared according to the procedure E described for Example 9 from 1-(2-Fluoro-4-trifluoromethyl-phenyl)-piperazine (Example F) and 2-Iodo-5-methanesulfonyl-benzoic acid (Example F). MS (ISP): 556.9 MH+.

EXAMPLE 134

(4-Methanesulfonyl-biphenyl-2-yl)-[4-(5-trifluoromethyl-pyrimidin-2-yl)-piperazin-1-yl]-methanone The title compound was prepared according to the procedure E described for Example 9 from 2-Piperazin-1-yl-5-trifluoromethyl-pyrimidine (Example AE) and 4-Methanesulfonyl-biphenyl-2-carboxylic acid (Example V). MS (ISP): 431.1 MH+.

Procedure F

EXAMPLE 13 rac-(2-Iodo-5-methanesulfonyl-phenyl)-[3-methyl-4-(4-trifluoromethyl-phenyl)-piperazin-1-yl]-methanone To a solution of rac-3-Methyl-4-(4-trifluoromethyl-phenyl)-piperazine-1-carboxylic acid tert-butyl ester (Example D, 95 mg, 0.27 mmol) in dichloromethane (2 ml) was added trifluoroacetic acid (1 ml) and the reaction mixture was stirred at room temperature for 30 min. After such time the reaction mixture was concentrated in vacuo, and the residue was dissolved in dimethylformamide (3 ml). To the solution were added 2-Iodo-5-methanesulfonyl-benzoic acid (Example C, 81 mg, 0.25 mmol), N-ethyldiisopropylamine (0.29 ml, 1.7 mmol), and TBTU (99 mg, 0.3 mmol). The reaction mixture was then allowed to stir at room temperature for 2 hours. The reaction mixture was then concentrated in vacuo and the residue was purified by column chromatography ($SiO_2$, 20 g, Heptane/EtOAc 0-100%) to give the title compound as a light brown solid (135 mg); MS (m/e): 553.1 ($M+H^+$).

TBTU=2-(1H-benzotriazole-1-yl)-1,1,3,3-tetramethyluronium tetrafluoroborate

Procedure G: Suzuki coupling.

EXAMPLE 17

(4-Methanesulfonyl-biphenyl-2-yl)-[4-(4-trifluoromethyl-phenyl)-piperazin-1-yl]-methanone To a solution of (2-Iodo-5-methanesulfonyl-phenyl)-[4-(4-trifluoromethyl-phenyl)-piperazin-1-yl]-methanone (Example 13; 70 mg, 0.130 mmol) in dioxane (2 ml) was added phenylboronic acid (31 mg, 0.260 mmol) followed by cesium carbonate (85 mg) and tetrakis(triphenylphosphine) palladium (0). The reaction mixture was then stirred for 24 hours at 100° C. The reaction mixture was then filtered over celite and concentrated in vacuo and the residue was purified by preparative HPLC (MeCN, H20+0.005 N HCOOH).

According to the above procedure G described for the synthesis of Example 17, further derivatives have been synthesized from (2-Iodo-5-methanesulfonyl-phenyl)-[4-(4-trifluoromethyl-phenyl)-piperazin-1-yl]-methanone (Example 9) and boronic acid or esters and comprise Examples 17-27, 38-42, 45-55, 65 and 107 in (Table 2).

According to the above procedure G described for the synthesis of Example 17, further derivatives have been synthesized from 1-{4-[4-(2-Bromo-5-nitro-benzoyl)-piperazin-1-yl]-3-fluoro-phenyl}-ethanone and trimethylboroxine (Example 14) or phenyl boronic acid (Example 15) (table 2).

According to the above procedure G described for the synthesis of Example 17, further derivatives have been synthesized from [4-(2-Fluoro-4-trifluoromethyl-phenyl)-piperazin-1-yl]-(2-iodo-5-methanesulfonyl-phenyl)-methanone (Example N) and boronic acids (Example 62-64).

According to the above procedure G described for the synthesis of Example 17, further derivatives have been synthesized from [4-(3-Chloro-5-trifluoromethyl-pyridin-2-yl)-piperazin-1-yl]-(2-iodo-5-methanesulfonyl-phenyl)-methanone (Example Y ) and boronic acid or esters and comprise Examples 108-116 in (Table 2).

According to the above procedure G described for the synthesis of Example 17, further derivatives have been synthesized from [4-(2-Fluoro-phenyl)-piperazin-1-yl]-(2-iodo-5-methanesulfonyl-phenyl)-methanone (Example Z ) and boronic acid or esters and comprise Examples 117-121 in (Table 2).

According to the above procedure G described for the synthesis of Example 17, further derivatives have been synthesized from 1-{3-Fluoro-4-[4-(2-iodo-5-methanesulfonyl-benzoyl)-piperazin-1-yl]-phenyl}-ethanone (Example AA ) and boronic acid or esters and comprise Examples 122-124 in (Table 2).

According to the above procedure G described for the synthesis of Example 17, further derivatives have been synthesized from 3-Fluoro-4-[4-(2-iodo-5-methanesulfonyl-benzoyl)-piperazin-1-yl]-benzonitrile (Example AB) and boronic acid or esters and comprise Examples 125 and 126 in (Table 2).

According to the above procedure G described for the synthesis of Example 17, further derivatives have been synthesized from 1-{4-[4-(2-Iodo-5-methanesulfonyl-benzoyl)-piperazin-1-yl]-phenyl}-ethanone (Example AC) and boronic acid or esters and comprise Example 127 in (Table 2).

According to the above procedure G described for the synthesis of Example 17, further derivatives have been synthesized from [4-(2,4-Difluoro-phenyl)-piperazin-1-yl]-(2-iodo-5-methanesulfonyl-phenyl)-methanone (Example AD ) and boronic acid or esters and comprise Examples 128-133 in (Table 2).

According to the above procedure G described for the synthesis of Example 17, further derivatives have been synthesized from 2-[4-(2-Iodo-5-methanesulfonyl-benzoyl)-piperazin-1-yl]-benzonitrile (Example AF) and boronic acid or esters and comprise Examples 135-138 in (Table 2).

Procedure H: Leadbeater Suzuki Variation

EXAMPLE 29

1-{3-Fluoro-4-[4-(4'-methyl-4-nitro-biphenyl-2-carbonyl)-piperazin-1-yl]-phenyl}-ethanone In analogy to a procedure described by Leadbeater et al. [N.E. Leadbeater, M. Marco, Org. Lett. 4, 2973 (2002)] a stirred mixture of 1 eq. 1-{4-[4-(2-bromo-5-nitro-benzoyl)-piperazin-1-yl]-3-fluoro-phenyl}-ethanone (Example 4), 1.05 eq. 4-methylphenylboronic acid, 1 eq. tetrabutylammonium bromide. 2.5 eq. sodium carbonate and 0.01 eq Pd(OAc)$_2$ in water (20 ml per mmol) were heated in a sealed tube to 150° C. by microwave irradiation for 1 minute. Then the reaction mixture is diluted with water, extracted with AcOEt, the pooled organic extracts dried over $Na_2SO_4$, filtered and evaporated. The crude product is purified by preparative HPLC on a YMC Combiprep ODS-AQ column with an acetonitrile/water+0.1% formic acid gradient to yield the title compound (table 2).

According to the above procedure H described for the synthesis of Example 29, further derivatives have been synthesized from of 1-{4-[4-(2-Bromo-5-nitro-benzoyl)-piperazin-1-yl]-3-fluoro-phenyl}-ethanone and boronic acids (Examples 29-32).

Procedure I: Stille Coupling

EXAMPLE 44

(2-Isopropenyl-5-methanesulfonyl-phenyl)-[4-(4-trifluoromethyl-phenyl)-piperazin-1-yl]-methanone A mixture of (2-Iodo-5-methanesulfonyl-phenyl)-[4-(4-trifluoromethyl-phenyl)-piperazin-1-yl]-methanone (Example 9; 100 mg, 0.186 mmol), Tributyl-isopropenyl-stannane (CAS: 100073-15-2; 74 mg, 0.223 mmol), Tris (dibenzylideneacetone)dipalladium chloroform complex (15.4 mg, 0.0149 mmol), Triphenylarsine (27 mg, 0.0856 mmol), Copper iodide (3.2 mg, 0.0167 mmol) in N,N-Dimethylformamide (1 ml) was heated at 90° C. for 75 minutes. The mixture was cooled to room temperature and DMF was evaporated under high vacuum. The residue was dissolved in Ethyl acetate and 4mL of a 30% Potassium fluoride solution were added. The mixture was stirred for 30 minutes. Then the aqueous phase was separated and extracted 2 times with Ethyl acetate. The organic phases were combined, washed with water, dried with Na2SO4, filtered and evaporated to dryness. The so obtained residue was chromatographed over SiO2 (Heptane/EtOAc 0% to 30% over 15 minutes) to provide the title compound (59 mg, 70% as a yellow solid).

According to the above procedure I described for the synthesis of Example 44 further derivatives have been synthesized from (2-Iodo-5-methanesulfonyl-phenyl)-[4-(4-trifluoromethyl-phenyl)-piperazin-1-yl]-methanone and stannanes (Examples 28, 34-37, 57-60).

According to the above procedure I described for the synthesis of Example 44, Example 16 has been synthesized from 1-{4-[4-(2-Bromo-5-nitro-benzoyl)-piperazin-1-yl]-3-fluoro-phenyl}-ethanone.

Procedure I

EXAMPLE 33

(2-Ethynyl-5-methanesulfonyl-phenyl)-[4-(4-trifluoromethyl-phenyl)-piperazin-1-yl]-methanone To a solution of (5-Methanesulfonyl-2-trimethylsilanyl-ethynyl-phenyl)-[4-(4-trifluoromethyl-phenyl)-piperazin-1-yl]-methanone, Example L (45 mg, 0.0885 mmol) in methanol (0.5 ml) was added K2CO3 (4 mg, 0.0289 mmol). The mixture was stirred at rt for 1 hour. The solvent was removed in vacuo. The residue was purified on SiO2, Eluent: Heptane/AcOEt 0%,-40% (10 minutes), then 40% (5 minutes) to provide the title compound (16 mg, 42%, yellow foam), M+H=437.1

Procedure K: Hydrogenation

EXAMPLE 56

(2-Isopropyl-5-methanesulfonyl-phenyl)-[4-(4-trifluoromethyl-phenyl)-piperazin-1-yl]-methanone To a solution of (2-Isopropenyl-5-methanesulfonyl-phenyl)-[4-(4-trifluoromethyl-phenyl)-piperazin-1-yl]-methanone, (Example 44, 20 mg, 0.0442 mmol) in Ethylacetate (1 ml) was added Pd/C 10% (1 mg). The mixture was hydrogenated at rt for 1 hour. Then, Pd/C 10% (10 mg) and Ethylacetate (5mL) were added and the mixture was hydrogenated at reflux temperature for 1 hour. The mixture was diluted with MeCl2, filtered and the filtrate was concentrated in vacuo. The crude mixture was purified on SiO2 Eluent: Heptane/AcOEt 0% to 40% (20 minutes) to provide the title compound (14 mg, 70%, yellow solid); M+H=455.2

Procedure L: Hydrogenation

EXAMPLE 67

[5-Methanesulfonyl-2-(tetrahydro-pyran-4-yl)-phenyl]-[4-(4-trifluoromethyl-phenyl)-piperazin-1-yl]-methanone A suspension of [2-(3,6-Dihydro-2H-pyran-4-yl)-5-methanesulfonyl-phenyl]-[4-(4-trifluoromethyl-phenyl)-piperazin-1-yl]-methanone, Example 60 (30 mg, 0.0607 mmol) in methanol (1.5 ml) was acidified to pH=1 with HCl solution in ether. The mixture was evaporated to dryness and the residue was taken up in Methanol (5 mL). Then Pd/C 10% (15 mg) was added and the mixture was hydrogenated at reflux temperature for 20 hours. The mixture was diluted with MeOH, filtered and the filtrate was concentrated in vacuo. The resulting mixture was purified on a SiO2: Eluent: Heptane/EtOAc 0% to 70% (20 minutes) then 70% (10 minutes) to provide the title compound (19 mg, white solid; Solid; M+H=497.2).

According to the above procedure L described for the synthesis of Example 67, Example 92 has been synthesized from Example 89.

According to the above procedure L described for the synthesis of Example 67, Example 93 has been synthesized from Example 91.

Procedure M: Cyclopropanation, Corey Reaction

EXAMPLE 61

[5-Methanesulfonyl-2-(1-methyl-cyclopropyl)-phenyl]-[4-(4-trifluoromethyl-phenyl)-piperazin-1-yl]-methanone To a suspension of Trimethylsulfoxonium iodide (21.9 mg, 0.1 mmol) in dry DMSO (300 uL) was added Potassium tert-butoxyde (11.3 mg, 0.101 mmol) portionwise. A solution of (2-Isopropenyl-5-methanesulfonyl-phenyl)-[4-(4-trifluoromethyl-phenyl)-piperazin-1-yl]-methanone; Example 44 (20 mg, 0.0442 mmol) in dry THF (200 uL) was prepared separately and then added to the above suspension dropwise at room temperature. The reaction mixture was stirred at room temperature for 1 hour and then at 60° C. for 20 hours. The it was cooled down to rt and a solution of Trimethylsulfoxonium iodide (21.9 mg, 0.1 mmol) and Potassium tert-butoxyde (11.3 mg, 0.101 mmol) in dry DMSO (300 uL) was slowly added. Water was added and the solution was extracted 2 times with Ethylacetate. The combined organic phases were washed with water (3 times), dried over Na2SO4, filtered and the solvent was removed in vacuo. The residue was chromatographed on SiO2 Eluent: Heptane/EtOAc to provide the title compound (4.2 mg, 20%, white solid; Solid; M+H=467.2)

Procedure N: Trifluoromethylation

EXAMPLE 66

5-Methanesulfonyl-2-trifluoromethyl-phenyl)-[4-(4-trifluoromethyl-phenyl)-piperazin-1-yl]-methanone A mixture of (2-Iodo-5-methanesulfonyl-phenyl)-[4-(4-trifluoromethyl-phenyl)-piperazin-1-yl]-methanone; Example 9, (50 mg, 0.0929 mmol), (Trifluoromethyl)trimethylsilane (27 ul, 0.186 mmol), Potassium fluoride (7.5 mg, 0.13 mmol), Copper iodide (28 mg, 0.149 mmol) and 1-Methyl-2-pyrrolidone (0.25 ml) in N,N-Dimethylformamide (0.25 ml) was stirred at room temperature under Argon in a sealed tube for 17 hours. Water was added to the solution and the reaction mixture was extracted with Ethyl acetate. The organic layers were combined, dried over Na2SO4, filtered and evaporated to dryness.

This oil was purified on SiO2, Eluent: Heptane/EtOAc 0% to 100% (10 minutes) to the title compound (40 mg, 90% yield, brown foam, M+H=481.1).

EXAMPLE 43

2-[4-(4-Acetyl-2-fluoro-phenyl)-piperazine-1-carbonyl]-4-nitro-benzoic acid methyl ester Following procedure D, the title compound is prepared by reaction of methyl 4-nitrophthalate [90072-77-8] with 1-(3fluoro-4-piperazin-1-yl-phenyl)-ethanone (m.p. 189-191° C., MS (ISP): 429.4 M+H+).

EXAMPLE 68

1-{4-[4-(2-Cyclohex-1-enyl-5-methanesulfonyl-benzoyl)-piperazin-1-yl]-3-fluoro-phenyl}-ethanone Following procedure E, 1-{4-[4-(2-Cyclohex-1-enyl-5-methanesulfonyl-benzoyl)-piperazin-1-yl]-3-fluoro-phenyl}-ethanone is prepared from 2-cyclohex-1-enyl-5-methanesulfonyl-benzoic acid (Example G) and 1-(3-fluoro-4-piperazin-1-yl-phenyl)-ethanone: light yellow gum, MS (ISP): 485.3 MH$^+$.

EXAMPLE 70

1-{3-Fluoro-4-[4-(5-nitro-2-trifluoromethyl-benzoyl)-piperazin-1-yl]-phenyl}-ethanone Following procedure E, 1-{3-Fluoro-4-[4-(5-nitro-2-trifluoromethyl-benzoyl)-piperazin-1-yl]-phenyl}-ethanone is prepared from 5-nitro-2-trifluoromethyl-benzoic acid (Example K) and 1-(3-fluoro-4-piperazin-1-yl-phenyl)-ethanone: colourless solid, MS (ISP): 440.2 (M+H$^+$).

EXAMPLE 77

(2-Cyclohex-1-enyl-5-methanesulfonyl-phenyl)-[4-(4-trifluoromethyl-phenyl)-piperazin-1-yl]-methanone Following procedure E, (2-Cyclohex-1-enyl-5-methanesulfonyl-phenyl)-[4-(4-trifluoromethyl-phenyl)-piperazin-1-yl]-methanone is prepared from 2-cyclohex-1-enyl-5-methanesulfonyl-benzoic acid (Example G) 1-(4-trifluoromethyl-phenyl)-piperazine: colourless solid, MS (ISP): 493.2 (M+H$^+$).

EXAMPLE 71

1-{4-[4-(2-Cydopent-1-enyl-5-methanesulfonyl-benzoyl)-piperazin-1-yl]-3-fluoro-phenyl}-ethanone Following procedure E, 1-{4-[4-(2-Cyclopent-1-enyl-5-methanesulfonyl-benzoyl)-piperazin-1-yl]-3-fluoro-phenyl}-ethanone is prepared from 2-cyclopent-1-enyl-5-methanesulfonyl-benzoic acid (Example H) 1-(3-fluoro-4-piperazin-1-yl-phenyl)-ethanone: colourless foam, MS (ISP): 471.4 (M+H$^+$).

EXAMPLE 74

(2-Cyclopent-1-enyl-5-methanesulfonyl-phenyl)-[4-(4-trifluoromethyl-phenyl)-piperazin-1-yl]-methanone Following procedure E, (2-Cyclopent-1-enyl-5-methanesulfonyl-phenyl)-[4-(4-trifluoromethyl-phenyl)-piperazin-1-yl]-methanone is prepared from 2-cyclopent-1-enyl-5-methanesulfonyl-benzoic acid (Example H) and 1-(4-trifluoromethyl-phenyl)-piperazine: colourless foam, MS (ISP): 479.5 (M+H$^+$).

EXAMPLE 72

1-(4-{4-[2-(3,6-Dihydro-2H-pyran-4-yl)-5-methanesulfonyl-benzoyl]-piperazin-1-yl}-3-fluoro-phenyl)-ethanone Following procedure E, 1-(4-{4-[2-(3,6-Dihydro-2H-pyran-4-yl)-5-methanesulfonyl-benzoyl]-piperazin-1-yl}-3-fluoro-phenyl)-ethanone is prepared from 2-(3,6-dihydro-2H-pyran-4-yl)-5-methanesulfonyl-benzoic acid (Example J) and 1-(3-fluoro-4-piperazin-1-yl-phenyl)-ethanone: light-yellow crystals, MS (ISP): 487.4 (M+H$^+$).

EXAMPLE 75

(2-Cyclohept-1-enyl-5-methanesulfonyl-phenyl)-[4-(4-trifluoromethyl-phenyl)-piperazin-1-yl]-methanone Following procedure E, (2-Cyclohept-1-enyl-5-methanesulfonyl-phenyl)-[4-(4-trifluoromethyl-phenyl)-piperazin-1-yl]-methanone is prepared from 2-cyclohept-1-enyl-5-methanesulfonyl-benzoic acid (Example I) and 1-(4-trifluoromethyl-phenyl)-piperazine: colourless crystals, MS (ISP): 507.5 (M+H$^+$).

EXAMPLE 73

1-{4-[4-(2-Cyclohept-1-enyl-5-methanesulfonyl-benzoyl)-piperazin-1-yl]-3-fluoro-phenyl}-ethanone Following procedure E, 1-{4-[4-(2-Cyclohept-1-enyl-5-methanesulfonyl-benzoyl)-piperazin-1-yl]-3-fluoro-phenyl}-ethanone is prepared from 2-cyclohept-1-enyl-5-methanesulfonyl-benzoic acid and 1-(3-fluoro-4-piperazin-1-yl-phenyl)-ethanone: colourless foam, MS (ISP): 499.4 (M+H$^+$).

EXAMPLE 69

(2-Cyclohexyl-5-methanesulfonyl-phenyl)-[4-(4-ethyl-2-fluoro-phenyl)-piperazin-1-yl]-methanone Following procedure K using methanol as solvent instead of ethylacetate, (2-Cyclohexyl-5-methanesulfonyl-phenyl)-[4-(4-ethyl-2-fluoro-phenyl)-piperazin-1-yl]-methanone is prepared from 1-{4-[4-(2-Cyclohex-1-enyl-5-methanesulfonyl-benzoyl)-piperazin-1-yl]-3-fluoro-phenyl}-ethanone (Example 68): colourless solid, MS (ISP): 474.0 MH$^+$.

EXAMPLE 78

(2-Cyclohexyl-5-methanesulfonyl-phenyl)-[4-(4-trifluoromethyl-phenyl)-piperazin-1-yl]-methanone Following procedure K using methanol as solvent instead of ethylacetate, (2-Cyclohexyl-5-methanesulfonyl-phenyl)-[4-(4-trifluoromethyl-phenyl)-piperazin-1-yl]-methanone is prepared from (2-cyclohex-1-enyl-5-methanesulfonyl-phenyl)-[4-(4-trifluoromethyl-phenyl)-piperazin-1-yl]-methanone (Example 77): colourless solid, MS (ISP): 495.9 MH$^+$, 537.0 (M+H+MeCN)$^+$.

Procedure O

EXAMPLE 76

2-[4-(4-Trifluoromethyl-phenyl)-piperazine-1-carbonyl]-biphenyl-4-sulfonic acid methylamide To a solution of 4-Chloro-N-methyl-3-[4-(4-trifluoromethyl-phenyl)-piperazine-1-carbonyl]-benzenesulfonamide (Example M; 30 mg, 0.065 mmol) in dioxane (2 ml) was added phenylboronic acid (12 mg, 0.098 mmol) followed by potassium fluoride (12 mg) and bis(tri-t-butylphosphine) palladium. The reaction mixture was then stirred for 19 hours at 90° C. After such time were added again (every 24 hours) the same amounts of phenylboronic acid, potassium fluoride, and bis(tri-t-butylphosphine) palladium After 3 days, the reaction mixture was diluted with ethyl acetate, filtered and concentrated in vacuo. The residue was purified by preparative HPLC (MeCN, H20+0.005 N HCOOH) to yield the title compound (7.4 mg). (M+H+: 504.4.)

Procedure P

EXAMPLE 79

(2-Cyclopentyl-5-methanesulfonyl-phenyl)-[4-(4-trifluoromethyl-phenyl)-piperazin-1-yl]-methanone (2-Cyclopent-1-enyl-5-methanesulfonyl-phenyl)-[4-(4-trifluoromethyl-phenyl)-piperazin-1-yl]-methanone (Example 74) is hydrogenated in MeOH in presence of 10% Pd/C under a hydrogen pressure of 50 bar at 50° C. for 18h. Filtration, evaporation of the solvent and purification of the residue by preparative HPLC on a C-18 column with a H$_2$O/MeCN gradient provided (2-Cyclopentyl-5-methanesulfonyl-phenyl)-[4-(4-trifluoromethyl-phenyl)-piperazin-1-yl]-methanone in 94% yield as colourless foam (M+H$^+$: 481.5.).

Procedure Q

EXAMPLE 80

[4-(4-Ethyl-2-fluoro-phenyl)-piperazin-1-yl]-[5-methanesulfonyl-2-(tetrahydro-pyran-4-yl)-phenyl]-methanone 1-(4-{4-[2-(3,6-Dihydro-2H-pyran-4-yl)-5-methanesulfonyl-benzoyl]-piperazin-1-yl}-3-fluoro-phenyl)-ethanone (Example 72) is hydrogenated in EtOH in presence of Raney nickel under a hydrogen pressure of 100 bar at 100IC for 18 h. Filtration, evaporation of the solvent and purification of the residue by preparative HPLC on a C-18 column with a H$_2$O/MeCN gradient provided [4-(4-Ethyl-2-fluoro-phenyl)-piperazin-1-yl]-[5-methanesulfonyl-2-(tetrahydro-pyran-4-yl)-phenyl]-methanone in 41% yield as colourless crystals (M+H$^+$: 475.5.).

Procedure R

EXAMPLE 81

(2-Cycloheptyl-5-methanesulfonyl-phenyl)-[4-(4-trifluoromethyl-phenyl)-piperazin-1-yl]-methanone (2-Cyclohept-1-enyl-5-methanesulfonyl-phenyl)-[4-(4-trifluoromethyl-phenyl)-piperazin-1-yl]-methanone (Example 75) ) is hydrogenated in MeOH in presence of 10% Pd/C under a hydrogen pressure of 100 bar at 100° C. for 18 h. Filtration, evaporation of the solvent and purification of the residue by preparative HPLC on a C-18 column with a H$_2$O/MeCN gradient provided (2-Cycloheptyl-5-methanesulfonyl-phenyl)-[4-(4-trifluoromethyl-phenyl)-piperazin-1-yl]-methanone in 73% yield as colourless gum (M+H$^+$: 509.6.).

Procedure S

EXAMPLE 89

[2-(3,6-Dihydro-2H-pyran-4-yl)-5-methanesulfonyl-phenyl]-[4-(2-fluoro-4-methanesulfonyl-phenyl)-piperazin-1-yl]-methanone Following procedure I, [2-(3,6-Dihydro-2H-pyran-4-yl)-5-methanesulfonyl-phenyl]-[4-(2-fluoro-4-methanesulfonyl-phenyl)-piperazin-1-yl]-methanone is prepared from [4-(2-Fluoro-4-methanesulfonyl-phenyl)-piperazin-1-yl]-(2-iodo-5-methanesulfonyl-phenyl)-methanone (Example R) and tributyl-(3,6-dihydro-2H-pyran-4-yl)-stannane (CAS: 535924-69-7). 42% yield, light yellow foam(M+NH4+: 540.3)

EXAMPLE 90

4-{4-[2-(3,6-Dihydro-2H-pyran-4-yl)-5-methanesulfonyl-benzoyl]-piperazin-1-yl}-3-fluoro-benzonitrile Following procedure I, 4-{4-[2-(3,6-Dihydro-2H-pyran-4-yl)-5-methanesulfonyl-benzoyl]-piperazin-1-yl}-3-fluoro-benzonitrile is prepared from 3-Fluoro-4-[4-(2-iodo-5-methanesulfonyl-benzoyl)-piperazin-1-yl]-benzonitrile (Example S) and tributyl-(3,6-dihydro-2H-pyran-4-yl)-stannane (CAS: 535924-69-7). 36% yield, white foam(M+H+:470.1)

EXAMPLE 91

[2-(3,6-Dihydro-2H-pyran-4-yl)-5-methanesulfonyl-phenyl]-[4-(2-fluoro-4-trifluoromethyl-phenyl)-piperazin-1-yl]-methanone Following procedure I, [2-(3,6-Dihydro-2H-pyran-4-yl)-5-methanesulfonyl-phenyl]-[4-(2-fluoro-4-trifluoromethyl-phenyl)-piperazin-1-yl]-methanone is prepared from [4-(2-Fluoro-4-trifluoromethyl-phenyl)-piperazin-1-yl]-(2-iodo-5-methanesulfonyl-phenyl)-methanone (Example N) and tributyl-(3,6-dihydro-2H-pyran-4-yl)-stannane (CAS: 535924-69-7). 40% yield, white foam(M+H+: 513.2)

Procedure T

EXAMPLE 94

[5-Methanesulfonyl-2-(4-methyl-thiazol-2-yl)-phenyl]-[4-(4-trifluoromethyl-phenyl)-piperazin-1-yl]-methanone A mixture of (5-Methanesulfonyl-2-trimethylstannanyl-phenyl)-[4-(4-trifluoromethyl-phenyl)-piperazin-1-yl]-methanone (Example T, 100 mg, 0.17 mmol), 2-Iodo-4-methyl-thiazole ( CAS: 34203-25-3; 43 mg, 0.19 mmol), Bis(dibenzylideneacetone)palladium (8 mg, 0.01 mmol), Triphenylarsine (25 mg, 0.08 mmol) and Copper iodide (3 mg, 0.02 mmol) in N,N-Dimethylformamide (2 ml) was heated at 100° C. for 1 hour. The mixture was cooled to room temperature, diluted with water, and extracted three times with Ethyl acetate. The combined organic phases were dried with Na2SO4 ,filtered, and evaporated to dryness. The residue was chromatographed over SiO2 (methanol/dichoromethane 0% to 0.5%) to provide the title compound (22 mg, 25%) as a light yellow solid. MS (ISP): 510.5 MH$^+$.

EXAMPLE 95

[5-Methanesulfonyl-2-(5-methyl-thiazol-2-yl)-phenyl]-[4-(4-trifluoromethyl-phenyl)-piperazin-1-yl]-methanone Following procedure T, [5-Methanesulfonyl-2-(5-methyl-thiazol-2-yl)-phenyl]-[4-(4-trifluoromethyl-phenyl)-piperazin-1-yl]-methanone is prepared from (5-Methanesulfonyl-2-trimethylstannanyl-phenyl)-[4-(4-trifluoromethylphenyl)-piperazin-1-yl]-methanone (Example T) and 2-Iodo-5-methyl-thiazole (Example U): off-white solid, MS (ISP): 510.3 (M+H⁺).

EXAMPLE 96

[5-Methanesulfonyl-2-(2-methyl-pyridin-4-yl)-phenyl]-[4-(4-trifluoromethyl-phenyl)-piperazin-1-yl]-methanone Following procedure T, [5-Methanesulfonyl-2-(2-methyl-pyridin-4-yl)-phenyl]-[4-(4-trifluoromethyl-phenyl)-piperazin-1-yl]-methanone is prepared from (5-Methanesulfonyl-2-trimethylstannanyl-phenyl)-[4-(4-trifluoromethyl-phenyl)-piperazin-1-yl]-methanone (Example T) and 4-Bromo-2-methyl-pyridine (CAS: 22282-99-1): off-white solid, MS (ISP): 504.0 (M+H⁺).

EXAMPLE 97

[5-Methanesulfonyl-2-(1-methyl-1H-imidazol-4-yl)-phenyl]-[4-(4-trifluoromethyl-phenyl)-piperazin-1-yl]-methanone Following procedure T, [5-Methanesulfonyl-2-(1-methyl-1H-imidazol-4-yl)-phenyl]-[4-(4-trifluoromethyl-phenyl)-piperazin-1-yl]-methanone is prepared from (5-Methanesulfonyl-2-trimethylstannanyl-phenyl)-[4-(4-trifluoromethyl-phenyl)-piperazin-1-yl]-methanone (Example T) and 4-Iodo-1-methyl-1H-imidazole (CAS: 71759-87-0): light yellow solid, MS (ISP): 493.3 (M+H⁺).

Procedure U

EXAMPLE 139

4-{4-[2-((E)-2-Cyano-vinyl)-5-methanesulfonyl-benzoyl]-piperazin-1-yl}-benzonitrile A mixture of 0.5 mmol 4-[4-(2-Iodo-5-methanesulfonyl-benzoyl)-piperazin-1-yl]-benzonitrile (Example AG), 6.3 mmol acrylonitrile, 9.0 mmol triethylamine and 0.2 mmol of bis-(triphenylphosphin)-palladium(II)-dichloride in 10 ml dimethylformamide is hold under argon for 2 hours at 80°. The reaction mixture is concentrated. Chromatography (SiO2; cyclohexane/ethyl acetate 9:1) yields the title compound as a slightly yellow solid (105 mg). ). (M+H+: 421.2)

EXAMPLE 140

(E)-3-{2-[4-(4-Cyano-phenyl)-piperazine-1-carbonyl]-4-methanesulfonyl-phenyl}-acrylic acid methyl ester Prepared in analogy to example 139 from 4-[4-(2-Iodo-5-methanesulfonyl-benzoyl)-piperazin-1-yl]-benzonitrile (Example AG) and methyl acrylate. Chromatography (SiO2; cyclohexane/ethyl acetate 3:7) yields the title compound as a slightly yellow solid (M+H+: 454.3)

TABLE 1

| | Structure | MW | M + H⁺ | Systematic Name | Procedure |
|---|---|---|---|---|---|
| 1 | 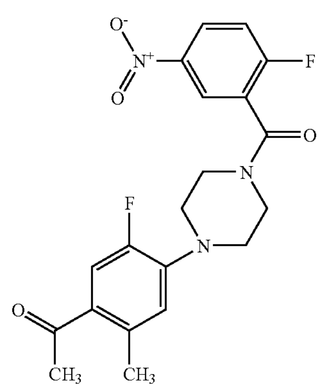 | 403.383 | NA | 1-(4-acetyl-2-fluoro-5-methylphenyl)-4-(2-fluoro-5-nitrobenzoyl)-piperazine | known |
| 2 | 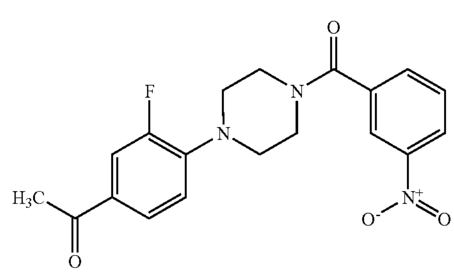 | 389.3 | 390.2 | 1-{3-Fluoro-4-[4-(2-fluoro-5-nitro-benzoyl)-piperazin-1-yl]-phenyl}-ethanone | C |

TABLE 1-continued

| | Structure | MW | M + H⁺ | Systematic Name | Procedure |
|---|---|---|---|---|---|
| 3 | 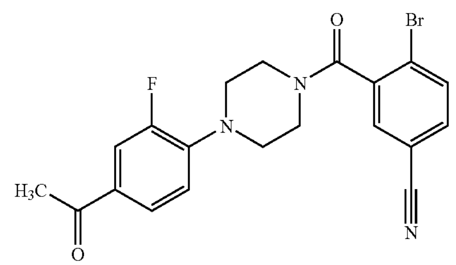 | 430.274 | 430.3 | 3-[4-(4-Acetyl-2-fluoro-phenyl)-piperazine-1-carbonyl]-4-bromo-benzonitrile | D |
| 4 | 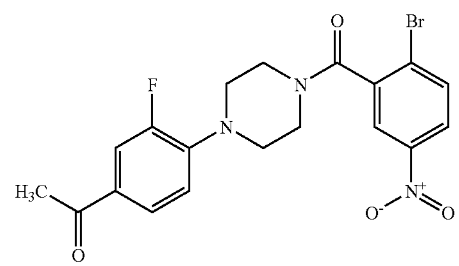 | 450.261 | 450.0 | 1-{4-[4-(2-Bromo-5-nitro-benzoyl)-piperazin-1-yl]-3-fluoro-phenyl}-ethanone | C |
| 5 | 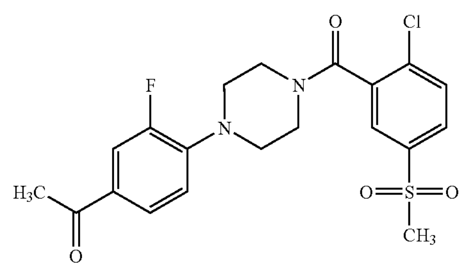 | 438.904 | 439.1 | 1-{4-[4-(2-Chloro-5-methanesulfonyl-benzoyl)-piperazin-1-yl]-3-fluoro-phenyl}-ethanone | D |
| 6 | 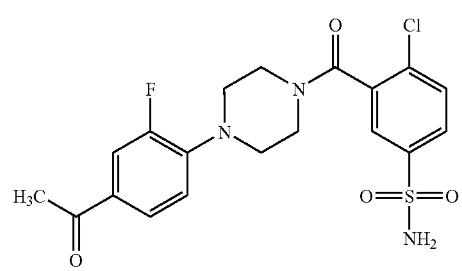 | 439.893 | 438.1 | 3-[4-(4-Acetyl-2-fluoro-phenyl)-piperazine-1-carbonyl]-4-chloro-benzenesulfonamide | D |
| 7 | 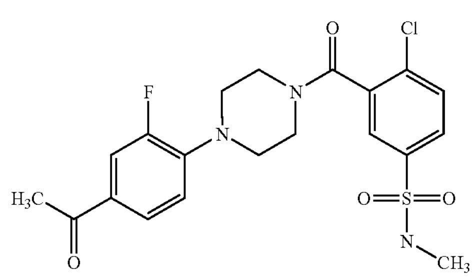 | 453.92 | 452.1 | 3-[4-(4-Acetyl-2-fluoro-phenyl)-piperazine-1-carbonyl]-4-chloro-N-methyl-benzenesulfonamide | D |

TABLE 1-continued

| | Structure | MW | M + H+ | Systematic Name | Procedure |
|---|---|---|---|---|---|
| 8 | 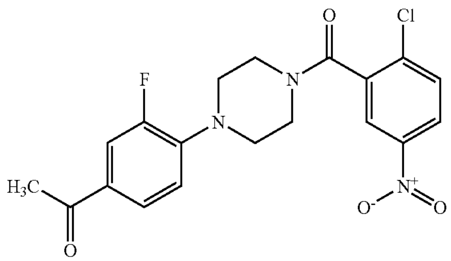 | 405.811 | 406.2 | 1-{4-[4-(2-Chloro-5-nitro-benzoyl)-piperazin-1-yl]-3-fluoro-phenyl}-ethanone | D |
| 9 | 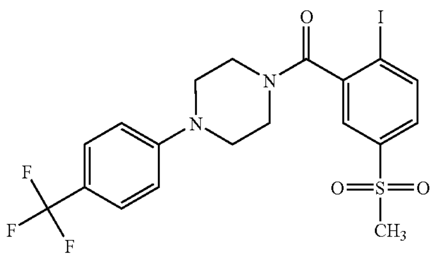 | 538.322 | 539.1 | (2-Iodo-5-methanesulfonyl-phenyl)-[4-(4-trifluoromethyl-phenyl)-piperazin-1-yl]-methanone | E |
| 10 | 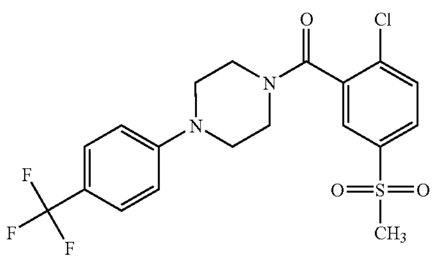 | 446.875 | 464.3 (+NH4+) | (2-Chloro-5-methanesulfonyl-phenyl)-[4-(4-trifluoromethyl-phenyl)-piperazin-1-yl]-methanone | E |
| 11 | 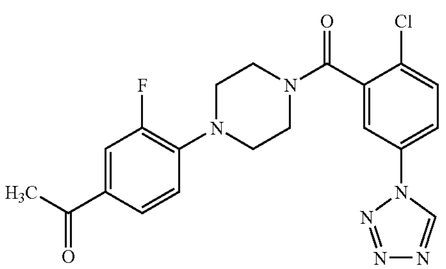 | 428.852 | 429.11 | 1-{4-[4-(2-Chloro-5-tetrazol-1-yl-benzoyl)-piperazin-1-yl]-3-fluoro-phenyl}-ethanone | E |
| 12 | 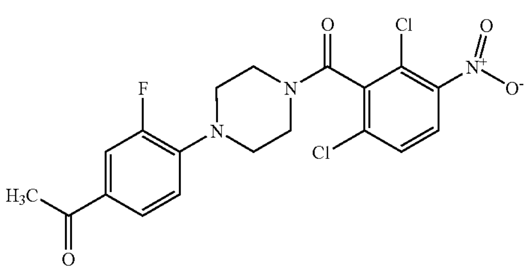 | 440.256 | 440.1 | 1-{4-[4-(2,6-Dichloro-3-nitro-benzoyl)-piperazin-1-yl]-3-fluoro-phenyl}-ethanone | E |
| 13 | 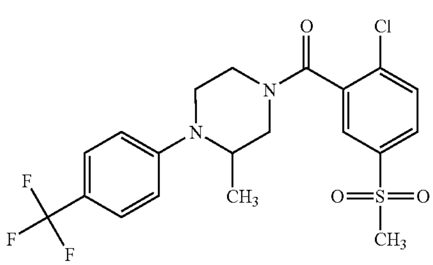 | 552.348 | 553.1 | (2-Iodo-5-methanesulfonyl-phenyl)-[3-methyl-4-(4-trifluoromethyl-phenyl)-piperazin-1-yl]-methanone | F |

TABLE 1-continued

| Structure | MW | M + H+ | Systematic Name | Procedure |
|---|---|---|---|---|

TABLE 2

| | Structure | MW | M + H+ | Name | Procedure |
|---|---|---|---|---|---|
| 14 | 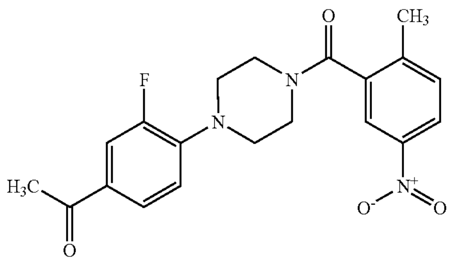 | 385.4 | 386.1 | 1-{3-Fluoro-4-[4-(2-methyl-5-nitro-benzoyl)-piperazin-1-yl]-phenyl}-ethanone | G |
| 15 | 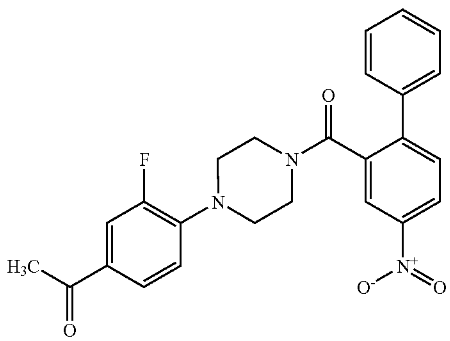 | 447.5 | 448.3 | 1-{3-Fluoro-4-[4-(4-nitro-biphenyl-2-carbonyl)-piperazin-1-yl]-phenyl}-ethanone | G |
| 16 | 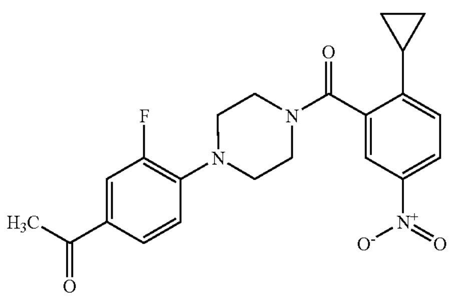 | 411.4 | 412.2 | 1-{4-[4-(2-Cyclopropyl-5-nitro-benzoyl)-piperazin-1-yl]-3-fluoro-phenyl}-ethanone | I |
| 17 | 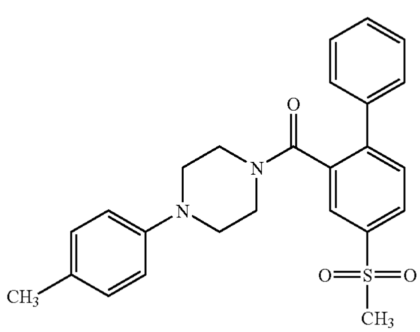 | 488.5 | 489.2 | (4-Methanesulfonyl-biphenyl-2-yl)-[4-(4-trifluoromethyl-phenyl)-piperazin-1-yl]-methanone | G |

TABLE 2-continued

| | Structure | MW | M + H+ | Name | Procedure |
|---|---|---|---|---|---|
| 18 | 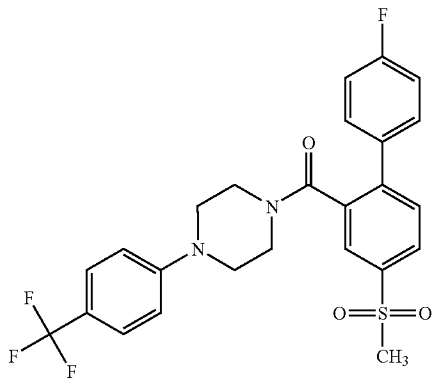 | 506.5 | 524.3 (+NH4+) | (4'-Fluoro-4-methanesulfonyl-biphenyl-2-yl)-[4-(4-trifluoromethyl-phenyl)-piperazin-1-yl]-methanone | G |
| 19 | 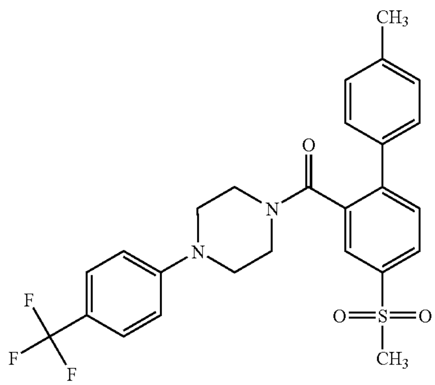 | 502.6 | 503.1 | (4-Methanesulfonyl-4'-methyl-biphenyl-2-yl)-[4-(4-trifluoromethyl-phenyl)-piperazin-1-yl]-methanone | G |
| 20 | 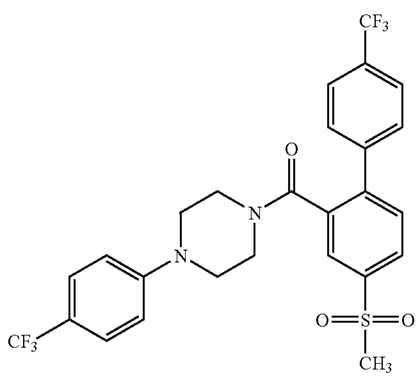 | 556.5 | 557.0 | (4-Methanesulfonyl-4'-trifluoromethyl-biphenyl-2-yl)-[4-(4-trifluoromethyl-phenyl)-piperazin-1-yl]-methanone | G |
| 21 | 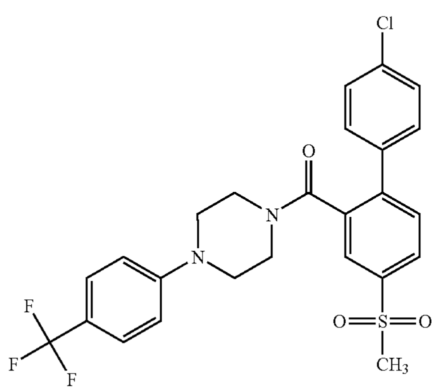 | 523.0 | 523.2 | (4'-Chloro-4-methanesulfonyl-biphenyl-2-yl)-[4-(4-trifluoromethyl-phenyl)-piperazin-1-yl]-methanone | G |

TABLE 2-continued

| | Structure | MW | M + H+ | Name | Procedure |
|---|---|---|---|---|---|
| 22 | 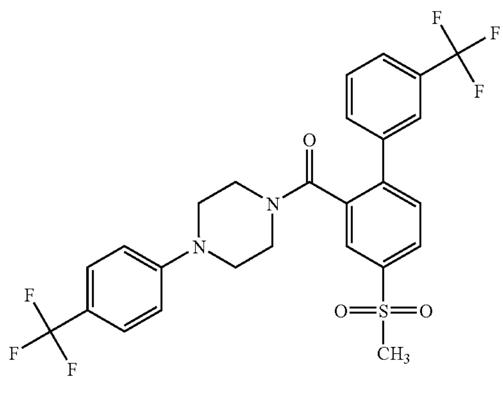 | 556.5 | 557.1 | (4-Methanesulfonyl-3'-trifluoromethyl-biphenyl-2-yl)-[4-(4-trifluoromethyl-phenyl)-piperazin-1-yl]-methanone | G |
| 23 | 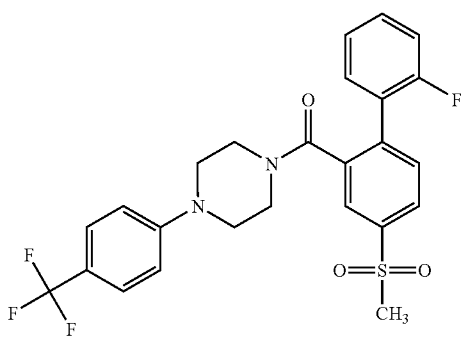 | 506.5 | 507.2 | (2'-Fluoro-4-methanesulfonyl-biphenyl-2-yl)-[4-(4-trifluoromethyl-phenyl)-piperazin-1-yl]-methanone | G |
| 24 | 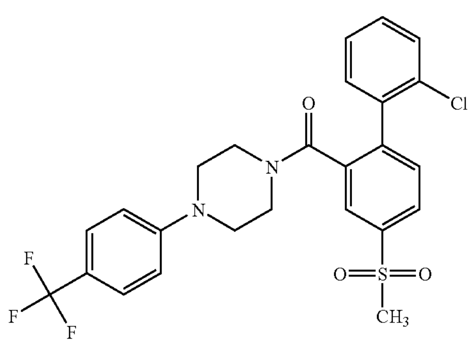 | 523.0 | 523.2 | (2'-Chloro-4-methanesulfonyl-biphenyl-2-yl)-[4-(4-trifluoromethyl-phenyl)-piperazin-1-yl]-methanone | G |
| 25 | 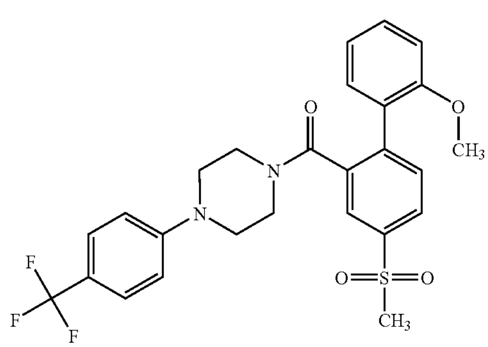 | 518.6 | 519.2 | (4-Methanesulfonyl-2'-methoxy-biphenyl-2-yl)-[4-(4-trifluoromethyl-phenyl)-piperazin-1-yl]-methanone | G |

TABLE 2-continued

| | Structure | MW | M + H⁺ | Name | Procedure |
|---|---|---|---|---|---|
| 26 | 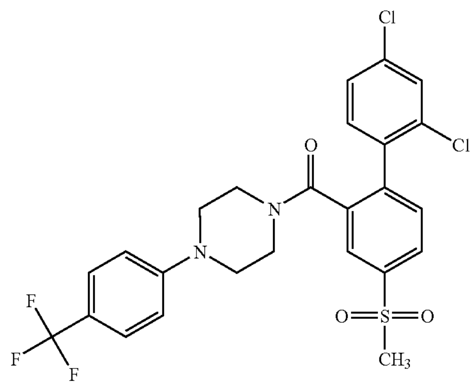 | 557.4 | 557.0 | (2',4'-Dichloro-4-methanesulfonyl-biphenyl-2-yl)-[4-(4-trifluoromethyl-phenyl)-piperazin-1-yl]-methanone | G |
| 27 | 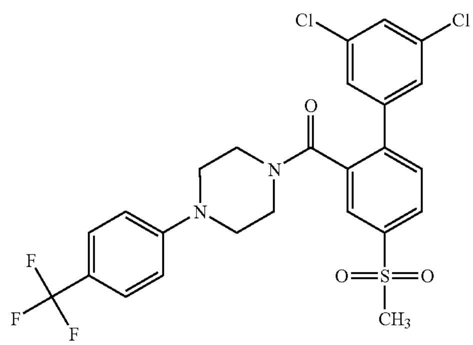 | 557.4 | 557.0 | (3',5'-Dichloro-4-methanesulfonyl-biphenyl-2-yl)-[4-(4-trifluoromethyl-phenyl)-piperazin-1-yl]-methanone | G |
| 28 | 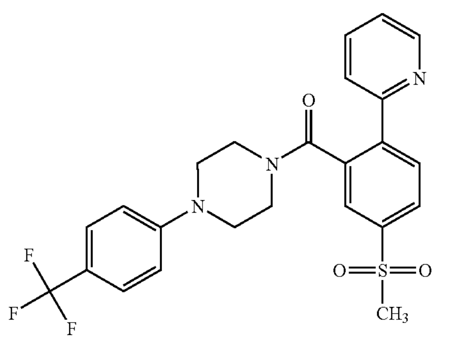 | 489.5 | 490.1 | (5-Methanesulfonyl-2-pyridin-2-yl-phenyl)-[4-(4-trifluoromethyl-phenyl)-piperazin-1-yl]-methanone | I |
| 29 | 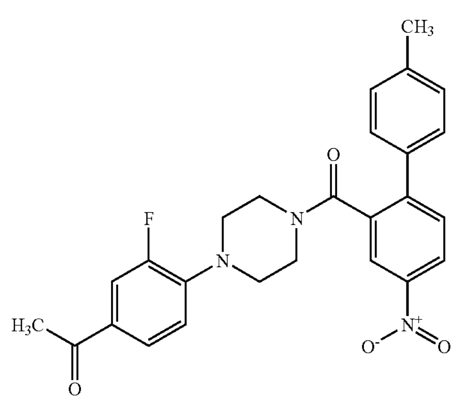 | 461.5 | 462.2 | 1-{3-Fluoro-4-[4-(4'-methyl-4-nitro-biphenyl-2-carbonyl)-piperazin-1-yl]-phenyl}-ethanone | H |

TABLE 2-continued

| | Structure | MW | M + H⁺ | Name | Procedure |
|---|---|---|---|---|---|
| 30 | 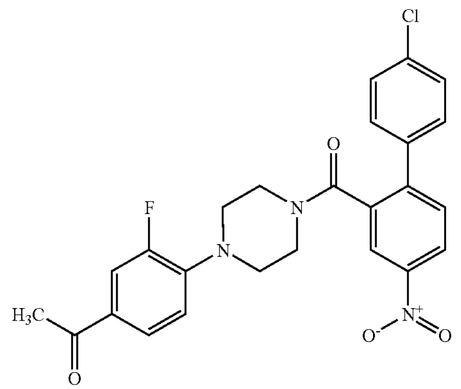 | 481.9 | 482.1 | 1-{4-[4-(4'-Chloro-4-nitro-biphenyl-2-carbonyl)-piperazin-1-yl]-3-fluoro-phenyl}-ethanone | H |
| 31 | 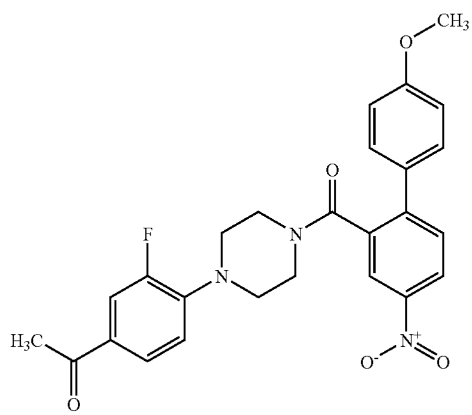 | 477.5 | 478.1 | 1-{3-Fluoro-4-[4-(4'-methoxy-4-nitro-biphenyl-2-carbonyl)-piperazin-1-yl]-phenyl}-ethanone | H |
| 32 | 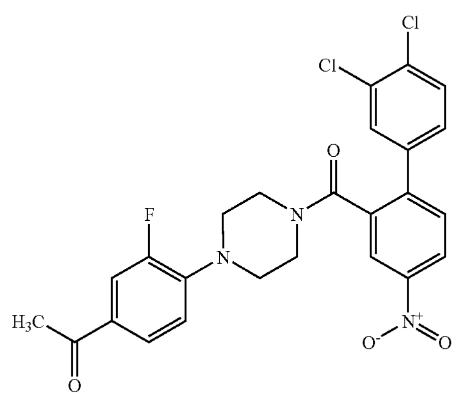 | 516.4 | 516.1 | 1-{4-[4-(3',4'-Dichloro-4-nitro-biphenyl-2-carbonyl)-piperazin-1-yl]-3-fluoro-phenyl}-ethanone | H |
| 33 | 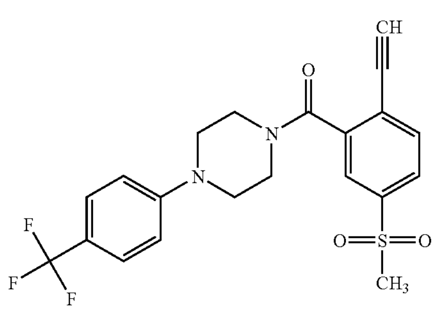 | 436.5 | 437.1 | (2-Ethynyl-5-methanesulfonyl-phenyl)-[4-(4-trifluoromethyl-phenyl)-piperazin-1-yl]-methanone | J |

TABLE 2-continued

| | Structure | MW | M + H⁺ | Name | Procedure |
|---|---|---|---|---|---|
| 34 | 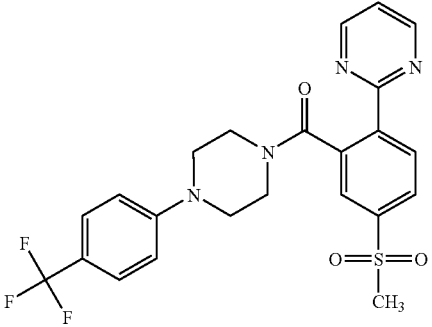 | 490.5 | 491.2 | (5-Methanesulfonyl-2-pyrimidin-2-yl-phenyl)-[4-(4-trifluoromethyl-phenyl)-piperazin-1-yl]-methanone | I |
| 35 | 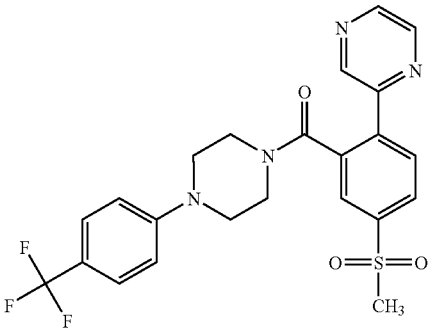 | 490.5 | 491.2 | (5-Methanesulfonyl-2-pyrazin-2-yl-phenyl)-[4-(4-trifluoromethyl-phenyl)-piperazin-1-yl]-methanone | I |
| 36 | 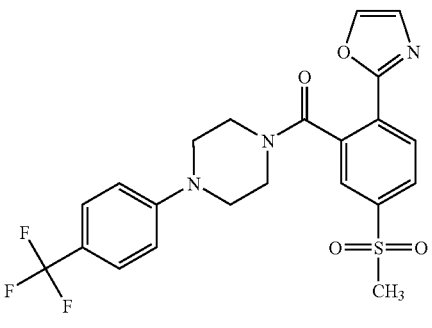 | 479.5 | 480.1 | (5-Methanesulfonyl-2-oxazol-2-yl-phenyl)-[4-(4-trifluoromethyl-phenyl)-piperazin-1-yl]-methanone | I |
| 37 | 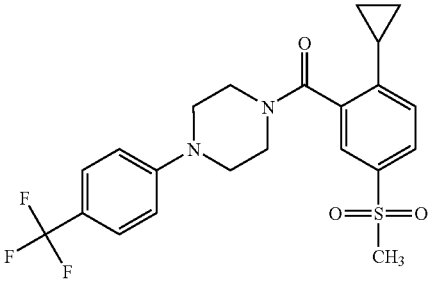 | 452.5 | 453.1 | (2-Cyclopropyl-5-methanesulfonyl-phenyl)-[4-(4-trifluoromethyl-phenyl)-piperazin-1-yl]-methanone | I |

TABLE 2-continued

| | Structure | MW | M + H+ | Name | Procedure |
|---|---|---|---|---|---|
| 38 | 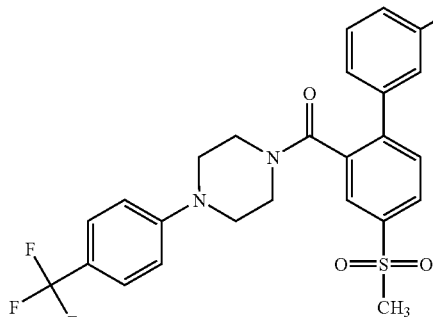 | 506.5 | 507.2 | (3'-Fluoro-4-methanesulfonyl-biphenyl-2-yl)-[4-(4-trifluoromethyl-phenyl)-piperazin-1-yl]-methanone | G |
| 39 | 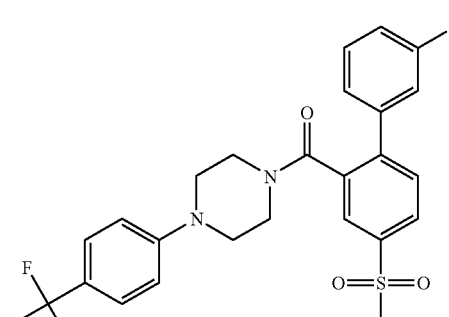 | 523.0 | 523.2 | (3'-Chloro-4-methanesulfonyl-biphenyl-2-yl)-[4-(4-trifluoromethyl-phenyl)-piperazin-1-yl]-methanone | G |
| 40 | 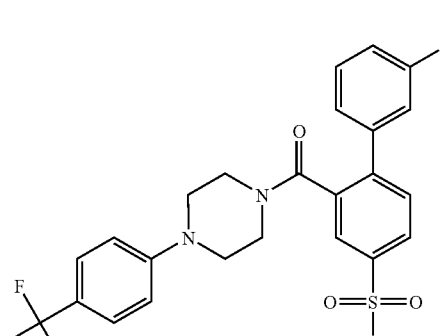 | 502.6 | 503.1 | (4-Methanesulfonyl-3'-methyl-biphenyl-2-yl)-[4-(4-trifluoromethyl-phenyl)-piperazin-1-yl]-methanone | G |
| 41 | 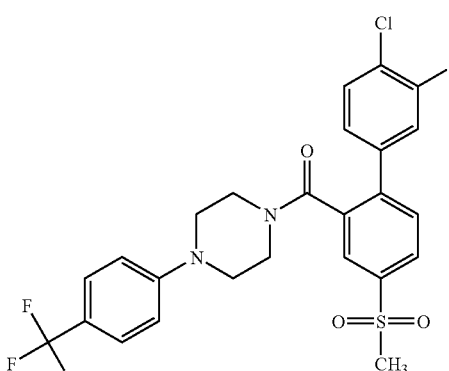 | 557.4 | 557.0 | (3',4'-Dichloro-4-methanesulfonyl-biphenyl-2-yl)-[4-(4-trifluoromethyl-phenyl)-piperazin-1-yl]-methanone | G |

TABLE 2-continued

| | Structure | MW | M + H⁺ | Name | Procedure |
|---|---|---|---|---|---|
| 42 | 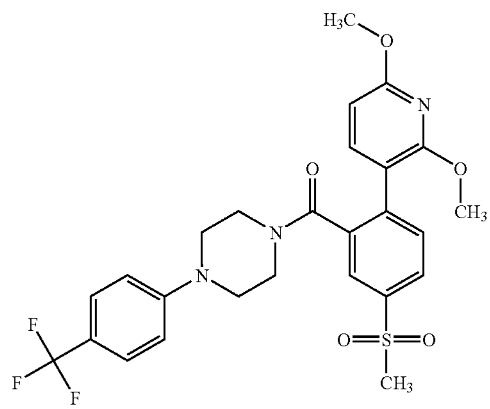 | 549.6 | 550.3 | [2-(2,6-Dimethoxy-pyridin-3-yl)-5-methanesulfonyl-phenyl]-[4-(4-trifluoromethyl-phenyl)-piperazin-1-yl]-methanone | C |
| 43 | 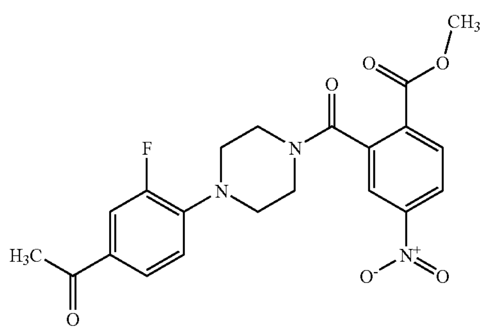 | 429.4 | 429.4 | 2-[4-(4-Acetyl-2-fluoro-phenyl)-piperazine-1-carbonyl]-4-nitro-benzoic acid methyl ester | D |
| 44 | 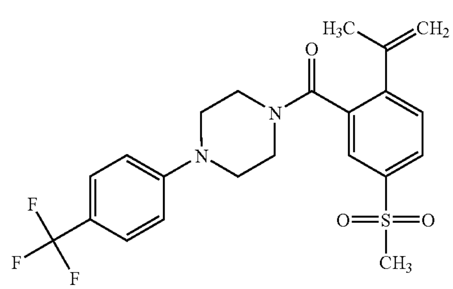 | 452.5 | 453.1 | (2-Isopropenyl-5-methanesulfonyl-phenyl)-[4-(4-trifluoromethyl-phenyl)-piperazin-1-yl]-methanone | I |
| 45 | 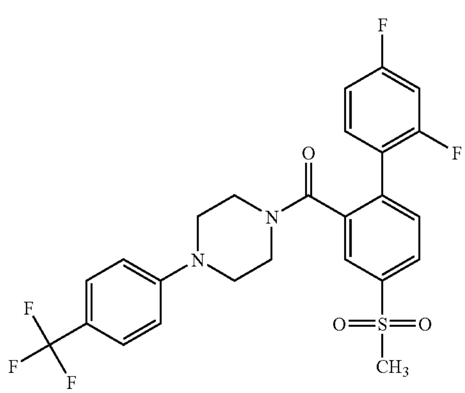 | 524.5 | 525.2 | (2',4'-Difluoro-4-methanesulfonyl-biphenyl-2-yl)-[4-(4-trifluoromethyl-phenyl)-piperazin-1-yl]-methanone | C |

TABLE 2-continued

| | Structure | MW | M + H+ | Name | Procedure |
|---|---|---|---|---|---|
| 46 | 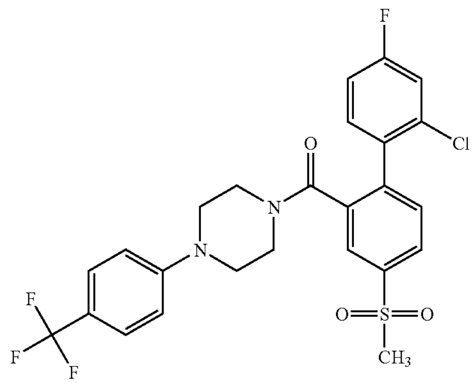 | 541.0 | 541.2 | (2'-Chloro-4'-fluoro-4-methanesulfonyl-biphenyl-2-yl)-[4-(4-trifluoromethyl-phenyl)-piperazin-1-yl]-methanone | G |
| 47 | 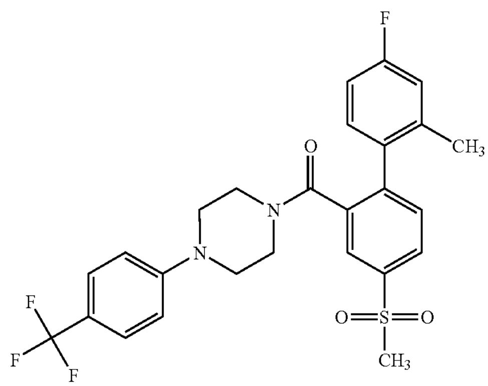 | 520.6 | 521.2 | (4'-Fluoro-4-methanesulfonyl-2'-methyl-biphenyl-2-yl)-[4-(4-trifluoromethyl-phenyl)-piperazin-1-yl]-methanone | C |
| 48 | 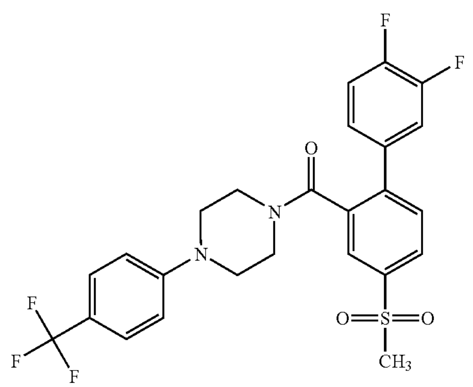 | 524.5 | 525.2 | (3',4'-Difluoro-4-methanesulfonyl-biphenyl-2-yl)-[4-(4-trifluoromethyl-phenyl)-piperazin-1-yl]-methanone | G |
| 49 | 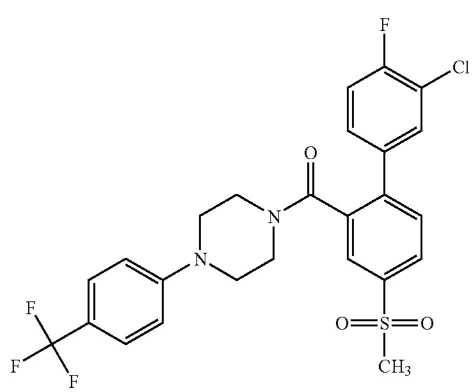 | 541.0 | 541.2 | (3'-Chloro-4'-fluoro-4-methanesulfonyl-biphenyl-2-yl)-[4-(4-trifluoromethyl-phenyl)-piperazin-1-yl]-methanone | G |

TABLE 2-continued

| | Structure | MW | M + H⁺ | Name | Procedure |
|---|---|---|---|---|---|
| 50 | 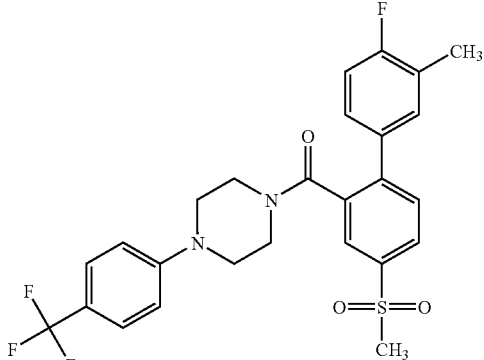 | 520.6 | 521.2 | (4'-Fluoro-4-methanesulfonyl-3'-methyl-biphenyl-2-yl)-[4-(4-trifluoromethyl-phenyl)-piperazin-1-yl]-methanone | G |
| 51 | 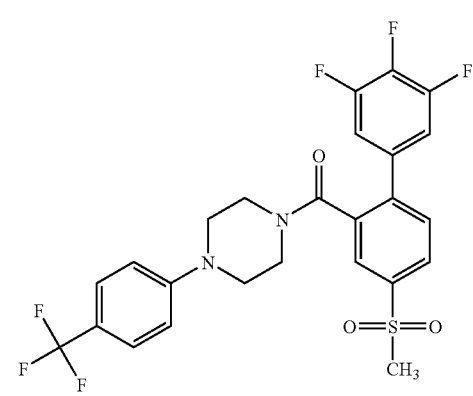 | 542.5 | 543.2 | (3',4',5'-Trifluoro-4-methanesulfonyl-biphenyl-2-yl)-[4-(4-trifluoromethyl-phenyl)-piperazin-1-yl]-methanone | G |
| 52 | 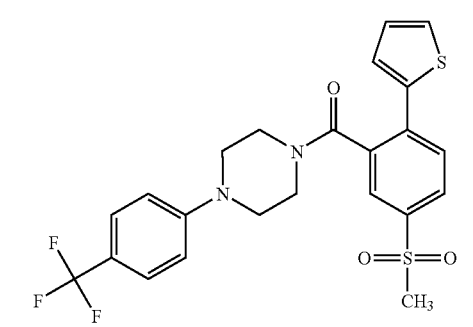 | 494.6 | 495.1 | (5-Methanesulfonyl-2-thiophen-2-yl-phenyl)-[4-(4-trifluoromethyl-phenyl)-piperazin-1-yl]-methanone | G |
| 53 | 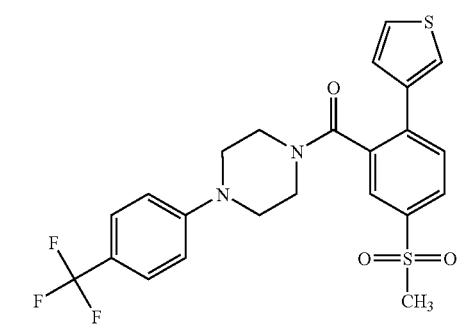 | 494.6 | 495.1 | (5-Methanesulfonyl-2-thiophen-3-yl-phenyl)-[4-(4-trifluoromethyl-phenyl)-piperazin-1-yl]-methanone | G |

TABLE 2-continued

| | Structure | MW | M + H⁺ | Name | Procedure |
|---|---|---|---|---|---|
| 54 | 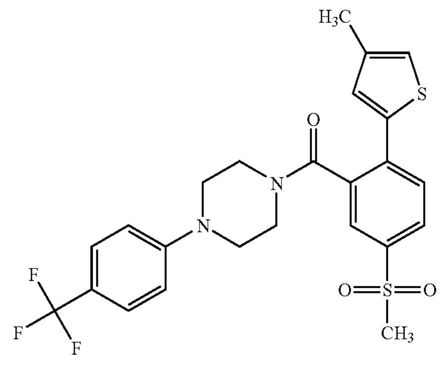 | 508.6 | 509.2 | [5-Methanesulfonyl-2-(4-methyl-thiophen-2-yl)-phenyl]-[4-(4-trifluoromethyl-phenyl)-piperazin-1-yl]-methanone | G |
| 55 | 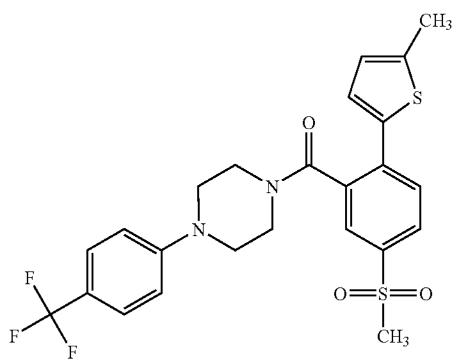 | 508.6 | 509.1 | [5-Methanesulfonyl-2-(5-methyl-thiophen-2-yl)-phenyl]-[4-(4-trifluoromethyl-phenyl)-piperazin-1-yl]-methanone | G |
| 56 | 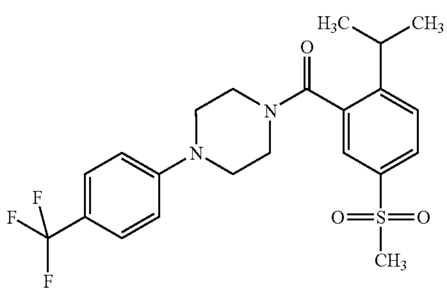 | 454.5 | 455.2 | (2-Isopropyl-5-methanesulfonyl-phenyl)-[4-(4-trifluoromethyl-phenyl)-piperazin-1-yl]-methanone | K |
| 57 | 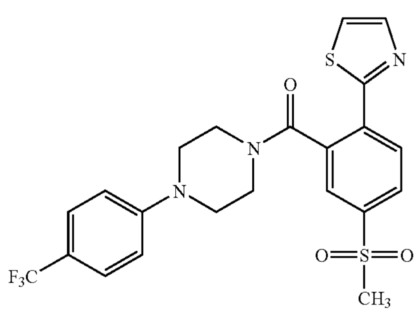 | 495.5 | 496.2 | (5-Methanesulfonyl-2-thiazol-2-yl-phenyl)-[4-(4-trifluoromethyl-phenyl)-piperazin-1-yl]-methanone | I |

TABLE 2-continued

| | Structure | MW | M + H⁺ | Name | Procedure |
|---|---|---|---|---|---|
| 58 | 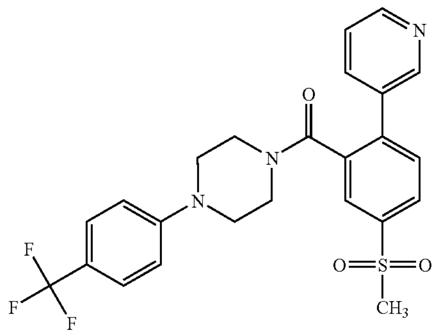 | 489.5 | 490.1 | (5-Methanesulfonyl-2-pyridin-3-yl-phenyl)-[4-(4-trifluoromethyl-phenyl)-piperazin-1-yl]-methanone | I |
| 59 | 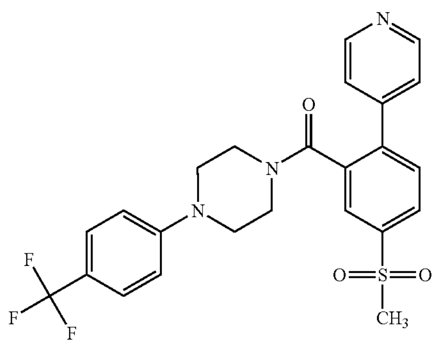 | 489.5 | 490.1 | (5-Methanesulfonyl-2-pyridin-4-yl-phenyl)-[4-(4-trifluoromethyl-phenyl)-piperazin-1-yl]-methanone | I |
| 60 | 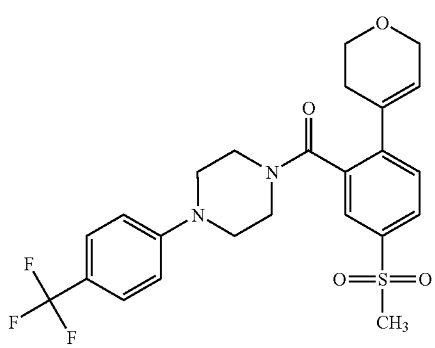 | 494.5 | 495.2 | [2-(3,6-Dihydro-2H-pyran-4-yl)-5-methanesulfonyl-phenyl]-[4-(4-trifluoromethyl-phenyl)-piperazin-1-yl]-methanone | I |
| 61 | 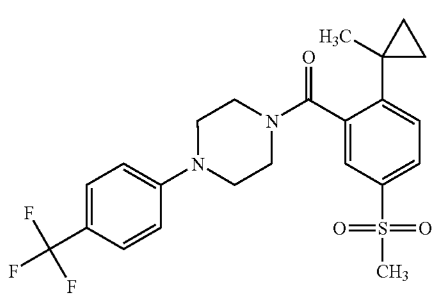 | 466.5 | 467.2 | [5-Methanesulfonyl-2-(1-methyl-cyclopropyl)-trifluoromethyl-phenyl)-piperazin-1-yl]-methanone | M |

TABLE 2-continued

| | Structure | MW | M + H⁺ | Name | Procedure |
|---|---|---|---|---|---|
| 62 | 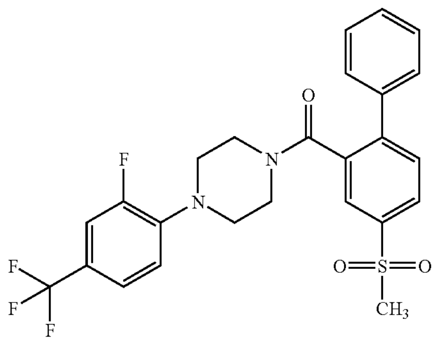 | 506.5 | 507.2 | [4-(2-Fluoro-4-trifluoromethyl-phenyl)-piperazin-1-yl]-(4-methanesulfonyl-biphenyl-2-yl)-methanone | G |
| 63 | 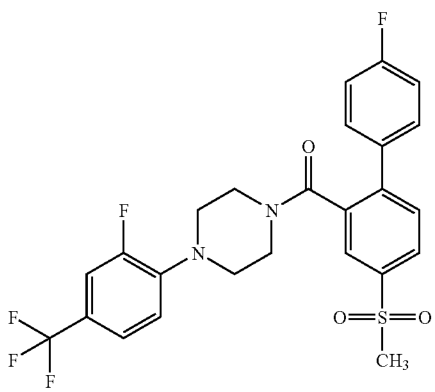 | 524.5 | 525.2 | (4'-Fluoro-4-methanesulfonyl-biphenyl-2-yl)-[4-(2-fluoro-4-trifluoromethyl-phenyl)-piperazin-1-yl]-methanone | G |
| 64 | 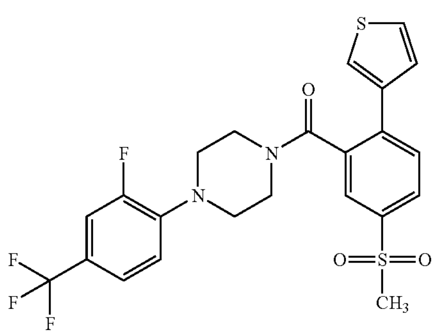 | 512.5 | 513.2 | [4-(2-Fluoro-4-trifluoromethyl-phenyl)-piperazin-1-yl]-(5-methanesulfonyl-2-thiophen-3-yl-phenyl)-methanone | G |
| 65 | 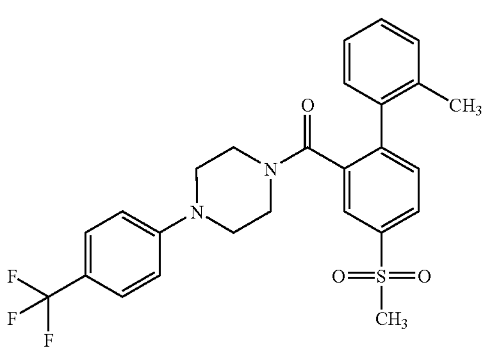 | 502.6 | 503.1 | (4-Methanesulfonyl-2'-methyl-biphenyl-2-yl)-[4-(4-trifluoromethyl-phenyl)-piperazin-1-yl]-methanone | G |

TABLE 2-continued

| | Structure | MW | M + H⁺ | Name | Procedure |
|---|---|---|---|---|---|
| 66 | 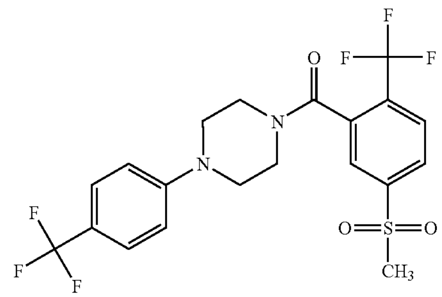 | 480.4 | 481.1 | (5-Methanesulfonyl-2-trifluoro-phenyl)-[4-(4-trifluoromethyl-phenyl)-piperazin-1-yl]-methanone | N |
| 67 | 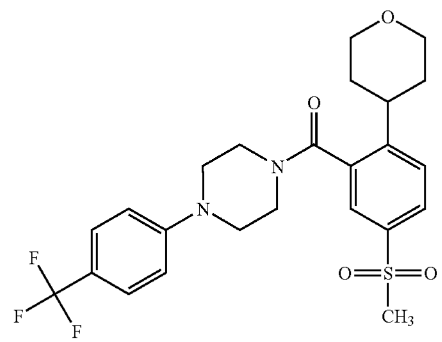 | 496.6 | 497.2 | [5-Methanesulfonyl-2-(tetrahydro-pyran-4-yl)-phenyl]-[4-(4-trifluoromethyl-phenyl)-piperazin-1-yl]-methanone | L |
| 68 | 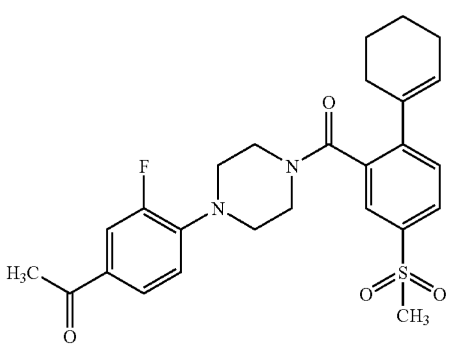 | 484.6 | 485.3 | 1-{4-[4-(2-Cyclohex-1-enyl-5-methanesulfonyl-benzoyl)-piperazin-1-yl]-3-fluoro-phenyl}-ethanone | E |
| 69 | 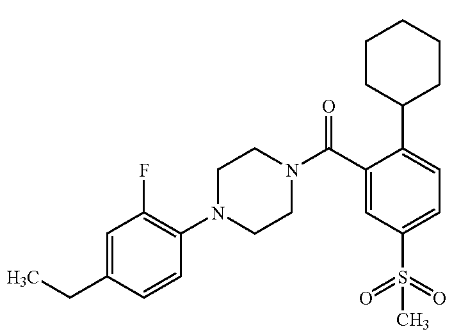 | 472.6 | 474.0 | (2-Cyclohexyl-5-methanesulfonyl-phenyl)-[4-(4-ethyl-2-fluoro-phenyl)-piperazin-1-yl]-methanone | K |

TABLE 2-continued

| | Structure | MW | M + H⁺ | Name | Procedure |
|---|---|---|---|---|---|
| 70 | 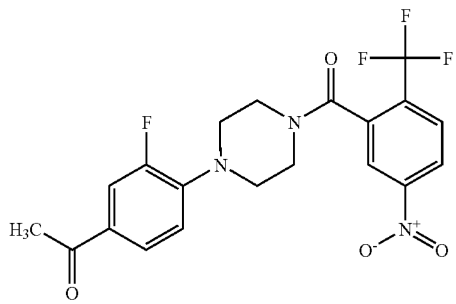 | 439.4 | 440.2 | 1-{3-Fluoro-4-[4-(5-nitro-2-trifluoromethyl-benzoyl)-piperazin-1-yl]-phenyl}-ethanone | E |
| 71 | 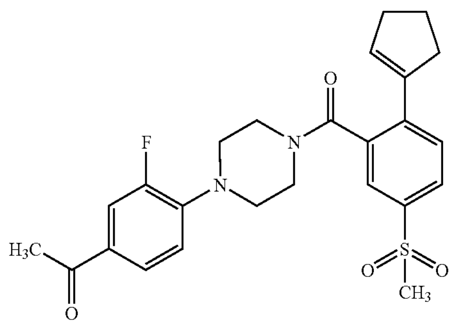 | 470.6 | 471.4 | 1-{4-[4-(2-Cyclopent-1-enyl-5-methanesulfonyl-benzoyl)-piperazin-1-yl]-3-fluoro-phenyl}-ethanone | E |
| 72 | 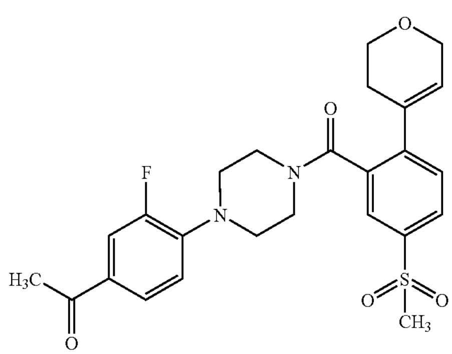 | 486.6 | 487.4 | 1-(4-{4-[2-(3,6-Dihydro-2H-pyran-4-yl)-5-methanesulfonyl-benzoyl]-piperazin-1-yl}-3-fluoro-phenyl)-ethanone | E |
| 73 | 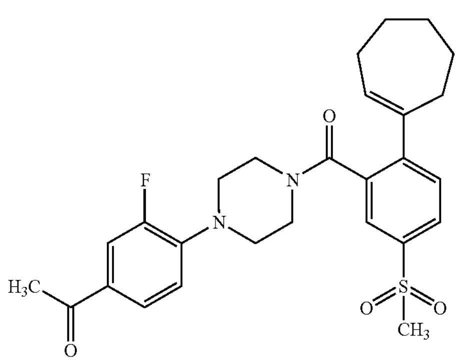 | 498.6 | 499.4 | 1-{4-[4-(2-Cyclohept-1-enyl-5-methanesulfonyl-benzoyl)-piperazin-1-yl]-3-fluoro-phenyl}-ethanone | E |

TABLE 2-continued

| | Structure | MW | M + H⁺ | Name | Procedure |
|---|---|---|---|---|---|
| 74 | 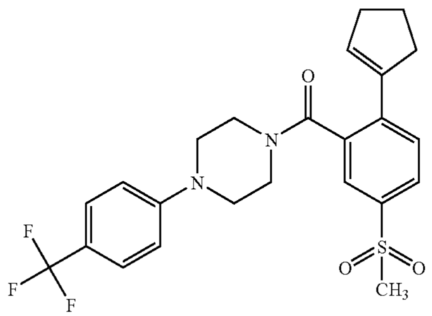 | 478.5 | 479.5 | (2-Cyclopent-1-enyl-5-methanesulfonyl-phenyl)-[4-(4-trifluoromethyl-phenyl)-piperazin-1-yl]-methanone | E |
| 75 | 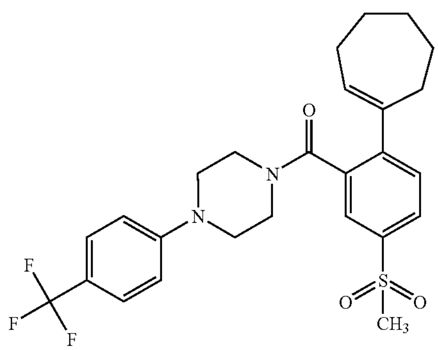 | 506.6 | 507.5 | (2-Cyclohept-1-enyl-5-methanesulfonyl-phenyl)-[4-(4-trifluoromethyl-phenyl)-piperazin-1-yl]-methanone | E |
| 76 | 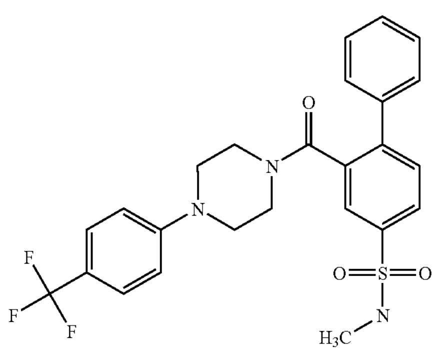 | 503.5 | 504.4 | 2-[4-(4-Trifluoromethyl-phenyl)-piperazine-1-carbonyl]-biphenyl-4-sulfonic acid methylamide | O |
| 77 | 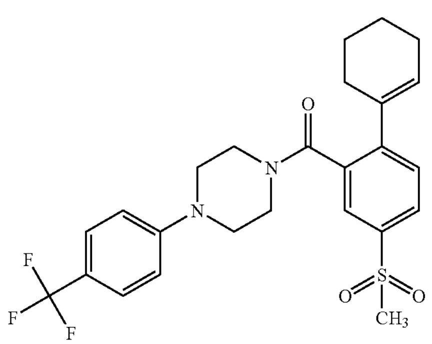 | 492.6 | 493.2 | (2-Cyclohex-1-enyl-5-methanesulfonyl-phenyl)-[4-(4-trifluoromethyl-phenyl)-piperazin-1-yl]-methanone | E |

TABLE 2-continued

| | Structure | MW | M + H+ | Name | Procedure |
|---|---|---|---|---|---|
| 78 | 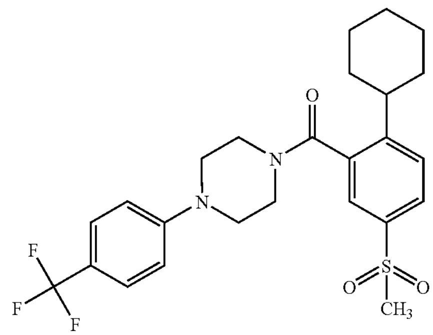 | 494.6 | 495.9 | (2-Cyclohexyl-5-methanesulfonyl-phenyl)-[4-(4-trifluoromethyl-phenyl)-piperazin-1-yl]-methanone | K |
| 79 | 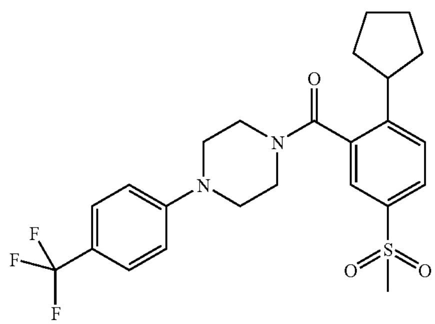 | 480.5 | 481.5 | (2-Cyclopentyl-5-methanesulfonyl-phenyl)-[4-(4-trifluoromethyl-phenyl)-piperazin-1-yl]-methanone | P |
| 80 | 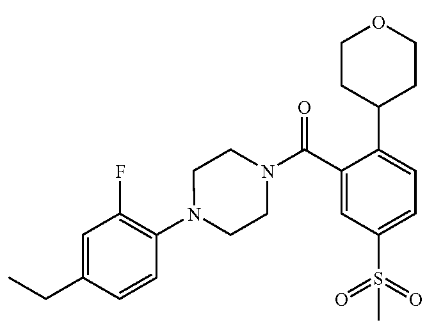 | 474.5 | 475.5 | [4-(4-Ethyl-2-fluoro-phenyl)-piperazin-1-yl]-[5-methanesulfonyl-2-(tetrahydro-pyran-4-yl)-phenyl]-methanone | Q |
| 81 | 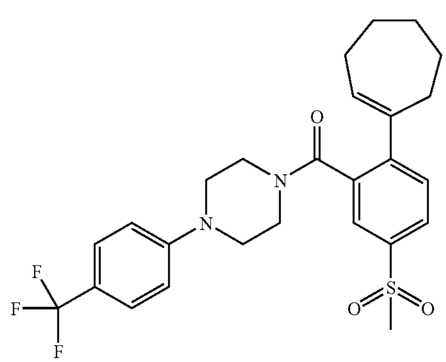 | 508.6 | 509.6 | (2-Cycloheptyl-5-methanesulfonyl-phenyl)-[4-(4-trifluoromethyl-phenyl)-piperazin-1-yl]-methanone | R |

TABLE 2-continued

| # | MW | M + H⁺ | Name | Procedure |
|---|---|---|---|---|
| 82 | 470.5 | 471.0 | 2-Fluoro-4-[4-(5-methanesulfonyl-2-thiazol-2-yl-benzoyl)-piperazin-1-yl]-benzonitrile | E |
| 83 | 452.5 | 453.5 | 4-[4-(5-Methanesulfonyl-2-thiazol-2-yl-benzoyl)-piperazin-1-yl]-benzonitrile | E |
| 84 | 470.5 | 471.4 | 3-Fluoro-4-[4-(5-methanesulfonyl-2-thiazol-2-yl-benzoyl)-piperazin-1-yl]-benzonitrile | E |
| 85 | 487.5 | 488.5 | 1-{3-Fluoro-4-[4-(5-methanesulfonyl-2-thiazol-2-yl-benzoyl)-piperazin-1-yl]-phenyl}-ethanone | E |
| 86 | 513.5 | 514.5 | [4-(3-Fluoro-4-trifluoromethyl-phenyl)-piperazin-1-yl]-(5-methanesulfonyl-2-thiazol-2-yl-phenyl)-methanone | E |

TABLE 2-continued

| | Structure | MW | M + H+ | Name | Procedure |
|---|---|---|---|---|---|
| 87 | 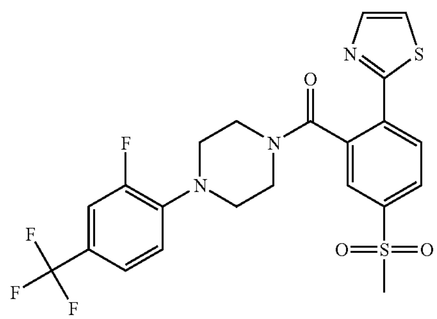 | 513.5 | 514.3 | [4-(2-Fluoro-4-trifluoromethyl-phenyl)-piperazin-1-yl]-(5-methanesulfonyl-2-thiazol-2-yl-phenyl)-methanone | E |
| 88 | 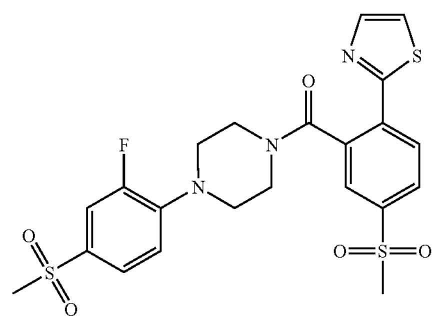 | 523.6 | 524.3 | [4-(2-Fluoro-4-methanesulfonyl-phenyl)-piperazin-1-yl]-(5-methanesulfonyl-2-thiazol-2-yl-phenyl)-methanone | E |
| 89 | 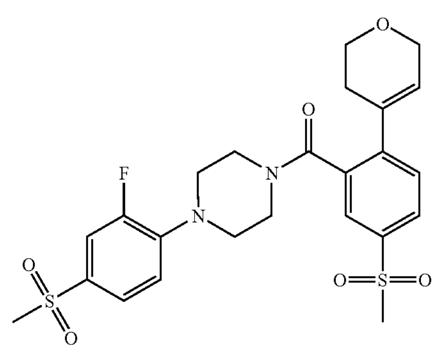 | 522.6 | 540.3 (M + NH4+) | [2-(3,6-Dihydro-2H-pyran-4-yl)-5-methanesulfonyl-phenyl]-[4-(2-fluoro-4-methanesulfonyl-phenyl)-piperazin-1-yl]-methanone | S |
| 90 | 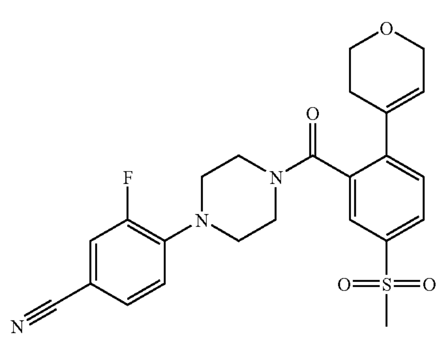 | 469.5 | 470.1 | 4-{4-[2-(3,6-Dihydro-2H-pyran-4-yl)-5-methanesulfonyl-benzoyl]-piperazin-1-yl}-3-fluoro-benzonitrile | S |

TABLE 2-continued

| | Structure | MW | M + H+ | Name | Procedure |
|---|---|---|---|---|---|
| 91 | 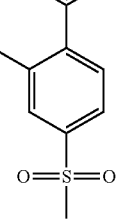 | 512.5 | 513.2 | [2-(3,6-Dihydro-2H-pyran-4-yl)-5-methanesulfonyl-phenyl]-[4-(2-fluoro-4-trifluoromethyl-phenyl)-piperazin-1-yl]-methanone | S |
| 92 | 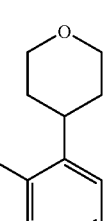 | 524.6 | 525.4 | [4-(2-Fluoro-4-methanesulfonyl-phenyl)-piperazin-1-yl]-[5-methanesulfonyl-2-(tetrahydro-pyran-4-yl)-phenyl]-methanone | L |
| 93 | 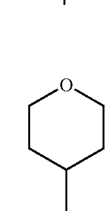 | 514.5 | 515.3 | [4-(2-Fluoro-4-trifluoromethyl-phenyl)-piperazin-1-yl]-[5-methanesulfonyl-2-(tetrahydro-pyran-4-yl)-phenyl]-methanone | L |
| 94 | 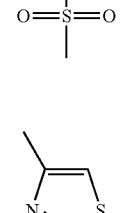 | 509.5 | 510.5 | [5-Methanesulfonyl-2-(4-methyl-thiazol-2-yl)-phenyl]-[4-(4-trifluoromethyl-phenyl)-piperazin-1-yl]-methanone | T |

TABLE 2-continued

| | Structure | MW | M + H+ | Name | Procedure |
|---|---|---|---|---|---|
| 95 | 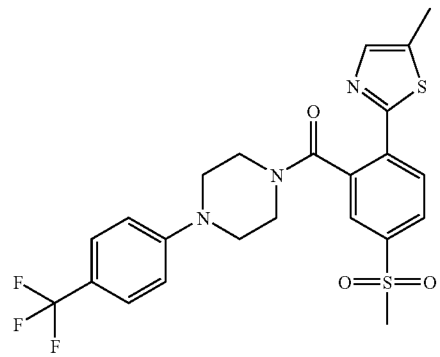 | 509.5 | 510.3 | [5-Methanesulfonyl-2-(5-methyl-thiazol-2-yl)-phenyl]-[4-(4-trifluoro-methyl-phenyl)-piperazin-1-ylmethanone | T |
| 96 | 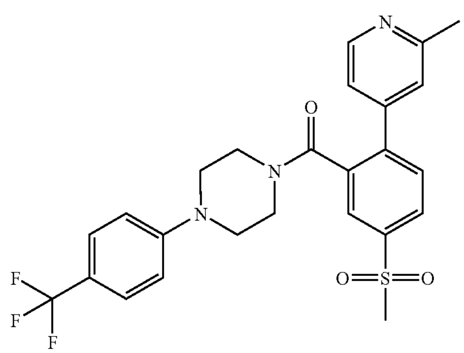 | 503.5 | 504.0 | [5-Methanesulfonyl-2-(2-methyl-pyridin-4-yl)-phenyl]-[4-(4-trifluoromethyl-phenyl)-piperazin-1-yl]-methanone | T |
| 97 | 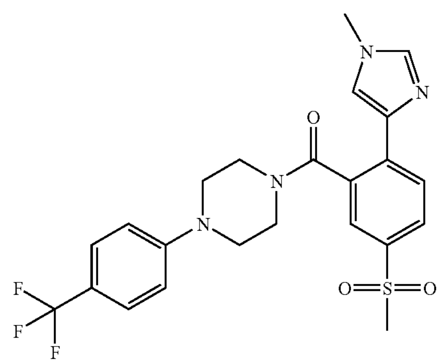 | 492.5 | 493.3 | [5-Methanesulfonyl-2-(1-methyl-1H-imidazol-4-yl)-phenyl]-[4-(4-trifluoromethyl-phenyl)-piperazin-1-yl]-methanone | T |
| 98 | 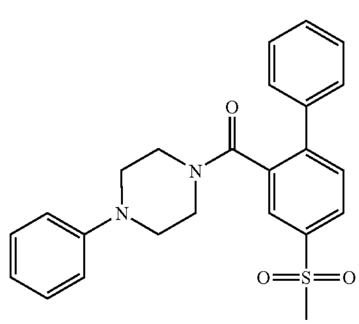 | 420.5 | 421.3 | (4-Methanesulfonyl-biphenyl-2-yl)-(4-phenyl-piperazin-1-yl)-methanone | E |

TABLE 2-continued

| | Structure | MW | M + H⁺ | Name | Procedure |
|---|---|---|---|---|---|
| 99 | lp;1p | 436.5 | 437.4 | [4-(4-Hydroxy-phenyl)-piperazin-1-yl]-(4-methanesulfonyl-biphenyl-2-yl)-methanone | E |
| 100 | 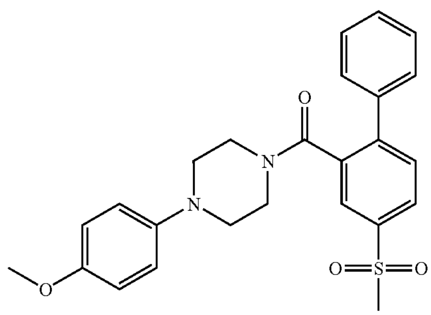 | 450.5 | 451.1 | (4-Methanesulfonyl-biphenyl-2-yl)-[4-(4-methoxy-phenyl)-piperazin-1-yl]-methanone | E |
| 101 | 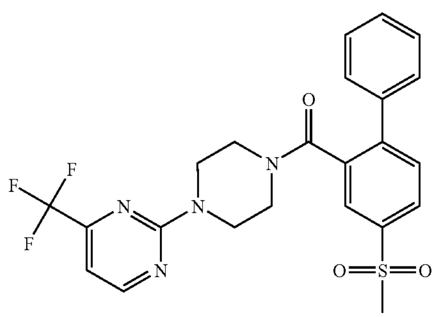 | 490.5 | 491.1 | (4-Methanesulfonyl-biphenyl-2-yl)-[4-(4-trifluoromethyl-pyrimidin-2-yl)-piperazin-1-yl]-methanone | E |
| 102 | 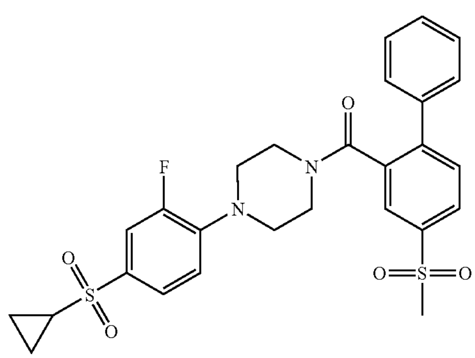 | 542.6 | 543.3 | [4-(4-Cyclopropanesulfonyl-2-fluoro-phenyl)-piperazin-1-yl]-(4-methane-sulfonyl-biphenyl-2-yl)-methanone | E |

TABLE 2-continued

| | Structure | MW | M + H⁺ | Name | Procedure |
|---|---|---|---|---|---|
| 103 | 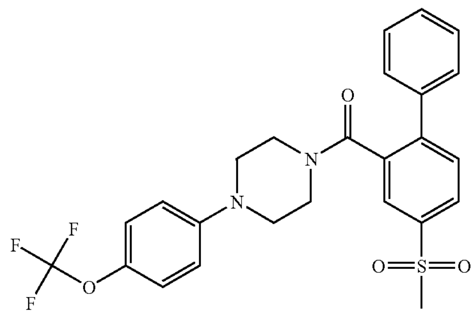 | 504.5 | 505.4 | (4-Methanesulfonyl-biphenyl-2-yl)-[4-(4-trifluoromethoxy-phenyl)-piperazin-1-yl]-methanone | E |
| 104 | 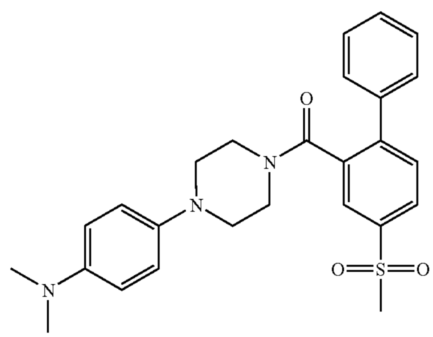 | 463.5 | 464.3 | [4-(4-Dimethylamino-phenyl)-piperazin-1-yl]-(4-methanesulfonyl-biphenyl-2-yl)-methanone | E |
| 105 | 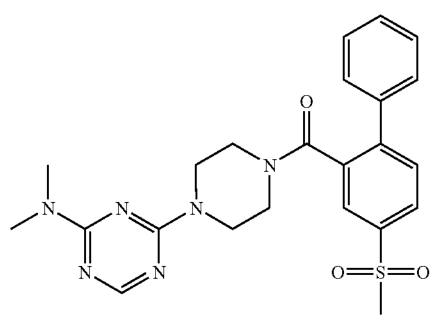 | 466.5 | 467.4 | [4-(4-Dimethylamino-[1,3,5]triazin-2-yl)-piperazin-1-yl]-(4-methanesulfonyl-biphenyl-2-yl)-methanone | E |
| 106 | 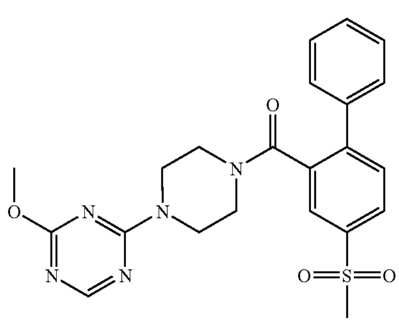 | 453.5 | 454.5 | (4-Methanesulfonyl-biphenyl-2-yl)-[4-(4-methoxy-[1,3,5]triazin-2-yl)-piperazin-1-yl]-methanone | E |

TABLE 2-continued
| | Structure | MW | M + H⁺ | Name | Procedure |
|---|---|---|---|---|---|
| 107 | 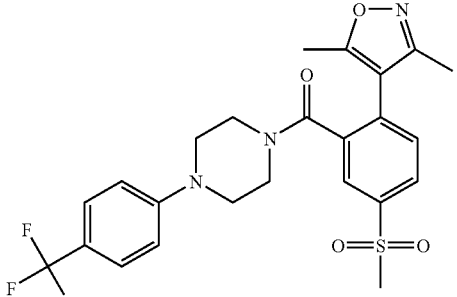 | 507.5 | 508 | [2-(3,5-Dimethyl-isoxazol-4-yl)-5-methanesulfonyl-phenyl]-[4-(4-trifluoromethyl-phenyl)-piperazin-1-yl]-methanone | G |
| 108 | 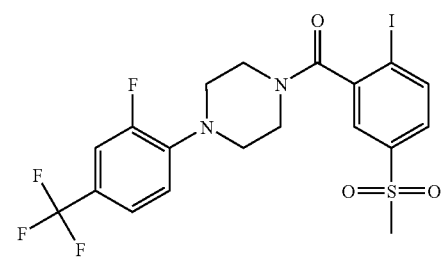 | 556.3 | 556.9 | [4-(2-Fluoro-4-trifluoromethyl-phenyl)-piperazin-1-yl]-(2-iodo-5-methanesulfonyl-phenyl)-methanone | E |
| 109 | 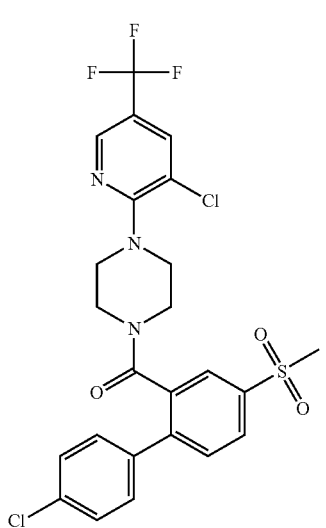 | 558.4 | 558 | (4'-Chloro-4-methanesulfonyl-biphenyl-2-yl)-[4-(3-chloro-5-trifluoromethyl-pyridin-2-yl)-piperazin-1-yl]-methanone | E |

TABLE 2-continued

| | Structure | MW | M + H⁺ | Name | Procedure |
|---|---|---|---|---|---|
| 110 | 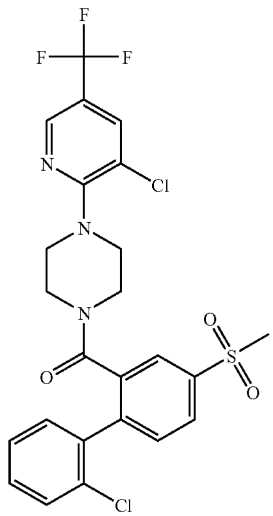 | 558.4 | no MS | (2'-Chloro-4-methanesulfonyl-biphenyl-2-yl)-[4-(3-chloro-5-yl)-piperazin-1-yl]-methanone | E |
| 111 | 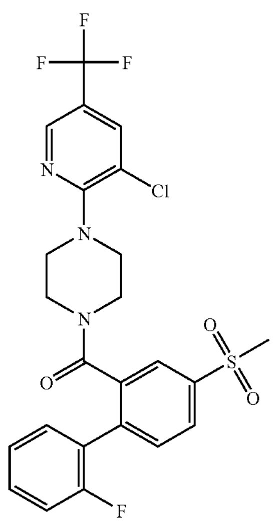 | 541.9 | 542 | [4-(3-Chloro-5-trifluoromethyl-pyridin-2-yl)-piperazin-1-yl]-(2'-fluoro-4-methanesulfonyl-biphenyl-2-yl)-methanone | E |
| 112 | 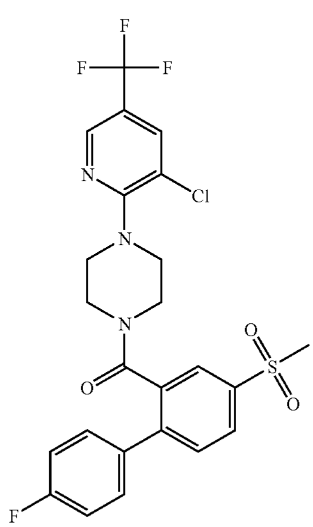 | 541.9 | 542 | [4-(3-Chloro-5-trifluoromethyl-pyridin-2-yl)-piperazin-1-yl]-(4'-fluoro-4-methanesulfonyl-biphenyl-2-yl)-methanone | E |

TABLE 2-continued

| | Structure | MW | M + H+ | Name | Procedure |
|---|---|---|---|---|---|
| 113 | 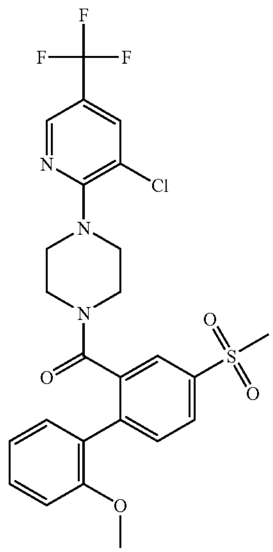 | 553.9 | 554 | [4-(3-Chloro-5-trifluoromethyl-pyridin-2-yl)-piperazin-1-yl]-(4-methanesulfonyl-2'-methoxy-biphenyl-2-yl)-methanone | E |
| 114 | 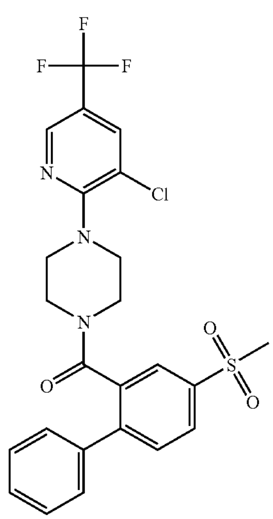 | 523.9 | 524 | [4-(3-Chloro-5-trifluoromethyl-pyridin-2-yl)-piperazin-1-yl]-(4-methanesulfonyl-biphenyl-2-yl)-methanone | E |

TABLE 2-continued
| | Structure | MW | M + H⁺ | Name | Procedure |
|---|---|---|---|---|---|
| 115 | 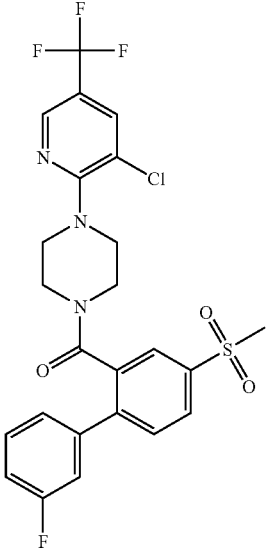 | 541.9 | 542 | [4-(3-Chloro-5-trifluoromethyl-pyridin-2-yl)-piperazin-1-yl]-(3'-fluoro-4-methanesulfonyl-biphenyl-2-yl)-methanone | E |
| 116 | 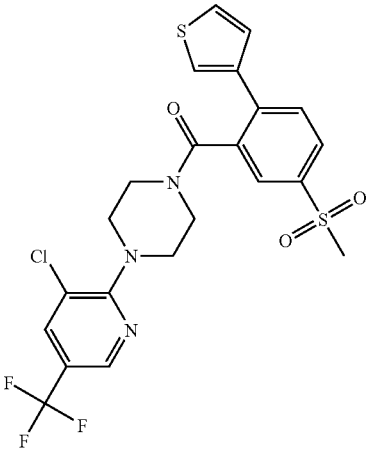 | 529.9 | 530 | [4-(3-Chloro-5-trifluoromethyl-pyridin-2-yl)-piperazin-1-yl]-(5-methanesulfonyl-2-thiophen-3-yl-phenyl)-methanone | E |
| 117 | 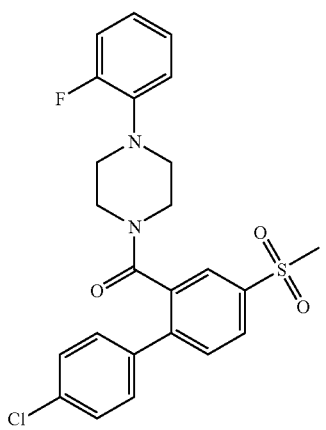 | 472.9 | 473 | (4'-Chloro-4-methanesulfonyl-biphenyl-2-yl)-[4-(2-fluoro-phenyl)-piperazin-1-yl]-methanone | E |

TABLE 2-continued

| | Structure | MW | M + H+ | Name | Procedure |
|---|---|---|---|---|---|
| 118 | 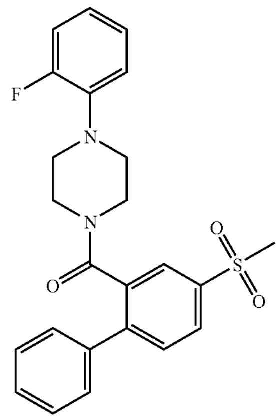 | 438.5 | 439 | [4-(2-Fluoro-phenyl)-piperazin-1-yl]-(4-methanesulfonyl-biphenyl-2-yl)-methanone | E |
| 119 | 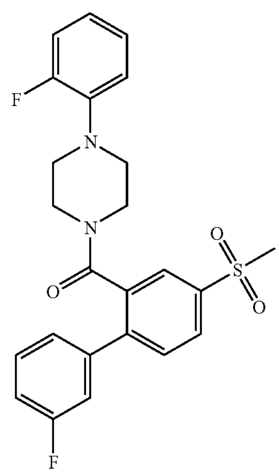 | 456.5 | 457 | (3'-Fluoro-4-methanesulfonyl-biphenyl-2-yl)-[4-(2-fluoro-phenyl)-piperazin-1-yl]-methanone | E |
| 120 | 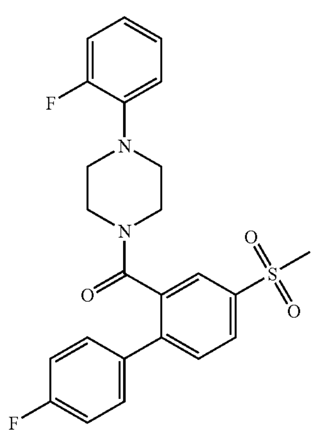 | 456.5 | 457 | (4'-Fluoro-4-methanesulfonyl-biphenyl-2-yl)-[4-(2-fluoro-phenyl)-piperazin-1-yl]-methanone | E |

TABLE 2-continued

| | Structure | MW | M + H⁺ | Name | Procedure |
|---|---|---|---|---|---|
| 121 | 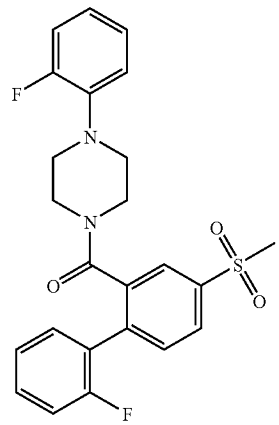 | 456.5 | 457 | (2'-Fluoro-4-methanesulfonyl-biphenyl-2-yl)-[4-(2-fluoro-phenyl)-piperazin-1-yl]-methanone | E |
| 122 | 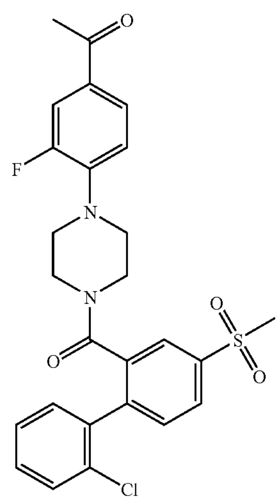 | 515.0 | 515 | 1-{4-[4-(2'-Chloro-4-methane-sulfonyl-biphenyl-2-carbonyl)-piperazin-1-yl]-3-fluoro-phenyl}-ethanone | E |
| 123 | 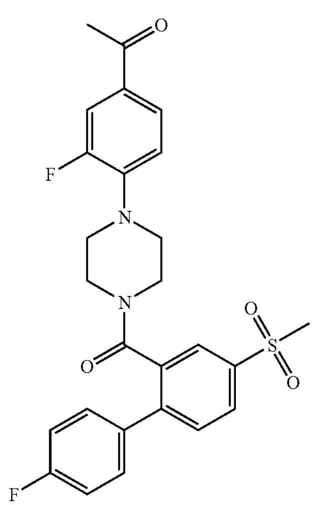 | 498.5 | 499 | 1-{3-Fluoro-4-[4-(4'-fluoro-4-methanesulfonyl-biphenyl-2-carbonyl)-piperazin-1-yl]-phenyl}-ethanone | E |

TABLE 2-continued

| | Structure | MW | M + H⁺ | Name | Procedure |
|---|---|---|---|---|---|
| 124 | 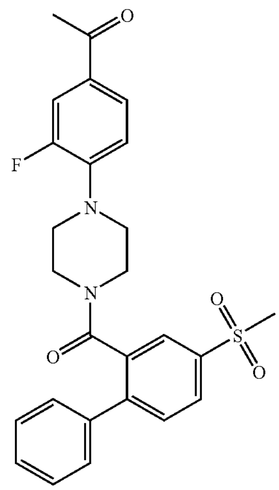 | 480.5 | 481 | 1-{3-Fluoro-4-[4-(4-methanesulfonyl-biphenyl-2-carbonyl)-piperazin-1-yl]-phenyl}-ethanone | E |
| 125 | 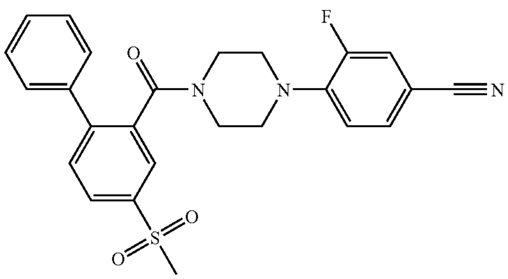 | 463.5 | 464 | 3-Fluoro-4-[4-(4-methanesulfonyl-biphenyl-2-carbonyl)-piperazin-1-yl]-benzonitrile | E |
| 126 | 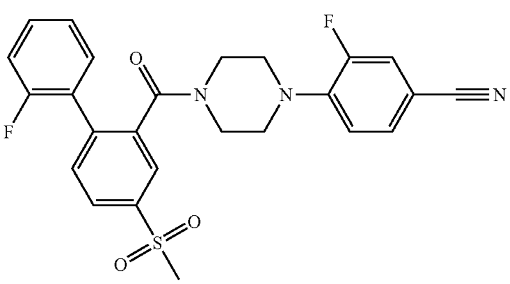 | 481.5 | 482 | 3-Fluoro-4-[4-(2'-fluoro-4-methane-sulfonyl-biphenyl-2-carbonyl)-piperazin-1-yl]-benzonitrile | E |
| 127 | 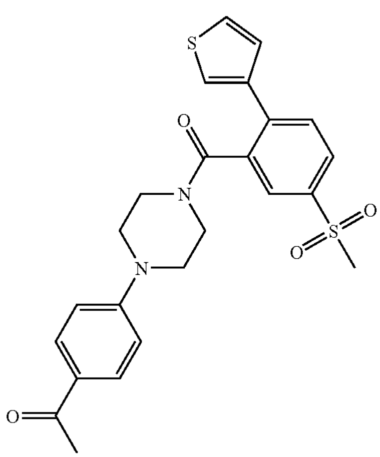 | 468.6 | 469 | 1-{4-[4-(5-Methanesulfonyl-2-thiophen-3-yl-benzoyl)-piperazin-1-yl]-phenyl}-ethanone | E |

TABLE 2-continued

| | Structure | MW | M + H⁺ | Name | Procedure |
|---|---|---|---|---|---|
| 128 | 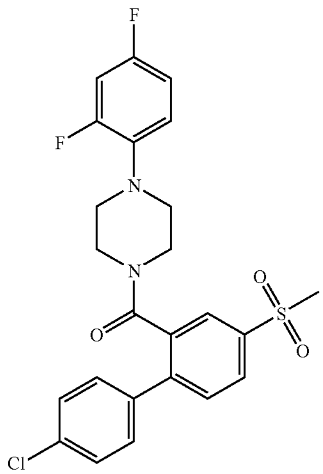 | 490.9 | 592 (M + H + TEA) | (4'-Chloro-4-methanesulfonyl-biphenyl-2-yl)-[4-(2,4-difluoro-phenyl)-piperazin-1-yl]-methanone | E |
| 129 | 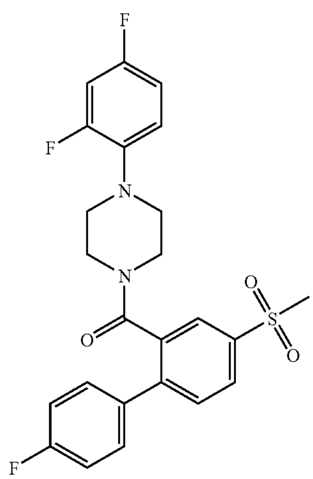 | 474.5 | 576 (M + H + TEA) | [4-(2,4-Difluoro-phenyl)-piperazin-1-yl]-(4'-fluoro-4-methanesulfonyl-biphenyl-2-yl)-methanone | E |
| 130 | 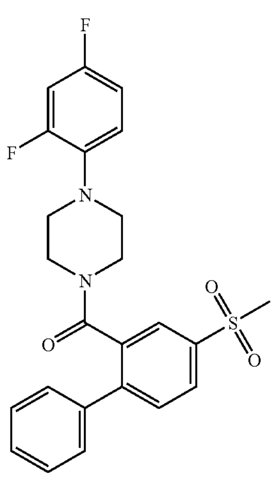 | 456.5 | 457 | [4-(2,4-Difluoro-phenyl)-piperazin-1-yl]-(4-methanesulfonyl-biphenyl-2-yl)-methanone | E |

TABLE 2-continued

| | Structure | MW | M + H⁺ | Name | Procedure |
|---|---|---|---|---|---|
| 131 | 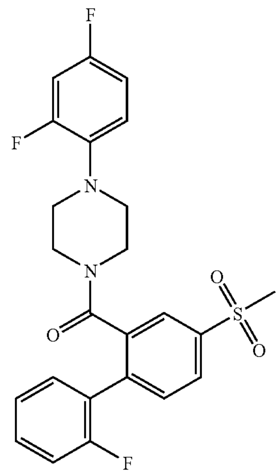 | 474.5 | 576 (M + H + TEA) | [4-(2,4-Difluoro-phenyl)-piperazin-1-yl]-(2'-fluoro-4-methanesulfonyl-biphenyl-2-yl)-methanone | E |
| 132 | 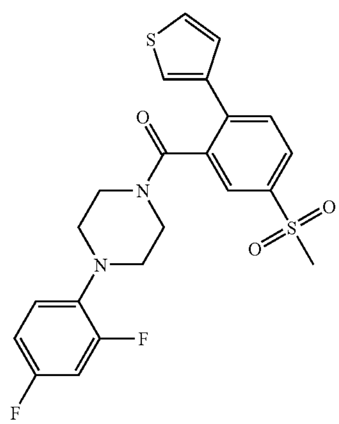 | 462.5 | 564 (M + H + TEA) | [4-(2,4-Difluoro-phenyl)-piperazin-1-yl]-(5-methanesulfonyl-2-thiophen-3-yl-phenyl)-methanone | E |
| 133 | 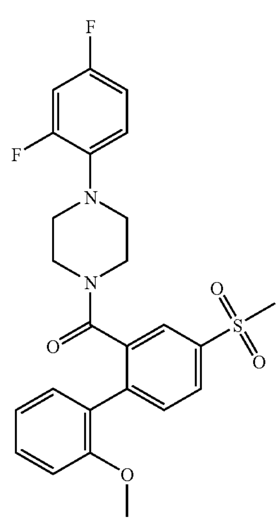 | 486.5 | 588 (M + H + TEA) | [4-(2,4-Difluoro-phenyl)-piperazin-1-yl]-(4-methanesulfonyl-2'-methoxy-biphenyl-2-yl)-methanone | E |

TABLE 2-continued

| | Structure | MW | M + H+ | Name | Procedure |
|---|---|---|---|---|---|
| 134 | 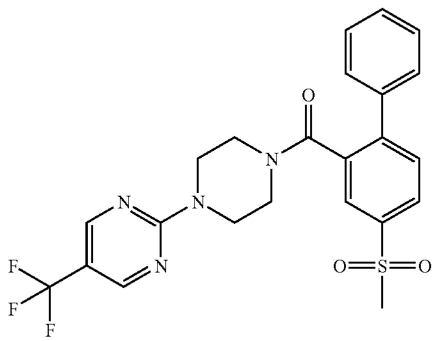 | 490.5 | 491.1 | (4-Methanesulfonyl-biphenyl-2-yl)-[4-(5-trifluoromethyl-pyrimidin-2-yl)-piperazin-1-yl]-methanone | E |
| 135 | 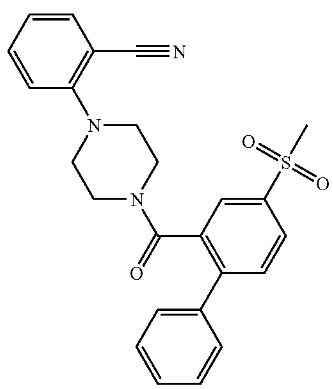 | 445.5 | 446 | 2-[4-(4-Methanesulfonyl-biphenyl-2-carbonyl)-piperazin-1-yl]-benzonitrile | E |
| 136 | 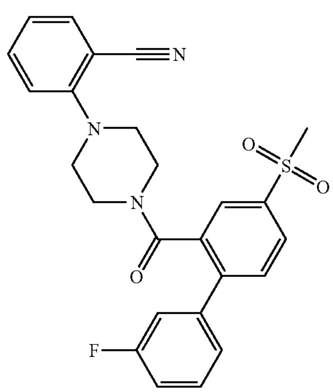 | 463.5 | 464 | 2-[4-(3'-Fluoro-4-methanesulfonyl-biphenyl-2-carbonyl)-piperazin-1-yl]-benzonitrile | E |
| 137 | 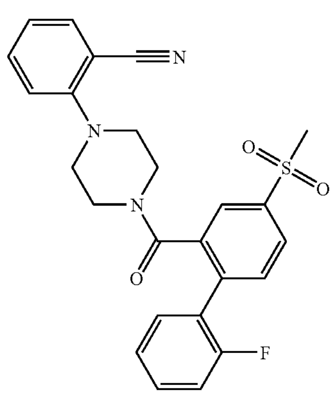 | 463.5 | 464 | 2-[4-(2'-Fluoro-4-methanesulfonyl-biphenyl-2-carbonyl)-piperazin-1-yl]-benzonitrile | E |

TABLE 2-continued

| | Structure | MW | M + H+ | Name | Procedure |
|---|---|---|---|---|---|
| 138 | 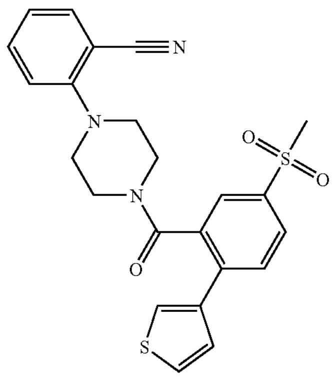 | 451.5 | 452 | 2-[4-(5-Methanesulfonyl-2-thiophen-3-yl-benzoyl)-piperazin-1-yl]-benzonitrile | E |
| 139 | 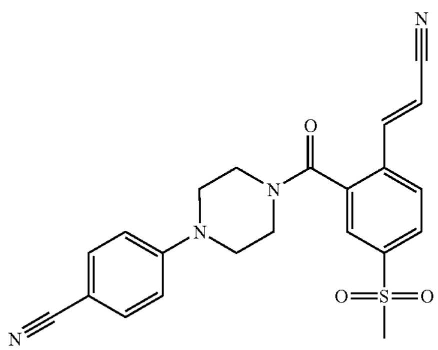 | 420.4 | 421 | 4-{4-[2-((E)-2-Cyano-vinyl)-5-methanesulfonyl-benzoyl]-piperazin-1-yl}-benzonitrile | U |
| 140 | 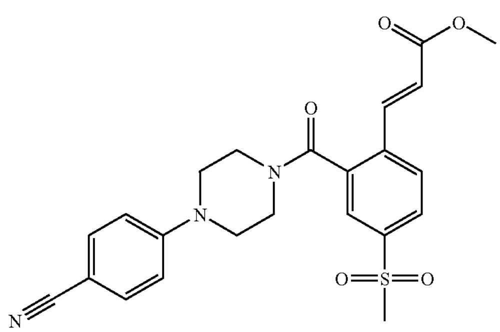 | 453.5 | 454 | (E)-3-{2-[4-(4-Cyano-phenyl)-piperazine-1-carbonyl]-4-methane-sulfonyl-phenyl}-acrylic acid methyl ester | U |

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

What is claimed is:

1. A compound of formula

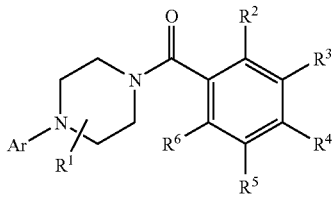

I wherein
- Ar is or unsubstituted or substituted 6-membered heteroaryl containing one, two or three nitrogen atoms, and wherein the substituted heteroaryl groups are substituted by one or more substituents selected from the group consisting of hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;
- $R^1$ is hydrogen or $(C_1-C_6)$-alkyl;
- $R^2$ is
  - $(C_1-C_6)$-alkyl,
  - $(C_2-C_6)$-alkenyl, wherein a hydrogen atom may be replaced by CN, C(O)—$R^9$ or $(C_1-C_6)$-alkyl,
  - or is $(C_2-C_6)$-alkynyl,
  - $(C_1-C_6)$-alkyl substituted by halogen,
  - —$(CH_2)_n$—$(C_3-C_7)$-cycloalkyl,
  - —$(CH_2)_n$-heterocycloalkyl,
  - —C(O)—$R^9$,
  - —$(CH_2)_n$-aryl
  - or —$(CH_2)_n$-5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;
- $R^3$, $R^4$ and $R^6$ are each independently hydrogen, hydroxy, halogen, $(C_1-C_6)$-alkyl or $(C_1-C_6)$-alkoxy;
- $R^5$ is CN, $C(O)R^9$, $SO_2R^{10}$ or $NR^{11}R^{12}$;
- $R^7$ and $R^8$ are each independently hydrogen or $(C_1-C_6)$-alkyl;
- $R^9$ is $(C_1-C_6)$-alkyl, $(C_3-C_6)$-cycloalkyl, $(C_1-C_6)$-alkoxy or $NR^7R^8$;
- $R^{10}$ is $(C_1-C_6)$-alkyl, $(C_3-C_6)$-cycloalkyl or $NR^7R^8$;
- $R^{11}$ and $R^{12}$ are each independently hydrogen, or form together with the N-atom to which they are attached a 5-membered heteroaryl group;
- n is 0, 1 or 2;

or a pharmaceutically acceptable acid addition salt thereof.

2. A compound of the formula

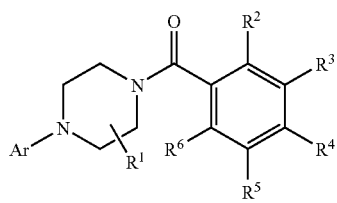

IA wherein
- Ar is unsubstituted or substituted 6-membered heteroaryl containing one, two or three nitrogen atoms, and wherein the substituted heteroaryl groups are substituted by one or more substituents selected from the group consisting of hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;
- $R^1$ is hydrogen or $(C_1-C_6)$-alkyl;
- $R^2$ is $(C_1-C_6)$-alkyl, $(C_2-C_6)$-alkenyl, $(C_2-C_6)$-alkynyl, $(C_1-C_6)$-alkyl substituted by halogen, $(C_3-C_7)$-cycloalkyl, heterocycloalkyl, $(C_1-C_6)$-alkyl-$(C_3-C_7)$-cycloalkyl, $(C_1-C_6)$-alkyl-heterocycloalkyl, —C(O)—$R^9$, aryl or 5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1-C_6)$-alkyl, $(C_1-C_6)$-alkyl substituted by halogen and $(C_1-C_6)$-alkoxy;
- $R^3$, $R^4$ and $R^6$ are each independently hydrogen, hydroxy, halogen, CN, $(C_1-C_6)$-alkyl, $(C_1-C_6)$-alkoxy or $NR^7R^8$;
- $R^5$ is CN, $C(O)R^9$, $SO_2R^{10}$ or $NR^{11}R^{12}$;
- $R^7$ and $R^8$ are each independently hydrogen or $(C_1-C_6)$-alkyl;
- $R^9$ is hydroxy, $(C_1-C_6)$-alkyl, $(C_3-C_6)$-cycloalkyl, $(C_1-C_6)$-alkoxy or $NR^7R^8$;
- $R^{10}$ is $(C_1-C_6)$-alkyl, $(C_3-C_6)$-cycloalkyl or $NR^7R^8$;
- $R^{11}$ and $R^{12}$ are each independently hydrogen, C(O)—$(C_1-C_6)$-alkyl, $SO_2$—$(C_1-C_6)$-alkyl, or form together with the N-atom to which they are attached a 5-membered heteroaryl group, optionally substituted by halogen, $(C_1-C_6)$-alkyl, $(C_1-C_6)$-alkyl substituted by halogen or $(C_3-C_6)$-cycloalkyl;

or a pharmaceutically acceptable acid addition salt thereof.

3. A compound of formula I-2 according to claim 1,

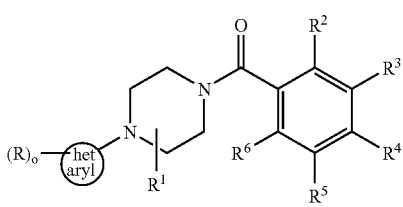

I-2 wherein
- R is hydroxy, halogen, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ or $SO_2R^{10}$;

o is 0, 1, 2 or 3;
R$^1$ is hydrogen;
R$^2$ is
  (C$_1$-C$_6$)-alkyl,
  (C$_2$-C$_6$)-alkenyl, wherein a hydrogen atom may be replaced by CN, C(O)—R$^9$ or
  (C$_1$-C$_6$)-alkyl,
  or is (C$_2$-C$_6$)-alkynyl,
  (C$_1$-C$_6$)-alkyl substituted by halogen,
  —(CH$_2$)$_n$—(C$_3$-C$_7$)-cycloalkyl,
  —(CH$_2$)$_n$-heterocycloalkyl,
  —C(O)—R$^9$,
  aryl or 5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, (C$_1$-C$_6$)-alkyl, (C$_1$-C$_6$)-alkyl substituted by halogen and (C$_1$-C$_6$)-alkoxy,
R$^3$, R$^4$ and R$^6$ are hydrogen;
R$^5$ is or SO$_2$R$^{10}$;
R$^7$ and R$^8$ are each independently hydrogen or (C$_1$-C$_6$)-alkyl;
R$^9$ is (C$_1$-C$_6$)-alkyl, (C$_3$-C$_6$)-cycloalkyl, (C$_1$-C$_6$)-alkoxy or NR$^7$R$^8$;
R$^{10}$ is (C$_1$-C$_6$)-alkyl, (C$_3$-C$_6$)-cycloalkyl or NR$^7$R$^8$;
n is 0, 1 or 2;
or a pharmaceutically acceptable acid addition salt thereof.

4. A compound of formula I-2 according to claim 3, wherein R$^2$ is aryl, unsubstituted or substituted by one or more substituents selected from the group consisting of hydroxy, halogen, (C$_1$-C$_6$)-alkyl, (C$_1$-C$_6$)-alkyl substituted by halogen and (C$_1$-C$_6$)-alkoxy.

5. A compound of formula I-2 according to claim 4, selected from the group consisting of
  [4-(3-chloro-5-trifluoromethyl-pyridin-2-yl)-piperazin-1-yl]-(2'-fluoro-4-methanesulfonyl-biphenyl-2-yl)-methanone and
  [4-(3-chloro-5-trifluoromethyl-pyridin-2-yl)-piperazin-1-yl]-(4-methanesulfonyl-biphenyl-2-yl) -methanone.

6. A compounds of formula I-2 according to claim 3, wherein R$^2$ is a 5 or-6-membered heteroaryl group containing one, two or three heteroatoms selected from the group consisting of oxygen, sulphur and nitrogen.

7. A compound of formula I-2 according to claim 6, which compound is
  [4-(3-chloro-5-trifluoromethyl-pyridin-2-yl)-piperazin-1-yl]-(5-methanesulfonyl-2-thiophen-3-yl-phenyl)-methanone.

8. A process for preparation of a compound of formula I or a pharmaceutically acceptable salt thereof, which process comprises
  reacting a compound of formula

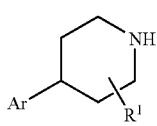

II with a compound of formula

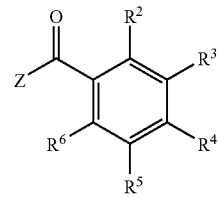

III to produce a compound of formula

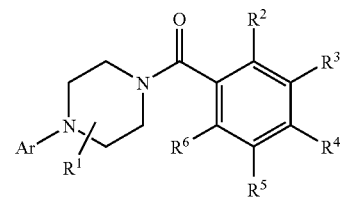

I wherein Z is hydroxy or halogen, and the other substituents are as defined in claim 1.

9. A process for preparation of a compound of formula I or a pharmaceutically acceptable salt thereof, which process comprises reacting a compound of formula

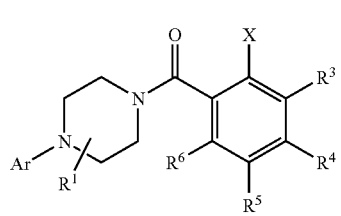

Ib with a compound of formula
  R$^2$B(OH)$_2$ or R$^2$B(OR)$_2$ in the presence of a palladium catalyst to produce a compound of formula

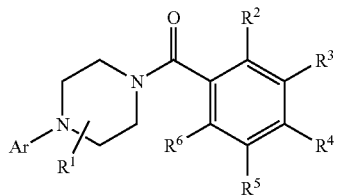

wherein X is halogen and the other substituents are as defined in claim 1.

10. A process for preparation of a compound of formula I or pharmaceutically acceptable salt thereof, which process comprises reacting a compound of formula

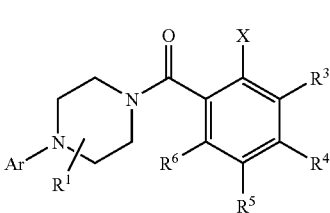

with $R^2SnBu_3$ or $R^2SnMe_3$ in the presence of a palladium catalyst to produce a compound of formula

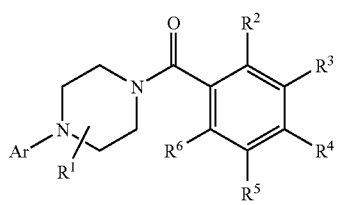

wherein X is halogen and the other substituents are as defined in claim 1.

11. A process for preparation of a compound of formula I or a pharmaceutically acceptable salt thereof, which process comprises reacting a compound of formula

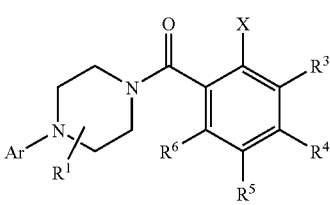

with a compound of formula

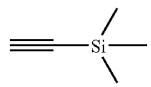

in the presence of a palladium catalyst and base to produce a compound of formula

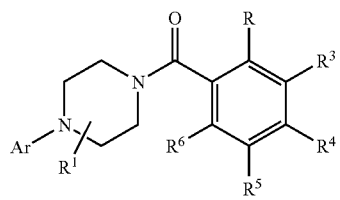

wherein X is halogen and the other substituents are as defined in claim 1.

12. A process for preparation of a compound of formula I or a pharmaceutically acceptable salt thereof, which process comprises hydrogenating a compound of formula

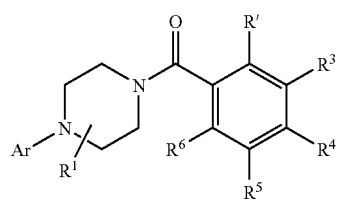

wherein R is $(C_2-C_6)$-alkenyl or $(C_2-C_6)$-alknyl to produce a compound of formula

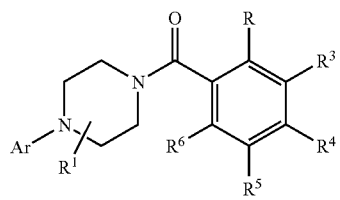

wherein R' is $(C_2-C_6)$-alkyl or $(C_2-C_6)$-alkenyl and the other substituents are as defined in claim 1.

13. A process for preparation of a compound of formula I or a pharmaceutically acceptable salt thereof, which process comprises reacting a compound of formula

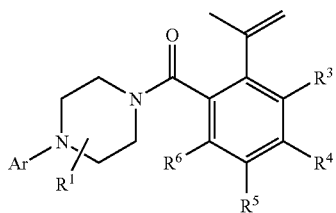

If with trimethylsulfoxonium iodide in the presence of a base to produce a compound of formula

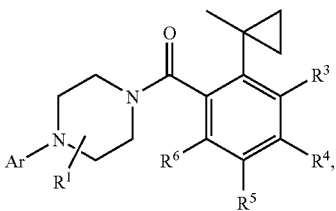

Ig wherein the substituents are as defined in claim 1.

14. A process for preparation of a compound of formula I or a pharmaceutically acceptable salt thereof, which process comprises reacting a compound of formula

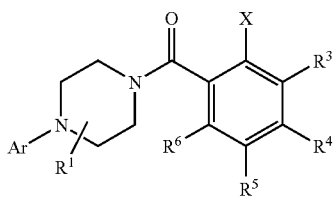

Ib with a compound of formula TMSCF$_3$ in the presence of copper to produce a compound of formula

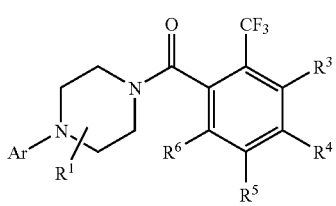

Ih wherein X is halogen and the other substituents are as described in claim 1.

15. A composition comprising one or more compounds of formula I

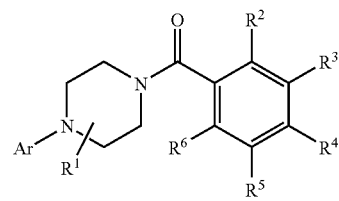

I wherein

Ar is unsubstituted or substituted 6-membered heteroaryl containing one, two or three nitrogen atoms, and wherein the substituted heteroaryl groups are substituted by one or more substituents selected from the group consisting of hydroxy, halogen, CN, (C$_1$-C$_6$)-alkyl, (C$_1$-C$_6$)-alkyl substituted by halogen, (C$_1$-C$_6$)-alkoxy, (C$_1$-C$_6$)-alkoxy substituted by halogen, NR$^7$R$^8$, C(O)R$^9$ and SO$_2$R$^{10}$;

R$^1$ is hydrogen or (C$_1$-C$_6$)-alkyl;

R$^2$ is halogen, (C$_1$-C$_6$)-alkyl, (C$_2$-C$_6$)-alkenyl, wherein a hydrogen atom may be replaced by CN, C(O)—R$^9$ or (C$_1$-C$_6$)-alkyl, or is (C$_2$-C$_6$)-alkynyl, (C$_1$-C$_6$)-alkyl substituted by halogen, —(CH$_2$)$_n$-(C$_3$-C$_7$)-cycloalkyl, —(CH$_2$)$_n$-heterocycloalkyl,

—C(O)—R$^9$,

—(CH$_2$)$_n$-aryl or —(CH$_2$)$_n$-5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, (C$_1$-C$_6$)-alkyl, (C$_1$-C$_6$)-alkyl substituted by halogen and (C$_1$-C$_6$)-alkoxy;

R$^3$, R$^4$ and R$^6$ are each independently hydrogen, hydroxy, halogen, (C$_1$-C$_6$)-alkyl or (C$_1$-C$_6$)-alkoxy;

R$^5$ is NO$_2$, CN, C(O)R$^9$, SO$_2$R$^{10}$ or NR$^{11}$R$^{12}$;

R$^7$ and R$^8$ are each independently hydrogen or (C$_1$-C$_6$)-alkyl;

R$^9$ is (C$_1$-C$_6$)-alkyl, (C$_3$-C$_6$)-cycloalkyl, (C$_1$-C$_6$)-alkoxy or NR$^7$R$^8$;

R$^{10}$ is (C$_1$-C$_6$)-alkyl, (C$_3$-C$_6$)-cycloalkyl or NR$^7$R$^8$;

R$^{11}$ and R$^{12}$ are each independently hydrogen, or form together with the N-atom to which they are attached a 5-membered heteroaryl group;

n is 0, 1 or 2;

or a pharmaceutically acceptable acid addition salt thereof, and a therapeutically inert carrier.

16. A method of treating schizophrenia, comprising administering to an individual a therapeutically effective amount of a compound of formula I

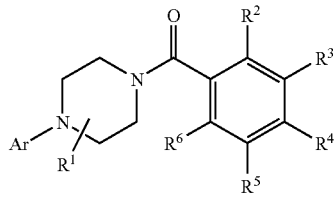

wherein
- Ar is unsubstituted or substituted 6-membered heteroaryl containing one, two or three nitrogen atoms, and wherein the substituted heteroaryl groups are substituted by one or more substituents selected from the group consisting of hydroxy, halogen, CN, $(C_1\text{-}C_6)$-alkyl, $(C_1\text{-}C_6)$-alkyl substituted by halogen, $(C_1\text{-}C_6)$-alkoxy, $(C_1\text{-}C_6)$-alkoxy substituted by halogen, $NR^7R^8$, $C(O)R^9$ and $SO_2R^{10}$;
- $R^1$ is hydrogen or $(C_1\text{-}C_6)$-alkyl;
- $R^2$ is halogen,
  - $(C_1\text{-}C_6)$-alkyl,
  - $(C_2\text{-}C_6)$-alkenyl, wherein a hydrogen atom may be replaced by CN, $C(O)$—$R^9$ or $(C_1\text{-}C_6)$-alkyl,
  - or is $(C_2\text{-}C_6)$-alkynyl,
  - $(C_1\text{-}C_6)$-alkyl substituted by halogen,
  - —$(CH_2)_n$-$(C_3\text{-}C_7)$-cycloalkyl,
  - —$(CH_2)_n$-heterocycloalkyl,
  - —$C(O)$—$R^9$,
  - —$(CH_2)_n$-aryl
  - or —$(CH_2)_n$-5 or-6-membered heteroaryl containing one, two or three heteroatoms selected from the group consisting of oxygen, sulphur and nitrogen wherein aryl, cycloalkyl, heterocycloalkyl and heteroaryl are unsubstituted or substituted by one or more substituents selected from the group consisting of hydroxy, halogen, $(C_1\text{-}C_6)$-alkyl, $(C_1\text{-}C_6)$-alkyl substituted by halogen and $(C_1\text{-}C_6)$-alkoxy;
- $R^3$, $R^4$ and $R^6$ are each independently hydrogen, hydroxy, halogen, $(C_1\text{-}C_6)$-alkyl or $(C_1\text{-}C_6)$-alkoxy;
- $R^5$ is $NO_2$, CN, $C(O)R^9$, $SO_2R^{10}$ or $NR^{11}R^{12}$;
- $R^7$ and $R^8$ are each independently hydrogen or $(C_1\text{-}C_6)$-alkyl;
- $R^9$ is $(C_1\text{-}C_6)$-alkyl, $(C_3\text{-}C_6)$-cycloalkyl, $(C_1\text{-}C_6)$-alkoxy or $NR^7R^8$;
- $R^{10}$ is $(C_1\text{-}C_6)$-alkyl, $(C_3\text{-}C_6)$-cycloalkyl or $NR^7R^8$;
- $R^{11}$ and $R^{12}$ are each independently hydrogen, or form together with the N-atom to which they are attached a 5-membered heteroaryl group;
- n is 0, 1 or 2;

or a pharmaceutically acceptable acid addition salt thereof.

* * * * *